(12) United States Patent
Abysalh et al.

(10) Patent No.: US 11,453,877 B2
(45) Date of Patent: Sep. 27, 2022

(54) METHODS FOR PURIFICATION OF MESSENGER RNA

(71) Applicant: Translate Bio, Inc., Lexington, MA (US)

(72) Inventors: Jonathan Abysalh, Lexington, MA (US); Frank DeRosa, Lexington, MA (US); Jorel E. Vargas, Lexington, MA (US); Cameron M. Smith, Lexington, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 16/875,418

(22) Filed: May 15, 2020

(65) Prior Publication Data

US 2021/0002635 A1   Jan. 7, 2021

Related U.S. Application Data

(60) Provisional application No. 62/891,781, filed on Aug. 26, 2019, provisional application No. 62/848,412, filed on May 15, 2019.

(51) Int. Cl.
*C12N 15/10*   (2006.01)

(52) U.S. Cl.
CPC .................... *C12N 15/1096* (2013.01)

(58) Field of Classification Search
CPC ............ C12N 15/1003; C12N 15/1017; C12N 15/101; C12N 15/1013; C12N 15/1006; C12N 15/10; C12N 15/1096; C12Q 1/6806

See application file for complete search history.

(56) References Cited

U.S. PATENT DOCUMENTS

| | | | | |
|---|---|---|---|---|
| 5,576,196 A | * | 11/1996 | Horn | C12N 1/08 435/5 |
| 5,707,812 A | * | 1/1998 | Horn | C12N 15/101 435/252.3 |
| 10,808,241 B2 | * | 10/2020 | Abysalh | B01L 3/502753 |
| 2015/0376220 A1 | * | 12/2015 | DeRosa | C07H 21/00 536/23.1 |

FOREIGN PATENT DOCUMENTS

| WO | WO 2001/059098 A2 | 8/2001 |
|---|---|---|
| WO | WO 2014/152966 A1 | 9/2014 |
| WO | WO 2015/164773 A1 | 10/2015 |
| WO | WO 2018/157133 | 8/2018 |
| WO | WO 2019/207060 | 10/2019 |

OTHER PUBLICATIONS

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5, (2016).

International Search Report and Written Opinion for PCT/US2020/033185 dated Jul. 24, 2020.

Schmitz et al., "Purification of nucleic acids by selective precipitation with polyethylene glycol 6000", Analytical Biochemistry, Academic Press, Amsterdam, NL, vol. 354, No. 12, pp. 311-313, (2006).

* cited by examiner

*Primary Examiner* — David C Thomas
(74) *Attorney, Agent, or Firm* — Proskauer Rose LLP; Fangli Chen; Nicholas C. Prairie

(57) ABSTRACT

The present invention provides, among other things, methods for purifying high quality messenger RNA (mRNA) suitable for clinical use, without using any caustic or flammable solvents. The present invention is, in part, based on surprising discovery that mRNA can be successfully purified by selective precipitation and washing without using ethanol while maintaining integrity and high purity of mRNA. Thus, the present invention provides an effective, reliable, and safer method of purifying RNA from large scale manufacturing process therapeutic applications without using any caustic or inflammable solvents.

8 Claims, 19 Drawing Sheets

Gel Lane Assignment:
1. Faint Positive
2. CMS 1-62 FFLUC
3. RNase I
4. SP6 Polymerase
5. Guanylyl Transferase
6. MTEG 1:2.3:1- (2) 2.5mL 95% MTEG Wash
7. MTEG 1:2.3:1.7- (2) 2.5mL 95% MTEG Wash
8. MTEG 1:2.3:2- (2) 2.5mL 95% MTEG Wash
9. MTEG 1:2.3:2.5- (2) 2.5mL 95% MTEG Wash
10. Ethanol Control- (2) 80% 2mL Wash

METHODS FOR PURIFICATION OF MESSENGER RNA

CROSS-REFERENCE TO RELATED APPLICATIONS

This application claims priority to U.S. provisional patent application Ser. No. 62/848,412, filed May 15, 2019 and 62/891,781 filed on Aug. 26, 2019, each of which are hereby incorporated by reference in their entirety for all purposes.

BACKGROUND OF THE INVENTION

Messenger RNA (mRNA) therapy is becoming an increasingly important approach for the treatment of a variety of diseases. mRNA therapy involves administration of a drug product comprising in vitro transcribed (IVT) and highly pure messenger RNA (mRNA) into a patient in need of the therapy and production of the protein encoded by the mRNA within the patient's body. Thus, there is a need for efficient, large scale production of highly pure mRNA product suitable for therapeutic use.

Traditionally, mRNA generated from in vitro transcription is purified using commercially-available chromatography systems, e.g., HPLC, and/or by extraction into an organic mix (phenol:chloroform:isoamyl alcohol) and subsequent ethanol precipitation. However, use of column systems is expensive and challenging and the use of caustic or flammable solvents in extraction of mRNA can present safety and cost challenges, particularly in large-scale applications.

A safe and cost-effective method that produces highly pure mRNA that is acceptable for therapeutic use is currently lacking.

SUMMARY OF THE INVENTION

The present invention provides, among other things, a highly efficient and cost-effective method of purifying messenger RNA (mRNA). The present invention is, in part, based on the surprising discovery of a method of purifying mRNA using low amounts of volatile organic compounds or no volatile organic compounds and that yields mRNA of high integrity and high purity. Thus, in one aspect, the present invention provides an effective, reliable, and safer method of purifying mRNA which can be used for large-scale manufacturing process therapeutic applications without using any caustic or flammable solvents.

In some aspects, the present invention provides a method of purifying messenger RNA (mRNA) comprising a) precipitating the mRNA in a suspension comprising a high molar salt solution and an amphiphilic polymer to provide precipitated mRNA; b) capturing the precipitated mRNA; c) washing the precipitated mRNA captured in step b) with a wash solution to purify the precipitated mRNA; and d) solubilizing the precipitated mRNA from step c) with a solubilizing solution to obtain a purified mRNA composition.

In some embodiments, the purified mRNA composition is substantially free of contaminants comprising short abortive RNA species, long abortive RNA species, double-stranded RNA (dsRNA), residual plasmid DNA, residual in vitro transcription enzymes, residual solvent and/or residual salt. In some embodiments, the purified mRNA composition is substantially free of contaminants comprising short abortive RNA species. For example, the purified mRNA composition has less than about 1% short abortive RNA species. In some embodiments, the purified mRNA composition is substantially free of contaminants comprising long abortive RNA species. For example, the purified mRNA composition has no greater than about 55% long abortive/degraded species as determined by capillary gel electrophoresis (CGE). In some embodiments, the purified mRNA composition is substantially free of contaminants comprising double-stranded RNA (dsRNA). For example, the purified mRNA composition has less than 1% double-stranded RNA. In some embodiments, the purified mRNA composition is substantially free of contaminants comprising residual plasmid DNA. For example, the purified mRNA composition has 10 pg/mg or less of residual plasmid DNA. In some embodiments, the purified mRNA composition is substantially free of contaminants comprising residual in vitro transcription enzymes. For example, for every 15 µg of purified mRNA composition there is less than 0.3 ng of polymerase. For every 15 µg of purified mRNA composition there is less than 0.3 ng of cap enzymes. For every 15 µg of purified mRNA composition there is less than 0.3 ng of tail enzymes. In some embodiments, the purified mRNA composition is substantially free of contaminants comprising residual solvent. In some embodiments, the purified mRNA composition is substantially free of contaminants comprising residual salt.

In some embodiments, the purified mRNA comprises residual plasmid DNA of 10 pg/mg purified mRNA or less.

In some embodiments, the amphiphilic polymer in the suspension is selected from pluronics, polyvinyl pyrrolidone, polyvinyl alcohol, polyethylene glycol (PEG), polyethers such as polypropylene glycol (PPG) or polypropylene oxide, or combinations thereof. In some embodiments, the amphiphilic polymer in the suspension is pluronics. In some embodiments, the amphiphilic polymer in the suspension is polyvinyl pyrrolidone. In some embodiments, the amphiphilic polymer in the suspension is polyvinyl alcohol. In some embodiments, the amphiphilic polymer in the suspension is polyethylene glycol (PEG). In some embodiments, the amphiphilic polymer in the suspension is a polyether. In some embodiments, the amphiphilic polymer in the suspension is polypropylene glycol (PPG). In some embodiments, the amphiphilic polymer in the suspension is polypropylene oxide.

In some embodiments, the suspension does not comprise an organic solvent. In some embodiments, the amphiphilic polymer in the suspension is PEG. In some embodiments, the suspension does not comprise an organic solvent and the mRNA is precipitated using polyethylene glycol (PEG). In some embodiments, the suspension comprises PEG to precipitate the mRNA. In some embodiments, the suspension comprises PEG at about 10% to about 100% weight/volume concentration.

In some embodiments, the suspension comprises PEG at about 50% weight/volume concentration.

In some embodiments, the suspension comprises a final concentration of PEG at less than 25% weight/volume. In some embodiments, the suspension comprises a final concentration of PEG at about 5% to 20% weight/volume. In particular embodiments, the suspension comprises a final concentration of PEG at about 10% to 15% weight/volume, for example 12% weight/volume. In some embodiments, the molecular weight of the PEG is about 2000 to about 10000 g/mol. In some embodiments, the molecular weight of the PEG is about 4000 to about 8000 g/mol. In some embodiments, the molecular weight of the PEG is about 6000 g/mol (e.g. PEG-6000). As shown in the examples, a final concentration of PEG with a molecular weight of about 6000 g/mol (e.g. PEG-6000) in the suspension of about 12% weight/volume ensured effective purification and provided highly pure mRNA samples.

In some embodiments, the suspension does not comprise an organic solvent and does comprise triethylene glycol (TEG). In some embodiments, the suspension comprises TEG to precipitate the mRNA. In some embodiments, the suspension comprises TEG at about 10% to about 100% weight/volume concentration.

In some embodiments, the suspension comprises TEG at about 50% weight/volume concentration.

In some embodiments, the suspension does not comprise an organic solvent and does comprise triethylene glycol monomethyl ether (MTEG). In some embodiments, the suspension comprises MTEG to precipitate the mRNA. In some embodiments, the suspension comprises MTEG at about 10% to about 100% weight/volume concentration.

In some embodiments, the suspension comprises MTEG at about 50% weight/volume concentration.

In some embodiments, the suspension comprises MTEG at a final concentration of about 15% to about 45% weight/volume. In some embodiments, the suspension comprises MTEG at a final concentration of about 20% to about 40% weight/volume. In some embodiments, the suspension comprises MTEG at a final concentration of about 20% weight/volume. In some embodiments, the suspension comprises MTEG at a final concentration of about 25% weight/volume. In some embodiments, the suspension comprises MTEG at a final concentration of about 30% weight/volume. In some embodiments, the suspension comprises MTEG at a final concentration of about 35% weight/volume.

In some embodiments, the high molar salt solution comprises guanidinium thiocyanate (GSCN). In some embodiments, the GSCN is at a final concentration of about 2-4M. In some embodiments, the GSCN is at a final concentration of 2.5-3 M. In particular embodiments, the GSCN is at a final concentration of about 2.7 M.

In some embodiments, the amphiphilic polymer in the wash solution is selected from pluronics, polyvinyl pyrrolidone, polyvinyl alcohol, polyethylene glycol (PEG), polyethers such as polypropylene glycol (PPG) or polypropylene oxide, or combinations thereof. In some embodiments, the amphiphilic polymer in the wash solution is pluronics. In some embodiments, the amphiphilic polymer in the wash solution is polyvinyl pyrrolidone. In some embodiments, the amphiphilic polymer in the wash solution is polyvinyl alcohol. In some embodiments, the amphiphilic polymer in the wash solution is polyethylene glycol (PEG). In some embodiments, the amphiphilic polymer in the wash solution is a polyether. In some embodiments, the amphiphilic polymer in the wash solution is polypropylene glycol (PPG). In some embodiments, the amphiphilic polymer in the wash solution is polypropylene oxide.

In some embodiments, the wash solution does not comprise an organic solvent. In some embodiments, the wash solution does not comprise an organic solvent and comprises polyethylene glycol (PEG). In some embodiments, the PEG used in the wash solution has a viscosity of 90 centistrokes or less. In some embodiments, the PEG used in the wash solution has a viscosity of 80 centistrokes or less. In some embodiments, the PEG used in the wash solution has a viscosity of 70 centistrokes or less. In some embodiments, the PEG used in the wash solution has a viscosity of 60 centistrokes or less. In some embodiments, the PEG used in the wash solution has a viscosity of 50 centistrokes or less. In some embodiments, the PEG used in the wash solution has a viscosity of 40 centistrokes or less. In some embodiments, the PEG used in the wash solution has a viscosity of 30 centistrokes or less. In some embodiments, the PEG used in the wash solution has a viscosity of 20 centistrokes or less. In some embodiments, the PEG used in the wash solution has a viscosity of 10 centistrokes or less. A PEG suitable for use in the wash solution has a viscosity of about 90 centistrokes at 25° C., such as PEG-400. Accordingly, in a particular embodiment, the PEG used in the wash solution is PEG-400.

In some embodiments, the wash solution does not comprise an organic solvent and comprises triethylene glycol (TEG). In some embodiments, the solution comprises TEG.

In some embodiments, the wash solution does not comprise an organic solvent and comprises triethylene glycol monomethyl ether (MTEG). In some embodiments, the wash solution comprises MTEG. In some embodiments, MTEG is present in the wash solution at about 90% to about 100% by weight/volume concentration. In particular embodiments, MTEG is present in the wash solution at about 95% by weight/volume concentration.

As shown in the examples, MTEG is suitable for use in the wash solution, effectively washing the precipitated mRNA, while retaining it in precipitated form. MTEG has a viscosity of about 7 centistrokes at room temperature. MTEG therefore allows highly efficient purification and recovery of the mRNA irrespective of the process of purification used (e.g. flow filtration, depth filtration or centrifugation).

In some embodiments, the amphiphilic polymer in the wash solution is PEG. In a particular embodiment, the molecular weight of the PEG in the wash solution is about 200 g/mol to about 600 g/mol. In particular embodiments, the PEG in the wash solution has a molecular weight of about 400 g/mol (for example PEG-400).

In some embodiments, PEG is present in the wash solution at about 10% to about 100% weight/volume concentration.

In some embodiments, PEG is present in the wash solution at about 50 to about 90% weight/volume concentration. In some embodiments, PEG is present in the wash solution at about 90% to about 100% weight/volume concentration.

In some embodiments, the PEG is present in the wash solution at about 90% weight/volume concentration. In particular embodiments, the PEG in the wash solution has a molecular weight of about 400 g/mol (for example PEG-400). In some embodiments, the PEG in the wash solution has a molecular weight of about 400 g/mol (for example PEG-400) and is at about 90% to about 100% weight/volume concentration. In particular embodiments, the PEG in the wash solution has a molecular weight of about 400 g/mol (for example PEG-400) and is present in the wash solution at about 90% weight/volume concentration.

In some embodiments, the molecular weight of PEG in the suspension is about 200 to about 40,000 g/mol. In some embodiments, the molecular weight of PEG in the wash solution is about 200 to about 40,000 g/mol. In some embodiments, the molecular weight of PEG both in the suspension and the wash solution is about 200 to about 40,000 g/mol. In particular embodiments, the molecular weight of PEG in the suspension is about 2,000 g/mol to about 10,000 g/mol and the molecular weight of PEG in the wash solution is about 200 g/mol to about 600 g/mol. In a specific embodiment, the PEG in the suspension is PEG-6000 and the PEG in the wash solution is PEG-400.

In some embodiments, the PEG in the suspension is linear. In some embodiments, the PEG in the suspension is branched. In some embodiments, the PEG in the suspension is Y-shaped. In some embodiments, the PEG in the suspension is of multi-arm configuration.

In some embodiments, the PEG in the wash solution is linear. In some embodiments, the PEG in the wash solution is branched. In some embodiments, the PEG in the wash solution is Y-shaped. In some embodiments, the PEG in the wash solution is of multi-arm configuration.

In some embodiments, the PEG both in the suspension and in the wash solution is linear. In some embodiments, the PEG both in the suspension and in the wash solution is branched. In some embodiments, the PEG both in the suspension and in the wash solution is Y-shaped. In some embodiments, the PEG both in the suspension and in the wash solution is of multi-arm configuration.

In some embodiments, the suspension comprises a PEG selected from triethylene glycol, tetraethylene glycol, PEG 200, PEG 300, PEG 400, PEG 600, PEG 1,000, PEG 1,500, PEG 2,000, PEG 3,000, PEG 3,350, PEG 4,000, PEG 6,000, PEG 8,000, PEG 10,000, PEG 20,000, PEG 35,000, and PEG 40,000. In some embodiments, the suspension comprises triethylene glycol. In some embodiments, the suspension comprises tetraethylene glycol. In some embodiments, the suspension comprises PEG 200. In some embodiments, the suspension comprises PEG 300. In some embodiments, the suspension comprises PEG 400. In some embodiments, the suspension comprises PEG 600. In some embodiments, the suspension comprises PEG 1,000. In some embodiments, the suspension comprises PEG 1,500. In some embodiments, the suspension comprises PEG 2,000. In some embodiments, the suspension comprises PEG 3,000. In some embodiments, the suspension comprises PEG 3,350. In some embodiments, the suspension comprises PEG 4,000. In some embodiments, the suspension comprises PEG 6,000. In some embodiments, the suspension comprises PEG 8,000. In some embodiments, the suspension comprises PEG 10,000. In some embodiments, the suspension comprises PEG 20,000. In some embodiments, the suspension comprises PEG 35,000. In some embodiments, the suspension comprises PEG 40,000.

In some embodiments, the suspension comprises PEG 6,000.

In some embodiments, the suspension does not comprise PEG 6,000.

In some embodiments, the suspension is PEG 400.

In some embodiments, the suspension is PEG 150.

In some embodiments, the suspension comprises a mixture of one or more PEG polymers.

In some embodiments, the mixture of PEG polymers in the suspension comprises polymers having distinct molecular weights.

In some embodiments, the mixture of PEG polymers in the suspension comprises polymers having distinct geometrical configurations.

In some embodiments, the suspension is aqueous.

In some embodiments, the suspension has volatile organic compounds comprising less than about 50% of total volume of the suspension. For example, in some embodiments, the suspension has volatile organic compounds comprising less than about 50%, 45%, 40%, 35%, 30%, 25%, 20%, 15%, 10%, 5%, 2%, 1%, 0.5%, 0.01% of the total volume of the suspension. Accordingly, in some embodiments, the suspension has volatile organic compounds comprising less than about 50% of the total volume of the suspension. In some embodiments, the suspension has volatile organic compounds comprising less than 45% of the total volume of the suspension. In some embodiments, the suspension has volatile organic compounds comprising less than 40% of the total volume of the suspension. In some embodiments, the suspension has volatile organic compounds comprising less than 35% of the total volume of the suspension. In some embodiments, the suspension has volatile organic compounds comprising less than 30% of the total volume of the suspension. In some embodiments, the suspension has volatile organic compounds comprising less than 25% of the total volume of the suspension. In some embodiments, the suspension has volatile organic compounds comprising less than 20% of the total volume of the suspension. In some embodiments, the suspension has volatile organic compounds comprising less than 15% of the total volume of the suspension. In some embodiments, the suspension has volatile organic compounds comprising less than 10% of the total volume of the suspension. In some embodiments, the suspension has volatile organic compounds comprising less than 5% of the total volume of the suspension. In some embodiments, the suspension has volatile organic compounds comprising less than 2% of the total volume of the suspension. In some embodiments, the suspension has volatile organic compounds comprising less than 1% of the total volume of the suspension. In some embodiments, the suspension has volatile organic compounds comprising less than 0.5% of the total volume of the suspension. In some embodiments, the suspension has volatile organic compounds comprising less than 0.1% of the total volume of the suspension. Many volatile organic compounds are known in the art and include, for example, ethanol, isopropyl alcohol, and benzyl alcohol.

In some embodiments, the suspension is free of volatile organic compounds.

In some embodiments, the suspension is free of alcohol.

In some embodiments, the suspension is free of ethanol. In some embodiments, the suspension is free of isopropyl alcohol. In some embodiments, the suspension is free of benzyl alcohol.

In some embodiments, the suspension comprises a non-aqueous component. In some embodiments, the non-aqueous component of the suspension is ethanol. In some embodiments, the non-aqueous component of the suspension is isopropyl alcohol. In some embodiments, the non-aqueous component of the suspension is benzyl alcohol.

In some embodiments, the wash solution comprises a PEG selected from triethylene glycol, tetraethylene glycol, PEG 200, PEG 300, PEG 400, PEG 600, PEG 1,000, PEG 1,500, PEG 2,000, PEG 3,000, PEG 3,350, PEG 4,000, PEG 6,000, PEG 8,000, PEG 10,000, PEG 20,000, PEG 35,000, and PEG 40,000. In some embodiments, the wash solution comprises triethylene glycol. In some embodiments, the wash solution comprises tetraethylene glycol. In some embodiments, the wash solution comprises PEG 200. In some embodiments, the wash solution comprises PEG 300. In some embodiments, the wash solution comprises PEG 400. In some embodiments, the wash solution comprises PEG 600. In some embodiments, the wash solution comprises PEG 1,000. In some embodiments, the wash solution comprises PEG 1,500. In some embodiments, the wash solution comprises PEG 2,000. In some embodiments, the wash solution comprises PEG 3,000. In some embodiments, the wash solution comprises PEG 3,350. In some embodiments, the wash solution comprises PEG 4,000. In some embodiments, the wash solution comprises PEG 6,000. In some embodiments, the wash solution comprises PEG 8,000. In some embodiments, the wash solution comprises PEG 10,000. In some embodiments, the wash solution comprises PEG 20,000. In some embodiments, the wash solution comprises PEG 35,000. In some embodiments, the wash solution comprises PEG 40,000.

In some embodiments, the wash solution comprises PEG 6,000.

In some embodiments, the wash solution does not comprise PEG 6,000.

In some embodiments, the wash solution is PEG 400.

In some embodiments, the wash solution comprises a mixture of one or more PEG polymers.

In some embodiments, the mixture of PEG polymers in the wash solution comprises polymers having distinct molecular weights.

In some embodiments, the mixture of PEG polymers in the wash solution comprises polymers having distinct geometrical configurations.

In some embodiments, the wash solution is aqueous.

In some embodiments, the wash solution is free of volatile organic compounds.

In some embodiments, the wash solution is free of alcohol.

In some embodiments, the wash solution has volatile organic compounds comprising less than about 50% of total volume of the wash solution. For example, in some embodiments, the wash solution has volatile organic compounds comprising less than about 50%, 45%, 40%, 35%, 30%, 25%, 20%, 15%, 10%, 5%, 2%, 1%, 0.5%, 0.01% of the total volume of the wash solution. Accordingly, in some embodiments, the wash solution has volatile organic compounds comprising less than about 50% of the total volume of the wash solution. In some embodiments, the wash solution has volatile organic compounds comprising less than 45% of the total volume of the wash solution. In some embodiments, the wash solution has volatile organic compounds comprising less than 40% of the total volume of the wash solution. In some embodiments, the wash solution has volatile organic compounds comprising less than 35% of the total volume of the wash solution. In some embodiments, the wash solution has volatile organic compounds comprising less than 30% of the total volume of the wash solution. In some embodiments, the wash solution has volatile organic compounds comprising less than 25% of the total volume of the wash solution. In some embodiments, the wash solution has volatile organic compounds comprising less than 20% of the total volume of the wash solution. In some embodiments, the wash solution has volatile organic compounds comprising less than 15% of the total volume of the wash solution. In some embodiments, the wash solution has volatile organic compounds comprising less than 10% of the total volume of the wash solution. In some embodiments, the wash solution has volatile organic compounds comprising less than 5% of the total volume of the wash solution. In some embodiments, the wash solution has volatile organic compounds comprising less than 2% of the total volume of the wash solution. In some embodiments, the wash solution has volatile organic compounds comprising less than 1% of the total volume of the wash solution. In some embodiments, the wash solution has volatile organic compounds comprising less than 0.5% of the total volume of the wash solution. In some embodiments, the wash solution has volatile organic compounds comprising less than 0.1% of the total volume of the wash solution. Many volatile organic compounds are known in the art and include, for example, ethanol, isopropyl alcohol, and benzyl alcohol.

In some embodiments, the wash solution is free of ethanol. In some embodiments, the wash solution is free of isopropyl alcohol. In some embodiments, the wash solution is free of benzyl alcohol.

In some embodiments, the wash solution comprises a non-aqueous component. In some embodiments, the non-aqueous component of the wash solution is ethanol. In some embodiments, the non-aqueous component of the wash solution is isopropyl alcohol. In some embodiments, the non-aqueous component of the wash solution is benzyl alcohol.

In some embodiments, both the suspension and the wash buffer are aqueous. In some embodiments, both the suspension and the wash buffer comprise PEG. In some embodiments, both the suspension and the wash buffer are aqueous and comprise the same PEG. In some embodiments, both the suspension and the wash buffer are aqueous and the suspension comprises a first PEG and the wash buffer comprises a second PEG that is different from the first PEG. In some embodiments, the molecular weight of the PEG in the suspension is about 2000 to about 10000 g/mol and the molecular weight of the PEG in the wash buffer is about 200-600 g/mol. In some embodiments, the molecular weight of the PEG in the suspension is about 4000 to about 8000 g/mol and the molecular weight of the PEG in the wash buffer is about 300-500 g/mol. In some embodiments, the molecular weight of the PEG in the suspension is about 6000 g/mol (e.g. PEG-6000) and the molecular weight of the PEG in the wash buffer is about 400 g/mol (e.g. PEG-400).

In some embodiments, the capturing the precipitated mRNA occurs on a filter. In some embodiments, the filter is selected from a microfiltration or ultrafiltration filter. In some embodiments, the microfiltration filter has a pore size of between 0.05 µm and 1.0 µm. For example, in some embodiments, the microfiltration filter has a pore size of 0.05 µm, 0.10 µm, 0.20 µm, 0.3 µm. 0.4 µm, 0.5 µm. 0.6 µm, 0.7 µm, 0.8 µm, 0.9 µm, or 1.0 µm. Accordingly, in some embodiments, the microfiltration filter has a pore size of 0.05 µm. In some embodiments, the microfiltration filter has a pore size of 0.10 µm. In some embodiments, the microfiltration filter has a pore size of 0.20 µm. In some embodiments, the microfiltration filter has a pore size of 0.30 µm. In some embodiments, the microfiltration filter has a pore size of 0.40 µm. In some embodiments, the microfiltration filter has a pore size of 0.50 µm. In some embodiments, the microfiltration filter has a pore size of 0.60 µm. In some embodiments, the microfiltration filter has a pore size of 0.70 µm. In some embodiments, the microfiltration filter has a pore size of 0.80 µm. In some embodiments, the microfiltration filter has a pore size of 0.90 µm. In some embodiments, the microfiltration filter has a pore size of 1.0 µm.

In some embodiments, the filter will have a nominal molecular weight limit (NMWL) of between 100 kDa and 1,000 kDa. In some embodiments, the filter will have a NMWL of between 200 kDa and 700 kDa. In some embodiments, the filter will have a NMWL between 200 kDa and 500 kDa. In some embodiments, the filter has a NMWL of 300 kDa. In some embodiments, the filter has a NMWL of 500 kDa.

In some embodiments, the microfiltration filter has a nominal molecular weight limit (NMWL) of greater than 1,000 kilodaltons (kDa). In some embodiments, the ultrafiltration filter has a pore size of less than 0.05 µm. In some embodiments, the ultrafiltration filter has an NMWL of between about 1 kDa and 1,000 kDA. For example, in some embodiments, the ultrafiltration filter has an NMWL of 1 kDA, 5 kDA, 10 kDA, 15 kDA, 20 kDA, 25 kDA, 50 kDA, 100 kDA, 150 kDA, 200 kDA, 250 kDA, 300 kDA, 350 kDA, 400 kDA, 450 kDA, 500 kDA, 550 kDA, 600 kDA, 650 kDA, 700 kDA, 750 kDA, 800 kDA, 850 kDA, 900 kDA, 950 kDA, or 1,000 kDA. Accordingly, in some embodiments, the ultrafiltration filter has an NMWL of 1 kDA. In some embodiments, the ultrafiltration filter has an NMWL of 5 kDA. In some embodiments, the ultrafiltration filter has an NMWL of 10 kDA. In some embodiments, the ultrafiltration filter has an NMWL of 15 kDA. In some embodiments, the ultrafiltration filter has an NMWL of 20 kDA. In some embodiments, the ultrafiltration filter has an NMWL of 25 kDA. In some embodiments, the ultrafiltration filter has an NMWL of 50 kDA. In some embodiments, the ultrafiltration filter has an NMWL of 100 kDA. In some embodiments, the ultrafiltration filter has an NMWL of 150 kDA. In some embodiments, the ultrafiltration filter has an NMWL of 200 kDA. In some embodiments, the ultrafiltration filter has an NMWL of 250 kDA. In some embodiments, the ultrafiltration filter has an NMWL of 300 kDA. In some embodiments, the ultrafiltration filter has an NMWL of 350 kDA. In some embodiments, the ultrafiltration filter has an NMWL of 400 kDA. In some embodiments, the ultrafiltration filter has an NMWL of 450 kDA. In some embodiments, the ultrafiltration filter has an NMWL of 500 kDA. In some embodiments, the ultrafiltration filter has an NMWL of 550 kDA. In some embodiments, the ultrafiltration filter has an NMWL of 600 kDA. In some embodiments, the ultrafiltration filter has an NMWL of 650 kDA. In some embodiments, the ultrafiltration filter has an NMWL of 700 kDA. In some embodiments, the ultrafiltration filter has an NMWL of 750 kDA. In some embodiments, the ultrafiltration filter has an NMWL of 800 kDA. In some embodiments, the ultrafiltration filter has an NMWL of 850 kDA. In some embodiments, the ultrafiltration filter has an NMWL of 900 kDA. In some embodiments, the ultrafiltration filter has an NMWL of 950 kDA. In some embodiments, the ultrafiltration filter has an NMWL of 1,000 kDA.

In some embodiments, tangential flow filtration (TFF) or diafiltration is used to purify the precipitated mRNA in step c). Accordingly, in some embodiments, TFF is used to purify the precipitated mRNA in step c). In some embodiments, diafiltration is used to purify the precipitated mRNA in step c).

In some embodiments, a filter aid is used.

In some embodiments, the filter aid is cellulose-based. In particular embodiments, the cellulose-based filter aid is added to the suspension at a mass ratio of precipitated mRNA to filter aid of 1:10. In some embodiments, the cellulose-based filter aid comprises purified cellulose fibres of about 5 to about 500 µm in length. In some embodiments, the cellulose fibres are of about 10 to about 100 µm in length. In some embodiments, the cellulose fibres are about 20 µm, 30 µm, 40 µm or 50 µm in length. In particular embodiments, the cellulose-based filter aid comprises purified cellulose fibres of about 20 µm in length (e.g. Solka-Floc® or Sigmacell Cellulose 20).

In some embodiments, the filter aid comprises diatomaceous earth, and/or volcanic ash. In some embodiments, the filter aid comprises diatomaceous earth. In some embodiments, the filter aid comprises volcanic ash. In some embodiments, the filter aid comprises diatomaceous earth and volcanic ash.

In some embodiments, the solubilizing solution is selected from water, Tris-EDTA (TE), sodium citrate, or combinations thereof. In some embodiments, the solubilizing solution is water. In some embodiments the solubilizing solution is TE. In some embodiments, the solubilizing solution is sodium citrate.

In some embodiments, yield of the purified mRNA is about 50% to about 100%.

In some embodiments, the yield of the purified mRNA is about 70% to about 99%.

In some embodiments, the yield of the purified mRNA is between about 90 and about 99%. In particular embodiments, the yield of the purified mRNA is more than about 93%, e.g., more than about 94%, particularly more than about 95%.

In some embodiments, purity of the purified mRNA is between about 60% and about 100%.

In some embodiments, the purity of the purified mRNA is between about 80% and 99%.

In some embodiments, the purity of the purified mRNA is between about 90% and about 99%.

In some embodiments, the method does not comprise a chromatography step.

In some embodiments, the precipitated mRNA is centrifuged to obtain an mRNA pellet.

In some embodiments, the mRNA pellet is resuspended in a buffer solution.

In some embodiments, the buffer solution is selected from water, TE, sodium citrate, or combinations thereof. In some embodiments, the buffer solution is water. In some embodiments the buffer solution is TE. In some embodiments, the buffer solution is sodium citrate.

In some embodiments, the precipitated mRNA comprises at least 100 mg, 1 g, 10 g, 100 g, 1 kg, 10 kg, 100 kg, one metric ton, or ten metric tons, of mRNA or any amount there between. Accordingly, in some embodiments, the precipitated mRNA comprises at least 100 mg. In some embodiments, the precipitated mRNA comprises at least 1 g. In some embodiments, the precipitated mRNA comprises at least 10 g. In some embodiments, the precipitated mRNA comprises at least 100 g. In some embodiments, the precipitated mRNA comprises at least 1 kg. In some embodiments, the precipitated mRNA comprises at least 10 kg. In some embodiments, the precipitated mRNA comprises at least 100 kg. In some embodiments, the precipitated mRNA comprises at least one metric ton. In some embodiments, the precipitated mRNA comprises at least ten metric tons.

In some embodiments, the precipitated mRNA comprises greater than 1 kg of mRNA.

In some embodiments, the method is ethanol free.

In some aspects, the present invention provides a method of purifying messenger RNA (mRNA) comprising: a) precipitating the mRNA in a guanidinium thiocyanate (GSCN) solution comprising PEG; b) centrifuging the solution to create an mRNA pellet; c) resuspending the mRNA pellet in a buffer; d) capturing the mRNA on a filter; e) washing the mRNA of step d) with a PEG solution; and f) solubilizing the washed mRNA to obtain an mRNA composition substantially free of contaminants.

In some aspect, the invention provides a method of manufacturing mRNA comprising the steps of (a) performing in vitro transcription (IVT) by mixing (i) a DNA template comprising a promoter and (ii) an RNA polymerase, to generate an impure preparation comprising full-length mRNA; (b) providing high molar salt and an amphiphilic polymer to the suspension to precipitate full-length mRNA and provide precipitated full-length mRNA in the suspension; (c) capturing the precipitated full-length mRNA by applying the suspension to a filter; and (d) washing the precipitated full-length mRNA of step (c) with an aqueous solvent to obtain a purified full-length mRNA in an aqueous solution, and (e) solubilizing the precipitated mRNA from step (d) to obtain a purified mRNA composition, wherein the purified full-length mRNA in the aqueous solution provided from step (d) is substantially free of (i) the DNA template comprising a promoter and the (ii) the RNA polymerase.

In some embodiments, in step (a) the RNA polymerase is SP6 polymerase.

In some embodiments, the purified full-length mRNA in the aqueous solution provided from step (e) is also substantially free of (v) double-stranded RNA (dsRNA).

In some embodiments, the suspension comprises PEG of a molecular weight around 6000 g/mol (e.g. PEG-6000) at a final concentration of between about 5% and 20% weight/volume concentration and GSCN at a final concentration of about 2-4M. In particular embodiments, the suspension comprises PEG of a molecular weight around 6000 g/mol (e.g. PEG-6000) at a final concentration of about 10%, 11%, 12%, 13%, 14% or 15% weight/volume concentration and GSCN at a final concentration of about 2.5-3 M. As shown in the examples below, polymer-induced precipitation with a final concentration of PEG in the suspension of less than 20% resulted in highly pure mRNA samples after purification. Furthermore, a final concentration of PEG in the suspension of about 12% (for example a ratio of 1 of 50% PEG-6000) and a final GSCN concentration of 2.7M achieved highly effective purification of mRNA.

In some embodiments, MTEG can be used in place of PEG to provide a suspension of precipitated mRNA. In particular embodiments, MTEG is used for this purpose at a final concentration of about 15% to about 45% weight/volume. In some embodiments, the suspension comprises MTEG at a final concentration of about 20% to about 40% weight/volume. In some embodiments, the suspension comprises MTEG at a final concentration of about 20% weight/volume. In some embodiments, the suspension comprises MTEG at a final concentration of about 25% weight/volume. In some embodiments, the suspension comprises MTEG at a final concentration of about 30% weight/volume. In some embodiments, the suspension comprises MTEG at a final concentration of about 35% weight/volume. In some embodiments, the suspension comprises MTEG at a final concentration of less than 35% weight/volume. The rest of the conditions used in MTEG-induced precipitation are the same as those used in the PEG-induced precipitation. As shown in the examples, a suspension comprising mRNA, GSCN and MTEG, with MTEG at a final concentration of less than 35% weight/volume ensured efficient recovery of mRNA without unwanted precipitation of process enzymes. Particularly suitable for efficient recovery of mRNA without unwanted precipitation of process enzymes is a suspension comprising mRNA, GSCN and MTEG, with MTEG at a final concentration of about 25%, in addition to a filter aid (for example cellulose-based filtering aid) at a mass ratio with the precipitated mRNA of about 10:1.

BRIEF DESCRIPTION OF THE DRAWING

The following figures are for illustration purposes only and not for limitation.

DEFINITIONS

Figure 1:
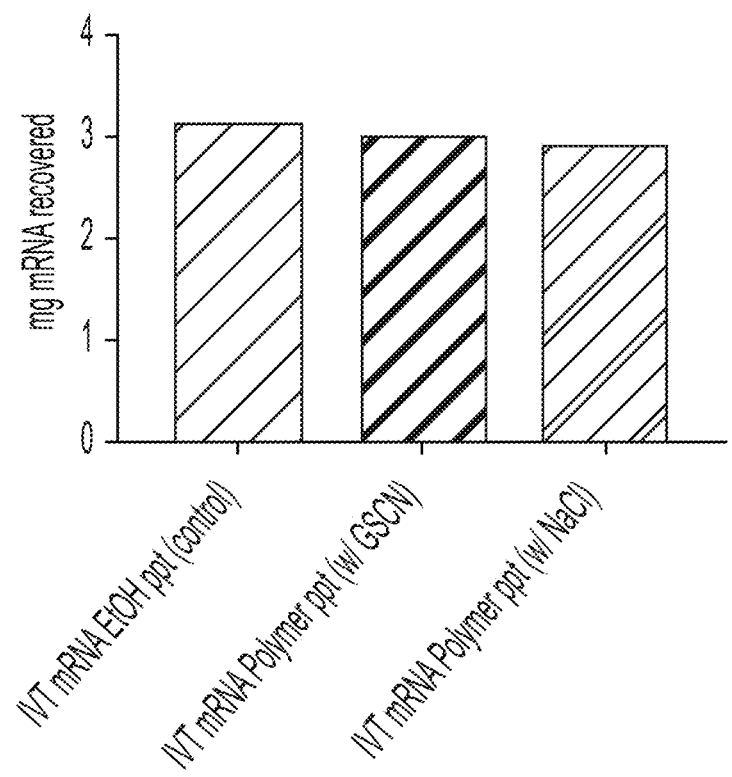
FIG. 1 shows the yield of mRNA purified with different precipitation conditions from 5 mg of IVT reactions.

In order for the present invention to be more readily understood, certain terms are first defined below. Additional definitions for the following terms and other terms are set forth throughout the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Approximately or about: As used herein, the term "approximately" or "about," as applied to one or more values of interest, refers to a value that is similar to a stated reference value. In certain embodiments, the term "approximately" or "about" refers to be within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein are modified by the term "approximately" or "about".

Batch: As used herein, the term "batch" refers to a quantity or amount of mRNA purified at one time, e.g., purified according to a single manufacturing order during the same cycle of manufacture. A batch may refer to an amount of mRNA purified in one reaction.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Comprising: As used herein, the term "comprising," or variations such as "comprises" or "comprising," will be understood to imply the inclusion of a stated element, integer or step, or group of elements, integers or steps, but not the exclusion of any other element, integer or step, or group of elements, integers or steps.

dsRNA: As used herein, the term "dsRNA" refers to the production of complementary RNA sequences during an in vitro transcription (IVT) reaction. Complimentary RNA sequences can be produced for a variety of reasons including, for example, short abortive transcripts that can hybridize to complimentary sequences in the nascent RNA strand, short abortive transcripts acting as primers for RNA dependent DNA independent RNA transcription, and possible RNA polymerase template reversal.

Expression: As used herein, "expression" of a nucleic acid sequence refers to translation of an mRNA into a polypeptide (e.g., heavy chain or light chain of antibody), assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalent, are used inter-changeably.

Functional: As used herein, a "functional" biological molecule is a biological molecule in a form in which it exhibits a property and/or activity by which it is characterized.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as "contaminants."

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions.

mRNA integrity: As used herein, the term "mRNA integrity" generally refers to the quality of mRNA. In some embodiments, mRNA integrity refers to the percentage of mRNA that is not degraded after a purification process. mRNA integrity may be determined using methods well known in the art, for example, by RNA agarose gel electrophoresis (e.g., Ausubel et al., John Weley & Sons, Inc., 1997, Current Protocols in Molecular Biology).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Precipitation: As used herein, the term "precipitation" (or any grammatical equivalent thereof) refers to the formation of a solid in a solution. When used in connection with mRNA, the term "precipitation" refers to the formation of insoluble or solid form of mRNA in a liquid.

Prematurely aborted RNA sequences: The terms "prematurely aborted RNA sequences", "short abortive RNA species", "shortmers", and "long abortive RNA species" as used herein, refers to incomplete products of an mRNA synthesis reaction (e.g., an in vitro synthesis reaction). For a variety of reasons, RNA polymerases do not always complete transcription of a DNA template; e.g., RNA synthesis terminates prematurely. Possible causes of premature termination of RNA synthesis include quality of the DNA template, polymerase terminator sequences for a particular polymerase present in the template, degraded buffers, temperature, depletion of ribonucleotides, and mRNA secondary structures. Prematurely aborted RNA sequences may be any length that is less than the intended length of the desired transcriptional product. For example, prematurely aborted mRNA sequences may be less than 1000 bases, less than 500 bases, less than 100 bases, less than 50 bases, less than 40 bases, less than 30 bases, less than 20 bases, less than 15 bases, less than 10 bases or fewer.

Salt: As used herein the term "salt" refers to an ionic compound that does or may result from a neutralization reaction between an acid and a base.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially free: As used herein, the term "substantially free" refers to a state in which relatively little or no amount of a substance to be removed (e.g., prematurely aborted RNA sequences) are present. For example, "substantially free of prematurely aborted RNA sequences" means the prematurely aborted RNA sequences are present at a level less than approximately 5%, 4%, 3%, 2%, 1.0%, 0.9%, 0.8%, 0.7%, 0.6%, 0.5%, 0.4%, 0.3%, 0.2%, 0.1% or less (w/w) of the impurity. Alternatively, "substantially free of prematurely aborted RNA sequences" means the prematurely aborted RNA sequences are present at a level less than about 100 ng, 90 ng, 80 ng, 70 ng, 60 ng, 50 ng, 40 ng, 30 ng, 20 ng, 10 ng, 1 ng, 500 pg, 100 pg, 50 pg, 10 pg, or less.

Unless otherwise defined, all technical and scientific terms used herein have the same meaning as commonly understood by one of ordinary skill in the art to which this application belongs and as commonly used in the art to which this application belongs; such art is incorporated by reference in its entirety. In the case of conflict, the present Specification, including definitions, will control.

DETAILED DESCRIPTION

The present invention provides, among other things, improved methods for purifying mRNA without the use of alcohols in the purification process.

Various aspects of the invention are described in detail in the following sections. The use of sections is not meant to limit the invention. Each section can apply to any aspect of the invention. In this application, the use of "or" means "and/or" unless stated otherwise.

Methods of Purification

Use of caustic or flammable solvents in purifying mRNA can present safety and cost challenges, particularly in large-scale preparations. The present invention relates to methods of purifying mRNA without using caustic or flammable solvents. The methods provided herein allow for efficient capture, wash, and high-yield isolation of mRNA manufactured at a scale capable of meeting most clinical and commercial needs. Accordingly, this disclosure provides a path forward for mRNA replacement therapeutics, allowing it to become a viable and successful alternative to the more traditional enzyme replacement therapies and biotherapeutics that are currently available.

To become a viable and successful alternative, a method for mRNA purification needs to be safe, cost-effective, robust and scalable to ensure large-scale manufacturing capabilities are in place to meet all clinical and commercial needs. An appropriate mRNA purification method is safe, cost-effective, and easily scalable while also providing an equivalent or better product when compared to currently-available industry-standard mRNA purification methods. In particular, the methods provided herein eliminates the use of caustic or flammable solvents, and results in high post-purification mRNA yields, maintenance of post purification mRNA integrity, and removal of process-related contaminants (e.g., prematurely aborted RNA sequences (short abortive RNA species or "shortmers"), long abortive RNA species, double-stranded RNA (dsRNA), plasmid DNA, residual solvent, residual salt, and residual in vitro transcription enzymes).

The methods provided herein are usable at a wide-range of scales. For example, and as discussed further herein, the methods provided allow for purification at various scales such as at or below 100 mg to greater than 1 kg. Moreover, data provided herein show that the present invention is a capable (and a lower cost) alternative to currently-available methods which rely on the use of flammable solvents such as alcohols for the purification of mRNA. The mRNA purification method provided herein is suitable for various uses, including, for example experimental, clinical, or commercial use. Furthermore, the present invention has a significant added benefit of scalability which is unavailable with industry-standard methods and kits. Finally, the herein-disclosed methods are extremely cost-effective relative to current processes such as filtration methods that include alcohol solvents and/or chromatography. See, e.g., WO 2011/068810; WO 2012/075040; WO 2014/152659; WO 2014/152673; WO 2014/152966; WO 2015/164773; WO 2016/004318; U.S. 62/420,413; and PCT/US16/57044.

Accordingly, the methods described herein are advantageous for the purification of mRNA, including large-scale quantities of mRNA (e.g., any batch size or loading volume described herein). The purification methods as described can provide mRNA having a high level of integrity and purity acceptable for therapeutic uses, and with minimal loss of full-length mRNA on account of the purification.

The method of purifying mRNA described herein comprises precipitating the mRNA, capturing the precipitated mRNA, and washing the captured, precipitated mRNA to obtain a purified mRNA composition substantially free of contaminants. Each of these steps is described in detail in the sections that follow.

Precipitation of mRNA

The method of purifying mRNA includes the steps of precipitating mRNA in a suspension comprising a high molar salt solution and an amphiphilic polymer, capturing the mRNA and washing the mRNA, thereby obtaining the mRNA substantially free of contaminants.

Methods described herein are suitable for the purification of mRNA in a provided suspension comprising mRNA (e.g., an in vitro synthesis reaction mixture). The suspension can have various contaminants, for example, plasmid DNA and enzymes.

In one embodiment, a salt (e.g., a chaotropic salt such as guanidine thiocyanate (GSCN)) is added to an mRNA-containing suspension to denature and solubilize contaminating proteins. Accordingly, in one embodiment, GSCN is in the high molar solution in the suspension. This is followed by the addition of an amphiphilic polymer to selectively precipitate mRNA. After mRNA precipitation, the resulting precipitated mRNA is captured using a filter or membrane and washed to yield a precipitate that is free of contamination, e.g., short abortive RNA species, long abortive RNA species, dsRNA, plasmid DNA, residual in vitro transcription enzymes, residual salt, and residual solvent. Subsequent dissolution of the precipitated mRNA by water yields purified mRNA composition.

In some embodiments, one agent that promotes precipitation of mRNA comprises guanidine thiocyanate (e.g., a solution comprising about 1-5M guanidine thiocyanate). For example, the solution comprises about 1M, 1.5M, 2.0M, 2.5M, 3.0M, 3.5M, 4.0M, 4.5M, or about 5M GSCN. Examples of suitable GSCN buffers include, for example, an aqueous solution comprising 4M guanidine thiocyanate, 25 mM sodium citrate pH 6.5, 0.5% N-lauroylsarcosine sodium salt. A further example of a GSCN buffer is an aqueous solution comprising 5M GSCN in a 10 mM dithiothreitol (DTT) buffer. In some embodiments, GSCN is at a final concentration of 2-4M. In some embodiments, the GSCN (for example 5M GSCN-10 mM DTT buffer) is at a final concentration of 2.5-3 M. In particular embodiments, GSCN is at a final concentration of about 2.7M.

Many amphiphilic polymers are known in the art. In some embodiments, amphiphilic polymer used in the methods herein include pluronics, polyvinyl pyrrolidone, polyvinyl alcohol, polyethylene glycol (PEG), or combinations thereof. In some embodiments, the amphiphilic polymer is selected from one or more of the following: PEG triethylene glycol, tetraethylene glycol, PEG 200, PEG 300, PEG 400, PEG 600, PEG 1,000, PEG 1,500, PEG 2,000, PEG 3,000, PEG 3,350, PEG 4,000, PEG 6,000, PEG 8,000, PEG 10,000, PEG 20,000, PEG 35,000, and PEG 40,000, or combination thereof. In some embodiments, the amphiphilic polymer comprises a mixture of two or more kinds of molecular weight PEG polymers are used. For example, in some embodiments, two, three, four, five, six, seven, eight, nine, ten, eleven, or twelve molecular weight PEG polymers comprise the amphiphilic polymer. Accordingly, in some embodiments, the PEG solution comprises a mixture of one or more PEG polymers. In some embodiments, the mixture of PEG polymers comprises polymers having distinct molecular weights.

In some embodiments, precipitating the mRNA in a suspension comprises one or more amphiphilic polymers. In some embodiments, the precipitating the mRNA in a suspension comprises a PEG polymer. Various kinds of PEG polymers are recognized in the art, some of which have distinct geometrical configurations. PEG polymers suitable for the methods herein include, for example, PEG polymers having linear, branched, Y-shaped, or multi-arm configuration. In some embodiments, the PEG is in a suspension comprising one or more PEG of distinct geometrical configurations. In some embodiments, precipitating mRNA can be achieved using PEG-6000 to precipitate the mRNA. In some embodiments, precipitating mRNA can be achieved using PEG-400 to precipitate the mRNA. In some embodiments, precipitating mRNA can be achieved using triethylene glycol (TEG) to precipitate the mRNA. In some embodiments, precipitating mRNA can be achieved using triethylene glycol monomethyl ether (MTEG) to precipitate the mRNA. In some embodiments, precipitating mRNA can be achieved using tert-butyl-TEG-O-propionate to precipitate the mRNA. In some embodiments, precipitating mRNA can be achieved using TEG-dimethacrylate to precipitate the mRNA. In some embodiments, precipitating mRNA can be achieved using TEG-dimethyl ether to precipitate the mRNA. In some embodiments, precipitating mRNA can be achieved using TEG-divinyl ether to precipitate the mRNA. In some embodiments, precipitating mRNA can be achieved using TEG-monobutyl ether to precipitate the mRNA. In some embodiments, precipitating mRNA can be achieved using TEG-methyl ether methacrylate to precipitate the mRNA. In some embodiments, precipitating mRNA can be achieved using TEG-monodecyl ether to precipitate the mRNA. In some embodiments, precipitating mRNA can be achieved using TEG-dibenzoate to precipitate the mRNA. Any one of these PEG or TEG based reagents can be used in combination with guanidinium thiocyanate to precipitate the mRNA. The structures of each of these reagents is shown below in Table A.

TABLE A

| Non-Organic Solvent Reagents for Purification of mRNA (Precipitation and/or Washing of mRNA) | |
|---|---|
| Reageant Name | Structure |
| TEG | [structure] |
| TEG-monomethyl ether | [structure] |
| tert-butyl-TEG-O-propionate | [structure] |
| TEG-dimethacrylate | [structure] |
| TEG-dimethyl ether | [structure] |
| TEG-divinyl ether | [structure] |
| TEG-monobutyl ether | [structure] |
| TEG-methyl ether methacrylate | [structure] |
| TEG-monodecyl ether | [structure] |
| TEG-dibenzoate | [structure] |

In some embodiments, precipitating the mRNA in a suspension comprises a PEG polymer, wherein the PEG polymer comprises a PEG-modified lipid. In some embodiments, the PEG-modified lipid is 1,2-dimyristoyl-sn-glycerol, methoxypolyethylene glycol (DMG-PEG-2K). In some embodiments, the PEG modified lipid is a DOPA-PEG conjugate. In some embodiments, the PEG-modified lipid is a poloxamer-PEG conjugate. In some embodiments, the PEG-modified lipid comprises DOTAP. In some embodiments, the PEG-modified lipid comprises cholesterol.

In some embodiments, the mRNA is precipitated in suspension comprising an amphiphilic polymer. In some embodiments, the mRNA is precipitated in a suspension comprising any of the aforementioned PEG reagents. In some embodiments, PEG is in the suspension at about 10% to about 100% weight/volume concentration. For example, in some embodiments, PEG is present in the suspension at about 5%, 10%, 15%, 20%, 25%, 30%, 35%, 40%, 45%, 50%, 55%, 60%, 65%, 70%, 75%, 80%, 85%, 90%, 95%, 100% weight/volume concentration, and any values there between. In some embodiments, PEG is present in the suspension at about 5% weight/volume concentration. In some embodiments, PEG is present in the suspension at about 6% weight/volume concentration. In some embodiments, PEG is present in the suspension at about 7% weight/volume concentration. In some embodiments, PEG is present in the suspension at about 8% weight/volume concentration. In some embodiments, PEG is present in the suspension at about 9% weight/volume concentration. In some embodiments, PEG is present in the suspension at about 10% weight/volume concentration. In some embodiments, PEG is present in the suspension at about 12% weight/volume concentration. In some embodiments, PEG is present in the suspension at about 15% weight/volume. In some embodiments, PEG is present in the suspension at about 18% weight/volume. In some embodiments, PEG is present in the suspension at about 20% weight/volume concentration. In some embodiments, PEG is present in the suspension at about 25% weight/volume concentration. In some embodiments, PEG is present in the suspension at about 30% weight/volume concentration. In some embodiments, PEG is present in the suspension at about 35% weight/volume concentration. In some embodiments, PEG is present in the suspension at about 40% weight/volume concentration. In some embodiments, PEG is present in the suspension at about 45% weight/volume concentration. In some embodiments, PEG is present in the suspension at about 50% weight/volume concentration. In some embodiments, PEG is present in the suspension at about 55% weight/volume concentration. In some embodiments, PEG is present in the suspension at about 60% weight/volume concentration. In some embodiments, PEG is present in the suspension at about 65% weight/volume concentration. In some embodiments, PEG is present in the suspension at about 70% weight/volume concentration. In some embodiments, PEG is present in the suspension at about 75% weight/volume concentration. In some embodiments, PEG is present in the suspension at about 80% weight/volume concentration. In some embodiments, PEG is present in the suspension at about 85% weight/volume concentration. In some embodiments, PEG is present in the suspension at about 90% weight/volume concentration. In some embodiments, PEG is present in the suspension at about 95% weight/volume concentration. In some embodiments, PEG is present in the suspension at about 100% weight/volume concentration.

In some embodiments, precipitating the mRNA in a suspension comprises a volume:volume ratio of PEG to total mRNA suspension volume of about 0.1 to about 5.0. For example, in some embodiments, PEG is present in the mRNA suspension at a volume:volume ratio of about 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, 5.0. Accordingly, in some embodiments, PEG is present in the mRNA suspension at a volume:volume ratio of about 0.1. In some embodiments, PEG is present in the mRNA suspension at a volume:volume ratio of about 0.2. In some embodiments, PEG is present in the mRNA suspension at a volume:volume ratio of about 0.3. In some embodiments, PEG is present in the mRNA suspension at a volume:volume ratio of about 0.4. In some embodiments, PEG is present in the mRNA suspension at a volume:volume ratio of about 0.5. In some embodiments, PEG is present in the mRNA suspension at a volume:volume ratio of about 0.6. In some embodiments, PEG is present in the mRNA suspension at a volume:volume ratio of about 0.7. In some embodiments, PEG is present in the mRNA suspension at a volume:volume ratio of about 0.8. In some embodiments, PEG is present in the mRNA suspension at a volume:volume ratio of about 0.9. In some embodiments, PEG is present in the mRNA suspension at a volume:volume ratio of about 1.0. In some embodiments, PEG is present in the mRNA suspension at a volume:volume ratio of about 1.25. In some embodiments, PEG is present in the mRNA suspension at a volume:volume ratio of about 1.5. In some embodiments, PEG is present in the mRNA suspension at a volume:volume ratio of about 1.75. In some embodiments, PEG is present in the mRNA suspension at a volume:volume ratio of about 2.0. In some embodiments, PEG is present in the mRNA suspension at a volume:volume ratio of about 2.25. In some embodiments, PEG is present in the mRNA suspension at a volume:volume ratio of about 2.5. In some embodiments, PEG is present in the mRNA suspension at a volume:volume ratio of about 2.75. In some embodiments, PEG is present in the mRNA suspension at a volume:volume ratio of about 3.0. In some embodiments, PEG is present in the mRNA suspension at a volume:volume ratio of about 3.25. In some embodiments, PEG is present in the mRNA suspension at a volume:volume ratio of about 3.5. In some embodiments, PEG is present in the mRNA suspension at a volume:volume ratio of about 3.75. In some embodiments, PEG is present in the mRNA suspension at a volume:volume ratio of about 4.0. In some embodiments, PEG is present in the mRNA suspension at a volume:volume ratio of about 4.25. In some embodiments, PEG is present in the mRNA suspension at a volume:volume ratio of about 4.50. In some embodiments, PEG is present in the mRNA suspension at a volume:volume ratio of about 4.75. In some embodiments, PEG is present in the mRNA suspension at a volume:volume ratio of about 5.0. In particular embodiments, PEG is present in the mRNA suspension at a volume:volume ratio of about 1.0, about 1.5 or about 2.0.

In some embodiments, a reaction volume for mRNA precipitation comprises GSCN and PEG. In particular embodiments, a reaction volume for mRNA precipitation comprises GSCN and PEG having a molecular weight of about 4000 to about 8000 g/mol, e.g., about 6000 g/mol (e.g. PEG-6000). GSCN is typically at a final concentration between 2M and 4M. PEG is typically at a final concentration of about 10% to about 20% (weight/volume).

In some embodiments, the method of purifying mRNA is alcohol free.

In some embodiments, a non-aqueous solvent (e.g., alcohol) is added to precipitate mRNA. In some embodiments, a solvent may be isopropyl alcohol, acetone, methyl ethyl ketone, methyl isobutyl ketone, ethanol, methanol, denatonium, and combinations thereof. In embodiments, a solvent is an alcohol solvent (e.g., methanol, ethanol, or isopropanol). In embodiments, a solvent is a ketone solvent (e.g., acetone, methyl ethyl ketone, or methyl isobutyl ketone). In some embodiments, a non-aqueous solvent is mixed with the amphiphilic solution.

In some embodiments, an aqueous solution is added to precipitate mRNA. In some embodiments, the aqueous solution comprises a polymer. In some embodiments, the aqueous solution comprises a PEG polymer.

In some embodiments, the method further includes a step of adding one or more agents that denature proteins (e.g., RNA polymerase and DNase I, which is added after transcription to remove DNA templates) and/or keep proteins soluble in an aqueous medium. In some embodiments, the one or more agents that denature proteins and/or keep proteins soluble in an aqueous medium is a salt, e.g., a chaotropic salt.

In some embodiments, a precipitating step comprises the use of a chaotropic salt (e.g., guanidine thiocyanate) and/or an amphiphilic polymer (e.g., polyethylene glycol or an aqueous solution of polyethylene glycol) and/or an alcohol solvent (e.g., absolute ethanol or an aqueous solution of alcohol such as an aqueous ethanol solution). Accordingly, in some embodiments, the precipitating step comprises the use of a chaotropic salt and an amphiphilic polymer, such as GSCN and PEG, respectively.

In some embodiments, agents that promote precipitation of mRNA include a denaturing agent or result from denaturing conditions. As used herein, the term "denaturing condition" refers to any chemical or physical conditions that can cause denaturation. Exemplary denaturing conditions include, but are not limited to, use of chemical reagents, high temperatures, extreme pH, etc. In some embodiments, a denaturing condition is achieved through adding one or more denaturing agents to an impure preparation containing mRNA to be purified. In some embodiments, a denaturing agent suitable for the present invention is a protein and/or DNA denaturing agent. In some embodiments, a denaturing agent may be: 1) an enzyme (such as a serine proteinase or a DNase), 2) an acid, 3) a solvent, 4) a cross-linking agent, 5) a chaotropic agent, 6) a reducing agent, and/or 7) high ionic strength via high salt concentrations. In some embodiments, a particular agent may fall into more than one of these categories.

In some embodiments, one or more enzymes may be used as denaturing agents to degrade proteins and DNA templates used in mRNA synthesis. In some embodiments, suitable enzymes include, but are not limited to, serine proteases such as chymotrypsin and chymotrypsin-like serine proteases, trypsin and trypsin-like serine proteases, elastase and elastase-like serine proteases, subtilisin and subtilisin-like serine proteases, and combinations thereof, deoxyribonucleases (DNases) such as deoxyribonuclease I, II and/or IV, restriction enzymes such as EcoRI, EcoRII, BamHI, HindIII, SpeI, SphI, StuI, XbaI, and combination thereof.

In some embodiments, an acid may be used as a denaturing agent. In some embodiments, a suitable acid may be acetic acid, formic acid, oxalic acid, citric acid, benzoic acid, chloroacetic acid, dichloroacetic acid, trichloroacetic acid, ascorbic acid, sulfosalicylic acid, and combinations thereof.

In some embodiments, a solvent may be used as a denaturing agent. In some embodiments, the solvent is free of caustic or flammable agents. In some embodiments, a solvent is free of ethanol. In some embodiments, a solvent is free of isopropyl alcohol, acetone, methyl ethyl ketone, methyl isobutyl ketone, ethanol, methanol, denatonium, and combinations thereof. In some embodiments, a solvent is free of an alcohol solvent (e.g., methanol, ethanol, or isopropanol). In some embodiments, a solvent is free of a ketone solvent (e.g., acetone, methyl ethyl ketone, or methyl isobutyl ketone).

In some embodiments, a solvent may be used as a denaturing agent. In some embodiments, a solvent is ethanol. In some embodiments, a solvent is of isopropyl alcohol, acetone, methyl ethyl ketone, methyl isobutyl ketone, ethanol, methanol, denatonium, and combinations thereof. In some embodiments, a solvent is an alcohol solvent (e.g., methanol, ethanol, or isopropanol). In some embodiments, a solvent is of a ketone solvent (e.g., acetone, methyl ethyl ketone, or methyl isobutyl ketone)

In some embodiments, a chaotropic agent may be used as a denaturing agent. Choatropic agents are substances which disrupt the structure of macromolecules such as proteins and nucleic acids by interfering with non-covalent forces such as hydrogen bonds and van der Waals forces. In some embodiments, a chaotropic agent may be urea, thiourea, guanidinium chloride, guanidinium thiocyanate, guanidinium isothiocyanate, lithium acetate, magnesium chloride, sodium dodecyl sulfate, lithium perchlorate and combination thereof.

In some embodiments, a reducing agent may be used as a denaturing agent. Reducing agents are compounds that donate an electron to another species, thus becoming oxidized itself. In some embodiments, a reducing agent may be lithium aluminum hydride, sodium amalgam, diborane, sodium borohydride, sulfites, diisobutylaluminum hydride, phosphites, carbon monoxide, 2-mercaptoethanol, dithiothreitol, or tris(2-carboxyethyl)phosphine, and combinations thereof.

In some embodiments, one or more of pH, heat, and/or heavy metals (such as lead, mercury or cadmium) may also be used as denaturing agents to provide a denaturating condition. Extremes of pH are known to cause a protein to denature. Although the backbone of a protein chain is neutral, the amino acid residues that comprise the protein often contain acidic and basic groups. These groups are usually charged and can form salt bridges with a group of opposite charge. Accordingly, extremes of pH can change the charges on these acidic and basic groups, disrupting salt bridges.

In some embodiments, less drastic changes in pH may also affect the activity and solubility of a protein. Like individual amino acids, proteins have an isoelectric point at which the number of negative charges equals the number of positive charges. This is frequently the point of minimum water solubility. At the isoelectric pH, there is no net charge on the molecule. Individual molecules have a tendency to approach one another, coagulate, and precipitate out of solution. At a pH above or below the isoelectric pH, the molecules have a net negative or positive charge, respectively. Thus when protein molecules approach each other, they have the same overall charge and repulse each other.

In some embodiments, heat may be used as a denaturing agent. Heat can supply kinetic energy to protein molecules, causing their atoms to vibrate more rapidly. In some embodiments, this will disrupt relatively weak forces such as hydrogen bonds and hydrophobic interactions. Heat is also used in sterilization to denature and hence destroy the enzymes in bacteria.

In some embodiments, salts of metal ions such as mercury (II), lead(II), and silver may be used as denaturing agents due to their ability to form strong bonds with disulfide groups and with the carboxylate ions of the acidic amino acids. Thus, they disrupt both disulfide bridges and salt linkages and cause the protein to precipitate out of solution as an insoluble metal-protein salt.

In some embodiments, high concentrations of salt (high salinity) may also be used as a denaturing agent. High concentrations of salts are known to cause both proteins and nucleic acids to precipitate from an aqueous solution. In some embodiments, a high concentration of salt may be between 1M and 10M, inclusive. In some embodiments, a high concentration of salt may be between 2M and 9M, inclusive. In some embodiments, a high concentration of salt may be between 2M and 8M, inclusive. In some embodiments, a high concentration of salt may be between 2M and 5M, inclusive. In some embodiments, a high concentration of salt may be greater than 1M concentration. In some embodiments, a high concentration of salt may be greater than 2M concentration. In some embodiments, a high concentration of salt may be greater than 3M concentration. In some embodiments, a high concentration of salt may be greater than 4M concentration. In some embodiments, a high concentration of salt may be greater than 5M concentration. In some embodiments, a high concentration of salt may be greater than 6M concentration. In some embodiments, a high concentration of salt may be greater than 7M concentration. In some embodiments, a high concentration of salt may be greater than 8M concentration. In some embodiments, a single salt is used as a denaturing agent. In some embodiments, more than one salt is used as a denaturing agent.

In some embodiments, a salt used as a denaturing agent may be a calcium salt, an iron salt, a magnesium salt, a potassium salt, a sodium salt, or a combination thereof. Exemplary specific salts suitable for use as denaturing agents in some embodiments include, but are not limited to, potassium chloride (KCl), sodium chloride (NaCl), lithium chloride (LiCl), calcium chloride ($CaCl_2$), potassium bromide (KBr), sodium bromide (NaBr), lithium bromide (LiBr). In some embodiments, the denaturing agent the impure preparation is subjected to is potassium chloride (KCl). In some embodiments, KCl is added such that the resulting KCl concentration is about 1M or greater. In some embodiments, KCl is added such that the resulting KCl concentration is about 2 M or greater, 3 M or greater, 4 M or greater, or 5 M or greater.

In some embodiments, the method does not comprise a chromatography step. In some embodiments, the precipitated mRNA is centrifuged to obtain an mRNA pellet. The mRNA pellet is then resuspended in a buffer solution, such as water, TE, sodium citrate, or combinations thereof. Accordingly, in some embodiments, the mRNA pellet is resuspended in water. In some embodiments, the mRNA pellet is resuspended in TE. In some embodiments, the mRNA pellet is resuspended in sodium citrate.

In some embodiments, the mRNA is precipitated in a suspension comprising GSCN at a final concentration of between about 2-4 M; PEG having a molecular weight of about 4000 to about 8000 g/mol, e.g., about 6000 g/mol (e.g. PEG-6000) at a final concentration of between about 5% and about 20% (weight/volume); and a filter aid (for example a cellulose-based filtering aid) at a mass ratio with the precipitated mRNA of about 2:1; about 5:1; about 10:1 or about 15:1. In some embodiments, the mRNA is precipitated in a suspension comprising GSCN at a final concentration of about 2.5-3 M; PEG having a molecular weight of about 6000 g/mol (e.g. PEG-6000) at a final concentration of between about 10% and about 15% (weight/volume); and a filter aid (for example a cellulose-based filtering aid) at a mass ratio with the precipitated mRNA of about 10:1. In particular embodiments, the mRNA is precipitated in a suspension comprising GSCN at a final concentration of about 2.7M; PEG having a molecular weight of about 6000 g/mol (e.g. PEG-6000) at a final concentration of about 12% (weight/volume); and a filter aid (for example a cellulose-based filtering aid, e.g., Solka-Floc) at a mass ratio with the precipitated mRNA of about 10:1. As shown in the examples, suspensions comprising these concentrations of mRNA, salt and PEG achieve highly effective purification of the mRNA without precipitating process enzymes.

In some embodiments, MTEG can be used in place of PEG to provide a suspension of precipitated mRNA. In particular embodiments, MTEG is used for this purpose at a final concentration of about 15% to about 45% weight/volume. In some embodiments, the suspension comprises MTEG at a final concentration of about 20% to about 40% weight/volume. In some embodiments, the suspension comprises MTEG at a final concentration of about 20% weight/volume. In some embodiments, the suspension comprises MTEG at a final concentration of about 25% weight/volume. In some embodiments, the suspension comprises MTEG at a final concentration of about 30% weight/volume. In some embodiments, the suspension comprises MTEG at a final concentration of about 35% weight/volume. In some embodiments, the suspension comprises MTEG at a final concentration of less than 35% weight/volume. The rest of the conditions used in MTEG-induced precipitation are the same as those used in the PEG-induced precipitation. As shown in the examples, a suspension comprising mRNA, GSCN and MTEG, with MTEG at a final concentration of less than 35% weight/volume ensured efficient recovery of mRNA without unwanted precipitation of process enzymes. Particularly suitable for efficient recovery of mRNA without unwanted precipitation of process enzymes is a suspension comprising mRNA, GSCN and MTEG, with MTEG at a final concentration of about 25%, in addition to a filter aid (for example cellulose-based filtering aid) at a mass ratio with the precipitated mRNA of about 10:1.

For example, GSCN can be provided as a 4-8M solution (e.g. in a 10 mM DTT buffer), which is then combined with the mRNA and MTEG to prepare a suspension of precipitated mRNA. In some embodiments, the suspension comprises precipitated mRNA, a chaotropic salt, for example GSCN, and MTEG at a volume ratio of 1:2-3:1-2. In some embodiments, the suspension comprises precipitated mRNA, a chaotropic salt, for example GSCN, and MTEG at a volume ratio of 1:2-2.5:1-2. In some embodiments, the suspension comprises precipitated mRNA, a chaotropic salt, for example GSCN, and MTEG at a volume ratio of 1:2.3:1-2. In particular embodiments, the suspension comprises precipitated mRNA, GSCN, and MTEG at a ratio of 1:2.3:2. In particular embodiments, the suspension comprises precipitated mRNA, GSCN, and MTEG at a volume ratio of 1:2.3:1.7. In particular embodiments, the suspension comprises precipitated mRNA, GSCN, and MTEG at a ratio of 1:2.3:1. As shown in the examples, a suspension comprising mRNA, GSCN and MTEG in volume ratios of 1:2.3:1, 1:2.3:1.7 and 1:2.3:2 is particularly suitable in the polymer-induced purification method in combination with an MTEG wash solution at a final concentration of about 95%—this combination of steps ensures efficient recovery of mRNA without unwanted precipitation of process.

Capturing the mRNA

Another step of the method of purifying mRNA as described herein comprises capturing the mRNA. Various methods of capturing mRNA are known in the art. In some embodiments, an impure preparation containing the precipitated mRNA is subjected to a purification process involving membrane filtration such that the precipitated mRNA is captured or retained by a membrane or filter. Thus, in some embodiments, the impure preparation is subjected to membrane filtration following precipitation without pre-treatment to remove insolubles.

Various types of membrane filtration may be used to capture or retain precipitated mRNA. Typically, membrane filtration involves separating solids from fluids using one or more interposed permeable membranes. Membrane filtration may also be used to filter particles from a gaseous sample. Generally speaking, there are two major forms of membrane filtration, passive filtration, which proceeds solely due to solution-diffusion, and active filtration, which uses positive pressure or negative pressure (i.e. vacuum) to force the liquid or gas across the membrane. Typically, membrane filtration involves load, wash and elute steps.

Capturing the mRNA on a filter includes loading a solution comprising the precipitated mRNA onto a membrane or filter. This step is typically referred to as a load step. The load step involves loading the feed (e.g., an impure preparation containing precipitated mRNA) onto a membrane or filter and forcing it through by positive or negative pressure, leaving retentate captured or retained on the membrane. As used herein, the term "retentate" refers to any non-permeating solute and/or insoluble that is retained by a membrane. According to the present invention, precipitated mRNA is captured by a membrane as retentate. As used herein, the term "membrane" or "filter" refers to any porous layer or sheet of material. In this application, the term "membrane" is used inter-changeably with filter.

In some embodiments, a suitable membrane has a pore size appropriate for capturing or retaining precipitated mRNA, while letting impurities (including soluble impurities and/or insoluble with size less than the pore size) pass through as permeate. In some embodiments, a suitable membrane has an average pore size of or greater than about 0.10 µm, 0.20 µm, 0.22 µm, 0.24 µm, 0.26 µm, 0.28 µm, 0.30 µm, 0.40 µm, 0.5 µm, or 1.0 µm. In a particular embodiment, a suitable membrane has an average pore size of about 0.22 µm. In some embodiments, a suitable membrane has an average pore size of about 1.0 µm, 1.5 µm, 2.0 µm, 2.5 µm, 3.0 µm, 3.5 µm, 4.0 µm, 4.5 µm, 5.0 µm, 5.5 µm, 6.0 µm, 6.5 µm, 7.0 µm, 7.5 µm, 8.0 µm, 8.5 µm, 9.0 µm, 9.5 µm, and 10 µm. In some embodiments, for example for use with Normal Flow Filtration (NFF) or depth filtration, a suitable membrane has an average pore size of about 5 µm to about 8 µm. In some embodiments, a suitable membrane for use with NFF or depth filtration has an average pore size of about 7 µm. In some embodiments, for example for use with centrifuge filtration, a suitable membrane has an average pore size of about 0.5 µm to about 2.0 µm. In some embodiments, a suitable membrane for use with centrifuge filtration is about 1 µm. In some embodiments, appropriate pore size for retaining precipitated mRNA may be determined by the nominal molecular weight limits (NMWL) of the precipitated mRNA, also referred to as the molecular weight cut off (MWCO). Typically, a membrane with pore size less than the NMWL or MWCO of the precipitated mRNA is used. In some embodiments, a membrane with pore size two to six (e.g., 2, 3, 4, 5, or 6) times below the NMWL or MWCO of the precipitated mRNA is used. In some embodiments, a suitable membrane for the present invention may have pore size of or greater than about 100 kilodaltons (kDa), 300 kDa, 500 kDa, 1,000 kDa, 1,500 kDa, 2,000 kDa, 2,500 kDa, 3,000 kDa, 3,500 kDa, 4,000 kDa, 4,500 kDa, 5,000 kDa, 5,500 kDa, 6,000 kDa, 6,500 kDa, 7,000 kDa, 7,500 kDa, 8,000 kDa, 8,500 kDa, 9,000 kDa, 9,500 kDa, or 10,000 kDa. In some embodiments, the membrane has a pore size greater than the NMWL and MWCO of the mRNA but less than the NMWL and MWCO of the precipitated mRNA. Accordingly, in certain embodiments, the invention provides a method of purifying mRNA comprising precipitating the mRNA in a suspension comprising a high molar salt solution and PEG polymer to provide precipitated mRNA in the suspension, capturing the precipitated mRNA on a filter having a pore size greater than the NMWL and MWCO of the mRNA but less than the NMWL and MWCO of the precipitated mRNA; and washing the captured and precipitated mRNA to obtain a purified mRNA composition substantially free of contaminants.

A suitable membrane for the present invention may be made of any material. Exemplary membrane materials include, but are not limited to, polyethersulfone (mPES) (not modified), polyethersulfone (mPES) hollow fiber membrane, polyvinylidene fluoride (PVDF), cellulose acetate, nitrocellulose, MCE (mixed cellulose esters), ultra-high MW polyethylene (UPE), polyfluorotetraethylene (PTFE), nylon, polysulfone, polyether sulfone, polyacrilonitrile, polypropylene, polyvinyl chloride, and combination thereof. In particular embodiments, the membrane is a polypropylene filter with an average pore size of about 1.0 µm.

A suitable membrane for the present invention may have various surface area. In some embodiments, a suitable membrane has a sufficiently large surface area to facilitate large scale production of mRNA. For example, a suitable membrane may have a surface area of or greater than about 2,000 cm$^2$, 2,500 cm$^2$, 3,000 cm$^2$, 3,500 cm$^2$, 4,000 cm$^2$, 4,500 cm$^2$, 5,000 cm$^2$, 7,500 cm$^2$, 10,000 cm$^2$, 5 m$^2$, 10 m$^2$, 12 m$^2$, 15 m$^2$, 20 m$^2$, 24 m$^2$, 25 m$^2$, 30 m$^2$, or 50 µm$^2$.

Membrane filtration may be performed in various format to capture precipitated mRNA. In some embodiments, membrane filtration is performed as part of tangential flow filtration (TFF). In some embodiments, membrane filtration comprises Normal Flow Filtration (NFF) or depth filtration. In some embodiments, membrane filtration comprises centrifuge filtration.

Filter Aids (Including Dispersants)

In some embodiments, a filter aid is used in the methods described herein. A filter aid may be used when purifying precipitated mRNA using a filtering centrifuge. The filter aid may assist in retaining precipitated mRNA on the filter of a filtering centrifuge and allowing removal of the retained mRNA from the surface of the filter of a filtering centrifuge.

In some embodiments, the filter aid is a dispersant. In some embodiments, the filter aid comprises one or more of ash, clay, diatomaceous earth, perlite, glass beads, plastic beads, polymers, polypropylene beads, polystyrene beads, salts (e.g., cellulose salts), sand, volcanic ash, diatomaceous earth and/or sugars. In some embodiments, the dispersant is a bead. In some embodiments, the precipitated mRNA composition does not comprise a dispersant.

In some embodiments, a step of adding one or more agents that promotes precipitation of mRNA is performed in the absence of any dispersants.

In some embodiments, a step of adding one or more agents that promotes precipitation of mRNA is performed in the presence of at least one dispersant.

In some embodiments, a dispersant is added to the slurry obtained following the addition of one or more agents that promotes precipitation of mRNA.

Thus, in some embodiments, the purification method may further include one or more steps for separating the dispersant from the purified mRNA precipitate, e.g., washing and drying the cake. The method may further include a step of solubilizing and eluting the purified mRNA from the cake using an aqueous medium, e.g., water, while filtering the dispersant. In embodiments, a precipitating step and a drying step may be performed simultaneously.

In embodiments, a filtration aid is cellulose. In embodiments, a cellulose filtration aid is powdered cellulose fiber (e.g., Solka-Floc® or Sigmacell Cellulose 20). In embodiments, a cellulose filtration aid is a powdered cellulose fiber such as Solka-Floc® 200 NF or Sigmacell Cellulose Type 20 (20 μm). In some embodiments, the filter aid is volcanic ash. In some embodiments, the filter aid is diatomaceous earth.

In some embodiments, the precipitated mRNA and filter aid (for example powdered cellulose fibre such as Solka Floc) are at a mass ratio of 1:2; 1:5; 1:10 or 1:15. In particular embodiments, the precipitated mRNA and filter aid (for example powdered cellulose fibre such as Solka Floc) are at a mass ratio of 1:10.

Washing the Captured mRNA

The method of purifying mRNA also comprises washing the captured insoluble mRNA before eluting to get rid of impurities retained on the membrane.

In some embodiments, an amphiphilic polymer is used in the wash step. In some embodiments, the amphiphilic polymer is a polyethylene glycol (PEG). Accordingly, in some embodiments, a PEG solution ("PEG wash solution") is used for washing the captured mRNA. The PEG wash solution comprises triethylene glycol, tetraethylene glycol, PEG 200, PEG 300, PEG 400, PEG 600, PEG 1,000, PEG 1,500, PEG 2,000, PEG 3,000, PEG 3,350, PEG 4,000, PEG 6,000, PEG 8,000, PEG 10,000, PEG 20,000, PEG 35,000, and PEG 40,000, or combination thereof. In some embodiments, the PEG wash solution comprises triethylene glycol. In some embodiments, the PEG wash solution comprises tetraethylene glycol. In some embodiments, the PEG wash solution comprises PEG 200. In some embodiments, the PEG solution comprises PEG 300. In some embodiments, the wash PEG wash solution comprises PEG 400. In some embodiments, the PEG wash solution comprises PEG 600. In some embodiments, the PEG wash solution comprises PEG 1,000. In some embodiments, the PEG wash solution comprises PEG 1,500. In some embodiments, the PEG wash solution comprises PEG 2,000. In some embodiments, the PEG wash solution comprises PEG 3,000. In some embodiments, the PEG wash solution comprises PEG 3,350. In some embodiments, the PEG wash solution comprises PEG 4,000. In some embodiments, the PEG wash solution comprises PEG 6,000. In some embodiments, the PEG wash solution comprises PEG 8,000. In some embodiments, the PEG wash solution comprises PEG 10,000. In some embodiments, the PEG wash solution comprises PEG 20,000. In some embodiments, the PEG wash solution comprises PEG 35,000. In some embodiments, the PEG wash solution comprises PEG 40,000. In some embodiments, washing the precipitated mRNA includes one or more washes comprising PEG having a viscosity of 90 centistrokes or less. In some embodiments, the PEG used to wash the precipitated mRNA has a viscosity of 80 centistrokes or less. In some embodiments, the PEG used to wash the precipitated mRNA has a viscosity of 70 centistrokes or less. In some embodiments, the PEG used to wash the precipitated mRNA has a viscosity of 60 centistrokes or less. In some embodiments, the PEG used to wash the precipitated mRNA has a viscosity of 50 centistrokes or less. In some embodiments, the PEG used to wash the precipitated mRNA has a viscosity of 40 centistrokes or less. In some embodiments, the PEG used to wash the precipitated mRNA has a viscosity of 30 centistrokes or less. In some embodiments, the PEG used to wash the precipitated mRNA has a viscosity of 20 centistrokes or less. In some embodiments, the PEG used to wash the precipitated mRNA has a viscosity of 10 centistrokes or less. In some embodiments, washing the precipitated mRNA can be achieved using triethylene glycol (TEG). In some embodiments, washing the precipitated mRNA can be achieved using triethylene glycol monomethyl ether (MTEG). In some embodiments, washing the precipitated mRNA can be achieved using tert-butyl-TEG-O-propionate. In some embodiments, washing the precipitated mRNA can be achieved using TEG-dimethacrylate. In some embodiments, washing the precipitated mRNA can be achieved using TEG-dimethyl ether. In some embodiments, washing the precipitated mRNA can be achieved using TEG-divinyl ether. In some embodiments, washing the precipitated mRNA can be achieved using TEG-monobutyl. In some embodiments, washing the precipitated mRNA can be achieved using TEG-methyl ether methacrylate. In some embodiments, washing the precipitated mRNA can be achieved using TEG-monodecyl ether. In some embodiments, washing the precipitated mRNA can be achieved using TEG-dibenzoate. The structures of each of these reagents are shown above in Table A.

The viscosity of a liquid solution can be measured using methods well known in the art, for example using a viscometer, at room temperature (for example between about 18 and 25° C.).

In some embodiments, the PEG in the PEG wash solution comprises a PEG-modified lipid. In some embodiments, the PEG in the PEG wash solution is the PEG-modified lipid 1,2-dimyristoyl-sn-glycerol, methoxypolyethylene glycol (DMG-PEG-2K). In some embodiments, the PEG modified lipid is a DOPA-PEG conjugate. In some embodiments, the PEG-modified lipid is a poloxamer-PEG conjugate. In some embodiments, the PEG-modified lipid comprises DOTAP. In some embodiments, the PEG-modified lipid comprises cholesterol.

In some embodiments, the PEG wash solution comprises a mixture of two or more kinds of molecular weight PEG polymers. For example, in some embodiments, two, three, four, five, six, seven, eight, nine, ten, eleven, or twelve molecular weight PEG polymers comprise the PEG wash solution. Accordingly, in some embodiments, the PEG wash solution comprises a mixture of one or more PEG polymers. In some embodiments, the mixture of PEG polymers comprises polymers having distinct molecular weights.

The PEG used in the PEG wash solution can have various geometrical configurations. For example, suitable PEG polymers include PEG polymers having linear, branched, Y-shaped, or multi-arm configuration. In some embodiments, the PEG is in a suspension comprising one or more PEG of distinct geometrical configurations.

In some embodiments, PEG in the wash solution is present at about 10% to about 100% weight/volume concentration. For example, in some embodiments, PEG is present in the wash solution at about 10%, 15%, 20%, 25%, 30%, 35%, 40%, 45%, 50%, 55%, 60%, 65%, 70%, 75%, 80%, 85%, 90%, 95%, 100% weight/volume concentration, and any values there between. In some embodiments, PEG is present in the wash solution at about 10% weight/volume concentration. In some embodiments, PEG is present in the wash solution at about 15% weight/volume. In some embodiments, PEG is present in the wash solution at about 20% weight/volume concentration. In some embodiments, PEG is present in the wash solution at about 25% weight/volume concentration. In some embodiments, PEG is present in the wash solution at about 30% weight/volume concentration. In some embodiments, PEG is present in the wash solution at about 35% weight/volume concentration. In some embodiments, PEG is present in the wash solution at about 40% weight/volume concentration. In some embodiments, PEG is present in the wash solution at about 45% weight/volume concentration. In some embodiments, PEG is present in the wash solution at about 50% weight/volume concentration. In some embodiments, PEG is present in the wash solution at about 55% weight/volume concentration. In some embodiments, PEG is present in the wash solution at about 60% weight/volume concentration. In some embodiments, PEG is present in the wash solution at about 65% weight/volume concentration. In some embodiments, PEG is present in the wash solution at about 70% weight/volume concentration. In some embodiments, PEG is present in the wash solution at about 75% weight/volume concentration. In some embodiments, PEG is present in the wash solution at about 80% weight/volume concentration. In some embodiments, PEG is present in the wash solution at about 85% weight/volume concentration. In some embodiments, PEG is present in the wash solution at about 90% weight/volume concentration. In some embodiments, PEG is present in the wash solution at about 95% weight/volume concentration. In some embodiments, PEG is present in the wash solution at about 100% weight/volume concentration.

In some embodiments, the wash buffer comprises PEG-400 at a concentration of about between 80 and 100%. Accordingly, in some embodiments, the wash buffer comprises PEG-400 at a concentration of about 80%. In some embodiments, the wash buffer comprises PEG-400 at a concentration of about 85%. In some embodiments, the wash buffer comprises PEG-400 at a concentration of about 90%. In some embodiments, the wash buffer comprises PEG-400 at a concentration of about 95%. In some embodiments, the wash buffer comprises PEG-400 at a concentration of about 100%.

In some embodiments, the precipitated mRNA is washed in a solution comprising an amphiphilic polymer. In some embodiments, the amphiphilic polymer is PEG. The precipitated mRNA can be washed 1, 2, 3, 4, 5, 6, 7, 8, 9, 10, or more than 10 times. Accordingly, in some embodiments, the precipitated mRNA is washed with a solution comprising a PEG polymer one time. In some embodiments, the precipitated mRNA is washed with a solution comprising a PEG polymer two times. In some embodiments, the precipitated mRNA is washed with a solution comprising a PEG polymer three times. In some embodiments, the precipitated mRNA is washed with a solution comprising a PEG polymer four times. In some embodiments, the precipitated mRNA is washed with a solution comprising a PEG polymer five times. In some embodiments, the precipitated mRNA is washed with a solution comprising a PEG polymer six times. In some embodiments, the precipitated mRNA is washed with a solution comprising a PEG polymer seven times. In some embodiments, the precipitated mRNA is washed with a solution comprising a PEG polymer eight times. In some embodiments, the precipitated mRNA is washed with a solution comprising a PEG polymer nine times. In some embodiments, the precipitated mRNA is washed with a solution comprising a PEG polymer ten times. In some embodiments, the precipitated mRNA is washed with a solution comprising a PEG polymer more than ten times.

In some embodiments, the wash solution used to wash the captured mRNA is aqueous. Accordingly, in some embodiments, the wash solution is free of alcohol, such as ethanol, isopropyl alcohol, or benzyl alcohol.

In some embodiments, the PEG wash solution comprises a non-aqueous component, such as, for example, ethanol, isopropyl alcohol or benzyl alcohol.

In some embodiments, the wash step comprises multiple rinse cycles using a solution comprising an amphiphilic polymer (e.g., polyethylene glycol). In some embodiments, the wash step comprises multiple rinses using a solution comprising one or more distinct amphiphilic polymers. In some embodiments, the wash step may be carried out by multiple rinse cycles using a solution comprising about 10% to about 100% amphiphilic polymer. In certain embodiments, the multiple rinse cycles comprise 2 cycles, 3 cycles, 4 cycles, 5 cycles, 6 cycles, 7 cycles, 8 cycles, 9 cycles, 10 cycles or more than 10 cycles.

In some embodiments, PEG is present in the wash solution at about 90 to about 100% weight/volume concentration. In particular embodiments, the PEG (for example PEG-400) is present in the wash solution at about 90% weight/volume concentration. As shown in the examples, a final concentration of PEG having a molecular weight of about 400 g/mol (e.g. PEG-400) of about 90% to about 100% weight/volume is particularly suitable for the wash step as this wash solution resulted in a high yield and highly pure mRNA samples.

In some embodiments, MTEG is present in the wash solution at between about 75% and about 95% weight/volume concentration. In some embodiments, MTEG is present in the wash solution at about 75%, about 80%, about 85%, about 90% or about 95% weight/volume concentration. In some embodiments, MTEG is present in the wash solution at about 90% to about 100% by weight/volume concentration. In particular embodiments, MTEG is present in the wash solution at about 95% by weight/volume concentration. As shown in the examples, a final concentration of MTEG of about 90 or about 95% weight/volume is particularly suitable for the wash step, as these final concentrations achieved highly efficient recovery of the mRNA without precipitating process enzymes.

Elute or Collect

Typically, captured or retained mRNA may be eluted or collected by re-solubilizing the precipitated mRNA into a solution. For example, captured mRNA may be eluted with RNAse-free water. In certain embodiments, eluting the captured mRNA involves recirculating the RNAse-free water. For example, the RNAse-free water may be circulated for about 5-30 minutes (e.g., about 5-25 minutes, about 5-20 minutes, or about 5-15 minutes). In particular embodiments, the RNAse-free water is re-circulated for about 5-10 minutes (e.g., for about 5, 6, 7, 8, 9 or 10 minutes). Other buffers, such as TE and/or sodium citrate can be used to re-solubilize the mRNA. The term "elution" may be used in the context of purification processes that involve e.g. depth filtration, whereas the term "collection" may be used in the context of purification processes that involve centrifugation.

In some embodiments, re-solubilized mRNA may be dialyzed into a desired formulation at a desired concentration. Various formulations may be used for dialysis. In some embodiments, the purified mRNA solution is dialyzed with 1 mM sodium citrate. In some embodiments, the purified mRNA solution is dialyzed with sodium acetate, ammonium carbonate, ammonium bicarbonate, pyridinium acetate, pyridinium formate, ammonium acetate, urea, potassium chloride, etc. Depending on the size of mRNA of interest, dialysis membranes with appropriate molecular weight cut-off (MWCO) may be used. For example, suitable dialysis membranes may have a MWCO of about 50 kDa, 60 kDa, 70 kDa, 80 kDa, 90 kDa, 100 kDa, 150 kDa, 200 kDa, 250 kDa, 300 kDa, 350 kDa, 400 kDa, 450 kDa, or 500 kDa.

Scale and Recovered Amounts

A particular advantage provided by the present invention is the ability to purify mRNA, in particular, mRNA synthesized in vitro, at a large or commercial scale. For example, in some embodiments in vitro synthesized mRNA is purified at a scale of or greater than about 100 milligram, 1 gram, 10 gram, 50 gram, 100 gram, 200 gram, 300 gram, 400 gram, 500 gram, 600 gram, 700 gram, 800 gram, 900 gram, 1 kg, 5 kg, 10 kg, 50 kg, 100 kg, one metric ton, ten metric ton or more per batch. In embodiments, in vitro synthesized mRNA is purified at a scale of or greater than about 1 kg.

In one particular embodiment, in vitro synthesized mRNA is purified at a scale of 10 gram per batch. In one particular embodiment, in vitro synthesized mRNA is purified at a scale of 20 gram per batch. In one particular embodiment, in vitro synthesized mRNA is purified at a scale of 25 gram per batch. In one particular embodiment, in vitro synthesized mRNA is purified at a scale of 50 gram per batch. In another particular embodiment, in vitro synthesized mRNA is purified at a scale of 100 gram per batch. In yet another particular embodiment, in vitro synthesized mRNA is purified at a scale of 1 kg per batch. In yet another particular embodiment, in vitro synthesized mRNA is purified at a scale of 10 kg per batch. In yet another particular embodiment, in vitro synthesized mRNA is purified at a scale of 100 kg per batch. In yet another particular embodiment, in vitro synthesized mRNA is purified at a scale of 1,000 kg per batch. In yet another particular embodiment, in vitro synthesized mRNA is purified at a scale of 10,000 kg per batch.

In some embodiments, the mRNA is purified at a scale of or greater than 1 gram, 5 gram, 10 gram, 15 gram, 20 gram, 25 gram, 30 gram, 35 gram, 40 gram, 45 gram, 50 gram, 75 gram, 100 gram, 150 gram, 200 gram, 250 gram, 300 gram, 350 gram, 400 gram, 450 gram, 500 gram, 550 gram, 600 gram, 650 gram, 700 gram, 750 gram, 800 gram, 850 gram, 900 gram, 950 gram, 1 kg, 2.5 kg, 5 kg, 7.5 kg, 10 kg, 25 kg, 50 kg, 75 kg, 100 kg or more per batch.

In some embodiments, the solution comprising mRNA includes at least one gram, ten grams, one-hundred grams, one kilogram, ten kilograms, one-hundred kilograms, one metric ton, ten metric tons, or more mRNA, or any amount there between. In some embodiments, a method described herein is used to purify an amount of mRNA that is at least about 250 mg mRNA. In one embodiment, a method described herein is used to purify an amount of mRNA that is at least about 250 mg mRNA, about 500 mg mRNA, about 750 mg mRNA, about 1000 mg mRNA, about 1500 mg mRNA, about 2000 mg mRNA, or about 2500 mg mRNA. In embodiments, a method described herein is used to purify an amount of mRNA that is at least about 250 mg mRNA to about 500 g mRNA. In embodiments, a method described herein is used to purify an amount of mRNA that is at least about 500 mg mRNA to about 250 g mRNA, about 500 mg mRNA to about 100 g mRNA, about 500 mg mRNA to about 50 g mRNA, about 500 mg mRNA to about 25 g mRNA, about 500 mg mRNA to about 10 g mRNA, or about 500 mg mRNA to about 5 g mRNA. In embodiments, a method described herein is used to purify an amount of mRNA that is at least about 100 mg mRNA to about 10 g mRNA, about 100 mg mRNA to about 5 g mRNA, or about 100 mg mRNA to about 1 g mRNA.

In some embodiments, a method described herein provides a recovered amount of purified mRNA (or "yield") that is at least about 40%, 45%, 50%, about 55%, about 60%, about 65%, about 70%, about 75%, about 80%, about 85%, about 90%, about 95% about 97%, about 98%, about 99%, or about 100%. Accordingly, in some embodiments, the recovered amount of purified mRNA is about 40%. In some embodiments, the recovered amount of purified mRNA is about 45%. In some embodiments, the recovered amount of purified mRNA is about 50%. In some embodiments, the recovered amount of purified mRNA is about 55%. In some embodiments, the recovered amount of purified mRNA is about 60%. In some embodiments, the recovered amount of purified mRNA is about 65%. In some embodiments, the recovered amount of purified mRNA is about 70%. In some embodiments, the recovered amount of purified mRNA is about 75%. In some embodiments, the recovered amount of purified mRNA is about 75%. In some embodiments, the recovered amount of purified mRNA is about 80%. In some embodiments, the recovered amount of purified mRNA is about 85%. In some embodiments, the recovered amount of purified mRNA is about 90%. In some embodiments, the recovered amount of purified mRNA is about 91%. In some embodiments, the recovered amount of purified mRNA is about 92%. In some embodiments, the recovered amount of purified mRNA is about 93%. In some embodiments, the recovered amount of purified mRNA is about 94%. In some embodiments, the recovered amount of purified mRNA is about 95%. In some embodiments, the recovered amount of purified mRNA is about 96%. In some embodiments, the recovered amount of purified mRNA is about 97%. In some embodiments, the recovered amount of purified mRNA is about 98%. In some embodiments, the recovered amount of purified mRNA is about 99%. In some embodiments, the recovered amount of purified mRNA is about 100%.

In particular embodiments, the recovered amount of purified mRNA is more than about 80% or more than about 90%, for example between about 90% and 100%.

Characterization of Purified mRNA

The mRNA purification methods provided herein result in a purified mRNA composition that is substantially free of contaminants comprising short abortive RNA species, long abortive RNA species, double-stranded RNA (dsRNA), residual plasmid DNA, residual in vitro transcription enzymes, residual solvent and/or residual salt.

The methods described herein result in purified mRNA that has a purity of about between 60% and about 100%. Accordingly, in some embodiments, the purified mRNA has a purity of about 60%. In some embodiments, the purified mRNA has a purity of about 65%. In some embodiments, the purified mRNA has a purity of about 70%. In some embodiments, the purified mRNA has a purity of about 75%. In some embodiments, the purified mRNA has a purity of about 80%. In some embodiments, the purified mRNA has a purity of about 85%. In some embodiments, the purified mRNA has a purity of about 90%. In some embodiments, the purified mRNA has a purity of about 91%. In some embodiments, the purified mRNA has a purity of about 92%. In some embodiments, the purified mRNA has a purity of about 93%. In some embodiments, the purified mRNA has a purity of about 94%. In some embodiments, the purified mRNA has a purity of about 95%. In some embodiments, the purified mRNA has a purity of about 96%. In some embodiments, the purified mRNA has a purity of about 97%. In some embodiments, the purified mRNA has a purity of about 98%. In some embodiments, the purified mRNA has a purity of about 99%. In some embodiments, the purified mRNA has a purity of about 100%.

In some embodiments, mRNA generated by the method disclosed herein has less than 10%, less than 9%, less than 8%, less than 7%, less than 6%, less than 5%, less than 4%, less than 3%, less than 2%, less than 1%, less than 0.5%, and/or less than 0.1% impurities other than full-length mRNA. The impurities include IVT contaminants, e.g., proteins, enzymes, DNA templates, free nucleotides, residual solvent, residual salt, double-stranded RNA (dsRNA), prematurely aborted RNA sequences ("shortmers" or "short abortive RNA species"), and/or long abortive RNA species. In some embodiments, the purified mRNA is substantially free of process enzymes.

In some embodiments, the residual plasmid DNA in the purified mRNA using the purification methods described herein is less than about 1 pg/mg, less than about 2 pg/mg, less than about 3 pg/mg, less than about 4 pg/mg, less than about 5 pg/mg, less than about 6 pg/mg, less than about 7 pg/mg, less than about 8 pg/mg, less than about 9 pg/mg, less than about 10 pg/mg, less than about 11 pg/mg, or less than about 12 pg/mg. Accordingly, the residual plasmid DNA in the purified mRNA using the purification methods described herein is less than about 1 pg/mg. In some embodiments, the residual plasmid DNA in the purified mRNA using the purification methods described herein is less than about 2 pg/mg. In some embodiments, the residual plasmid DNA in the purified mRNA using the purification methods described herein is less than about 3 pg/mg. In some embodiments, the residual plasmid DNA in the purified mRNA using the purification methods described herein is less than about 4 pg/mg. In some embodiments, the residual plasmid DNA in the purified mRNA using the purification methods described herein is less than about 5 pg/mg. In some embodiments, the residual plasmid DNA in the purified mRNA using the purification methods described herein is less than about 6 pg/mg. In some embodiments, the residual plasmid DNA in the purified mRNA using the purification methods described herein is less than about 7 pg/mg. In some embodiments, the residual plasmid DNA in the purified mRNA using the purification methods described herein is less than about 8 pg/mg. In some embodiments, the residual plasmid DNA in the purified mRNA using the purification methods described herein is less than about 9 pg/mg. In some embodiments, the residual plasmid DNA in the purified mRNA using the purification methods described herein is less than about 10 pg/mg. In some embodiments, the residual plasmid DNA in the purified mRNA using the purification methods described herein is less than about 11 pg/mg. In some embodiments, the residual plasmid DNA in the purified mRNA using the purification methods described herein is less than about 12 pg/mg.

In some embodiments, the present invention removes or eliminates a high degree of prematurely aborted RNA sequences (also known as "shortmers"). In some embodiments, a method according to the invention removes more than about 90%, 95%, 96%, 97%, 98%, 99% or substantially all prematurely aborted RNA sequences. In some embodiments, mRNA purified according to the present invention is substantially free of prematurely aborted RNA sequences. In some embodiments, mRNA purified according to the present invention contains less than about 5% (e.g., less than about 4%, 3%, 2%, or 1%) of prematurely aborted RNA sequences. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of prematurely aborted RNA sequences. In some embodiments, mRNA purified according to the present invention contains undetectable prematurely aborted RNA sequences as determined by, e.g., high-performance liquid chromatography (HPLC) (e.g., shoulders or separate peaks), eithidium bromide, Coomassie staining, capillary electrophoresis or Glyoxal gel electrophoresis (e.g., presence of separate lower band). As used herein, the term "shortmers", "short abortive RNA species", "prematurely aborted RNA sequences" or "long abortive RNA species" refers to any transcripts that are less than full-length. In some embodiments, "shortmers", "short abortive RNA species", or "prematurely aborted RNA sequences" are less than 100 nucleotides in length, less than 90, less than 80, less than 70, less than 60, less than 50, less than 40, less than 30, less than 20, or less than 10 nucleotides in length. In some embodiments, shortmers are detected or quantified after adding a 5'-cap, and/or a 3'-poly A tail. In some embodiments, prematurely aborted RNA transcripts comprise less than 15 bases (e.g., less than 14, 13, 12, 11, 10, 9, 8, 7, 6, 5, 4, or 3 bases). In some embodiments, the prematurely aborted RNA transcripts contain about 8-15, 8-14, 8-13, 8-12, 8-11, or 8-10 bases.

In some embodiments, a method according to the present invention removes or eliminates a high degree of enzyme reagents used in in vitro synthesis including, but not limited to, T7 RNA polymerase, DNAse I, pyrophosphatase, and/or RNAse inhibitor. In some embodiments, the present invention is particularly effective to remove T7 RNA polymerase. In some embodiments, a method according to the invention removes more than about 90%, 95%, 96%, 97%, 98%, 99% or substantially all enzyme reagents used in in vitro synthesis including. In some embodiments, mRNA purified according to the present invention is substantially free of enzyme reagents used in in vitro synthesis including. In some embodiments, mRNA purified according to the present invention contains less than about 5% (e.g., less than about 4%, 3%, 2%, or 1%) of enzyme reagents used in in vitro synthesis including. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of enzyme reagents used in in vitro synthesis including. In some embodiments, mRNA purified according to the present invention contains undetectable enzyme reagents used in in vitro synthesis including as determined by, e.g., silver stain, gel electrophoresis, high-performance liquid chromatography (HPLC), ultra-performance liquid chromatography (UPLC), and/or capillary electrophoresis, ethidium bromide and/or Coomassie staining.

In various embodiments, mRNA purified using a method described herein maintain high degree of integrity. As used herein, the term "mRNA integrity" generally refers to the quality of mRNA after purification. mRNA integrity may be determined using methods well known in the art, for example, by RNA agarose gel electrophoresis. In some embodiments, mRNA integrity may be determined by banding patterns of RNA agarose gel electrophoresis. In some embodiments, mRNA purified according to present invention shows little or no banding compared to reference band of RNA agarose gel electrophoresis. In some embodiments, mRNA purified according to the present invention has an integrity greater than about 95% (e.g., greater than about 96%, 97%, 98%, 99% or more). In some embodiments, mRNA purified according to the present invention has an integrity greater than 98%. In some embodiments, mRNA purified according to the present invention has an integrity greater than 99%. In some embodiments, mRNA purified according to the present invention has an integrity of approximately 100%. In some embodiments, a method described herein provides a composition having an increased activity, e.g., at least two-fold, three-fold, four-fold, five-fold, or more, of translated polypeptides relative to a composition having a lower percentage of full-length mRNA molecules.

In some embodiments, the purified mRNA is assessed for one or more of the following characteristics: appearance, identity, quantity, concentration, presence of impurities, microbiological assessment, pH level and activity. In some embodiments, acceptable appearance includes a clear, colorless solution, essentially free of visible particulates. In some embodiments, the identity of the mRNA is assessed by sequencing methods. In some embodiments, the concentration is assessed by a suitable method, such as UV spectrophotometry. In some embodiments, a suitable concentration is between about 90% and 110% nominal (0.9-1.1 mg/mL).

In some embodiments, assessing the purity of the mRNA includes assessment of mRNA integrity, assessment of residual plasmid DNA, and assessment of residual solvent. In some embodiments, acceptable levels of mRNA integrity are assessed by agarose gel electrophoresis. The gels are analyzed to determine whether the banding pattern and apparent nucleotide length is consistent with an analytical reference standard. Additional methods to assess RNA integrity include, for example, assessment of the purified mRNA using capillary gel electrophoresis (CGE). In some embodiments, acceptable purity of the purified mRNA as determined by CGE is that the purified mRNA composition has no greater than about 55% long abortive/degraded species. In some embodiments, residual plasmid DNA is assessed by methods in the art, for example by the use of qPCR. In some embodiments, less than 10 pg/mg (e.g., less than 10 pg/mg, less than 9 pg/mg, less than 8 pg/mg, less than 7 pg/mg, less than 6 pg/mg, less than 5 pg/mg, less than 4 pg/mg, less than 3 pg/mg, less than 2 pg/mg, or less than 1 pg/mg) is an acceptable level of residual plasmid DNA. In some embodiments, acceptable residual solvent levels are not more than 10,000 ppm, 9,000 ppm, 8,000 ppm, 7,000 ppm, 6,000 ppm, 5,000 ppm, 4,000 ppm, 3,000 ppm, 2,000 ppm, 1,000 ppm. Accordingly, in some embodiments, acceptable residual solvent levels are not more than 10,000 ppm. In some embodiments, acceptable residual solvent levels are not more than 9,000 ppm. In some embodiments, acceptable residual solvent levels are not more than 8,000 ppm. In some embodiments, acceptable residual solvent levels are not more than 7,000 ppm. In some embodiments, acceptable residual solvent levels are not more than 6,000 ppm. In some embodiments, acceptable residual solvent levels are not more than 5,000 ppm. In some embodiments, acceptable residual solvent levels are not more than 4,000 ppm. In some embodiments, acceptable residual solvent levels are not more than 3,000 ppm. In some embodiments, acceptable residual solvent levels are not more than 2,000 ppm. In some embodiments, acceptable residual solvent levels are not more than 1,000 ppm.

In some embodiments, microbiological tests are performed on the purified mRNA, which include, for example, assessment of bacterial endotoxins. In some embodiments, bacterial endotoxins are <0.5 EU/mL, <0.4 EU/mL, <0.3 EU/mL, <0.2 EU/mL or <0.1 EU/mL. Accordingly, in some embodiments, bacterial endotoxins in the purified mRNA are <0.5 EU/mL. In some embodiments, bacterial endotoxins in the purified mRNA are <0.4 EU/mL. In some embodiments, bacterial endotoxins in the purified mRNA are <0.3 EU/mL. In some embodiments, bacterial endotoxins in the purified mRNA are <0.2 EU/mL. In some embodiments, bacterial endotoxins in the purified mRNA are <0.2 EU/mL. In some embodiments, bacterial endotoxins in the purified mRNA are <0.1 EU/mL. In some embodiments, the purified mRNA has not more than 1 CFU/10 mL, 1 CFU/25 mL, 1 CFU/50 mL, 1 CFU/75 mL, or not more than 1 CFU/100 mL. Accordingly, in some embodiments, the purified mRNA has not more than 1 CFU/10 mL. In some embodiments, the purified mRNA has not more than 1 CFU/25 mL. In some embodiments, the purified mRNA has not more than 1 CFU/50 mL. In some embodiments, the purified mRNA has not more than 1 CFR/75 mL. In some embodiments, the purified mRNA has 1 CFU/100 mL.

In some embodiments, the pH of the purified mRNA is assessed. In some embodiments, acceptable pH of the purified mRNA is between 5 and 8. Accordingly, in some embodiments, the purified mRNA has a pH of about 5. In some embodiments, the purified mRNA has a pH of about 6. In some embodiments, the purified mRNA has a pH of about 7. In some embodiments, the purified mRNA has a pH of about 7. In some embodiments, the purified mRNA has a pH of about 8.

In some embodiments, the translational fidelity of the purified mRNA is assessed. The translational fidelity can be assessed by various methods and include, for example, transfection and Western blot analysis. Acceptable characteristics of the purified mRNA includes banding pattern on a Western blot that migrates at a similar molecular weight as a reference standard.

In some embodiments, the purified mRNA is assessed for conductance. In some embodiments, acceptable characteristics of the purified mRNA include a conductance of between about 50% and 150% of a reference standard.

The purified mRNA is also assessed for Cap percentage and for PolyA tail length. In some embodiments, an acceptable Cap percentage includes Cap1, % Area: NLT90. In some embodiments, an acceptable PolyA tail length is about 100-1500 nucleotides (e.g., 100, 150, 200, 250, 300, 350, 400, 450, 500, 550, 600, 650, 700, 750, 800, 850, 900, 950, and 1000, 1100, 1200, 1300, 1400, or 1500 nucleotides). Accordingly, in some embodiments an acceptable PolyA tail length is about 100 nucleotides. In some embodiments, an acceptable PolyA tail length is about 200 nucleotides. In some embodiments, an acceptable PolyA tail length is about 250 nucleotides. In some embodiments, an acceptable PolyA tail length is about 300 nucleotides. In some embodiments, an acceptable PolyA tail length is about 350 nucleotides. In some embodiments, an acceptable PolyA tail length is about 400 nucleotides. In some embodiments, an acceptable PolyA tail length is about 450 nucleotides. In some embodiments, an acceptable PolyA tail length is about 500 nucleotides. In some embodiments, an acceptable PolyA tail length is about 550 nucleotides. In some embodiments, an acceptable PolyA tail length is about 600 nucleotides. In some embodiments, an acceptable PolyA tail length is about 650 nucleotides. In some embodiments, an acceptable PolyA tail length is about 700 nucleotides. In some embodiments, an acceptable PolyA tail length is about 750 nucleotides. In some embodiments, an acceptable PolyA tail length is about 800 nucleotides. In some embodiments, an acceptable PolyA tail length is about 850 nucleotides. In some embodiments, an acceptable PolyA tail length is about 900 nucleotides. In some embodiments, an acceptable PolyA tail length is about 950 nucleotides. In some embodiments, an acceptable PolyA tail length is about 1000 nucleotides. In some embodiments, an acceptable PolyA tail length is about 1100 nucleotides. In some embodiments, an acceptable PolyA tail length is about 1200 nucleotides. In some embodiments, an acceptable PolyA tail length is about 1300 nucleotides. In some embodiments, an acceptable PolyA tail length is about 1400 nucleotides. In some embodiments, an acceptable PolyA tail length is about 1500 nucleotides.

In some embodiments, the purified mRNA is also assessed for any residual PEG. In some embodiments, the purified mRNA has less than between 10 ng PEG/mg of purified mRNA and 1000 ng PEG/mg of mRNA. Accordingly, in some embodiments, the purified mRNA has less than about 10 ng PEG/mg of purified mRNA. In some embodiments, the purified mRNA has less than about 100 ng PEG/mg of purified mRNA. In some embodiments, the purified mRNA has less than about 250 ng PEG/mg of purified mRNA. In some embodiments, the purified mRNA has less than about 500 ng PEG/mg of purified mRNA. In some embodiments, the purified mRNA has less than about 750 ng PEG/mg of purified mRNA. In some embodiments, the purified mRNA has less than about 1000 ng PEG/mg of purified mRNA.

Various methods of detecting and quantifying mRNA purity are known in the art. For example, such methods include, blotting, capillary electrophoresis, chromatography, fluorescence, gel electrophoresis, HPLC, silver stain, spectroscopy, ultraviolet (UV), or UPLC, or a combination thereof. In some embodiments, mRNA is first denatured by a Glyoxal dye before gel electrophoresis ("Glyoxal gel electrophoresis"). In some embodiments, synthesized mRNA is characterized before capping or tailing. In some embodiments, synthesized mRNA is characterized after capping and tailing.

Suitable Nucleic Acids for Described Methods

Any kind of nucleic acid can be purified using the methods described herein. In some embodiments, the nucleic acids are in vitro transcribed (IVT) mRNAs. Briefly, IVT is typically performed with a linear or circular DNA template comprising a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. In some embodiments, the IVT reaction comprises a two-step process, the first step comprising in vitro transcription of mRNA followed by a purification step, and the second step comprises capping and tailing of the in vitro transcribed mRNA followed by a second purification step. In some embodiments, the IVT reaction is a one step process which results in the in vitro transcription of capped and tailed mRNA. For example, in some embodiments, the in vitro transcription results in the production of capped and tailed mRNA which is subsequently purified. This is accomplished, for example, by using plasmids that comprise a polyT region and/or Clean-Cap®. The exact conditions will vary according to the specific application. The presence of these reagents is undesirable in the final product according to several embodiments and may thus be referred to as impurities and a preparation containing one or more of these impurities may be referred to as an impure preparation. Accordingly, in one aspect, the invention provides a method of manufacturing mRNA comprising the steps of (a) performing in vitro transcription (IVT) by mixing (i) a DNA template comprising a promoter and (ii) an RNA polymerase, to generate an impure preparation comprising full-length mRNA; (b) providing high molar salt and an amphiphilic polymer to the suspension to precipitate full-length mRNA and provide precipitated full-length mRNA in the suspension; (c) capturing the precipitated full-length mRNA by applying the suspension to a filter; and (d) washing the precipitated full-length mRNA of step (c) with an aqueous solvent to obtain a purified full-length mRNA in an aqueous solution, and (e) solubilizing the precipitated mRNA from step (d) to obtain a purified mRNA composition, wherein the purified full-length mRNA in the aqueous solution provided from step (d) is substantially free of (i) the DNA template comprising a promoter and the (ii) the RNA polymerase.

In some embodiments, in step (a) the DNA template is a linear DNA template. In some embodiments, in step (a) the polymerase is SP6 polymerase. In some embodiments, in step (a) the mixing further includes mixing a pool of ribonucleotide triphosphates. In some embodiments, in step (a) the mixing further includes an RNase inhibitor, for example an RNase I inhibitor, RNase A, RNase B, and RNase C.

In some embodiments, in step (b) the high-molar salt is GSCN. In some embodiments, in step (b) the high-molar salt comprises GSCN. In some embodiments, in step (b) the amphiphilic polymer comprises a PEG polymer. In some embodiments, in step (b) the amphiphilic polymer comprises a MTEG. In particular embodiments, in step (b) the high molar salt comprises GSCN and the amphiphilic polymer comprises a PEG having a molecular weight of about 6000 g/mol (e.g. PEG-6000) or MTEG.

In some embodiments, in step (c) the filter has a MWCO that is less than the precipitated full-length mRNA but greater than the full-length mRNA. In some embodiments, in step (c) the filter is a depth filter. In some embodiments, in step (c) the filter used with centrifugation.

In some embodiments, in step (d) the aqueous solvent comprises an amphiphilic polymer. In some embodiments, in step (d) the amphiphilic polymer in the aqueous solvent is the same as the amphiphilic polymer used in step (b). In some embodiments, in step (d) the amphiphilic polymer in the aqueous solvent is different from the amphiphilic polymer used in step (b). In some embodiments, in step (d) the amphiphilic polymer comprises a PEG polymer. In some embodiments, in step (d) the PEG polymer in the aqueous solvent is the same as the PEG polymer used in step (b). In some embodiments, in step (d) the PEG polymer in the aqueous solvent is different from the PEG polymer used in step (b).

In some embodiments, the purified full-length mRNA in the aqueous solution provided from step (e) is also substantially free of (iv) pre-aborted RNA sequences. In some embodiments, the pre-aborted RNA sequences comprise shortmers. In some embodiments, the purified full-length mRNA in the aqueous solution provided from step (e) is also substantially free of (v) double-stranded RNA (dsRNA). In some embodiments, the purified full-length mRNA in the aqueous solution provided from step (e) is also substantially free of (iv) pre-aborted RNA sequences and (v) double-stranded RNA (dsRNA).

In some embodiments, in step (a) the RNA polymerase is SP6 polymerase and the purified full-length mRNA in the aqueous solution provided from step (e) is also substantially free of (v) double-stranded RNA (dsRNA).

In some embodiments, this method of manufacture uses no chromatography to yield the highly pure mRNA. In some embodiments, this method of manufacture uses no alcohol-based solvents to yield the highly pure mRNA. In some embodiments, this method of manufacture uses no chromatography and no alcohol-based solvents to yield the highly pure mRNA.

According to various embodiments, the present invention is used to purify in vitro synthesized mRNA of a variety of lengths. In some embodiments, the present invention is used to purify in vitro synthesized mRNA of greater than about 1 kb, 1.5 kb, 2 kb, 2.5 kb, 3 kb, 3.5 kb, 4 kb, 4.5 kb, 5 kb, 6 kb, 7 kb, 8 kb, 9 kb, 10 kb, 11 kb, 12 kb, 13 kb, 14 kb, or 15 kb in length. In some embodiments, the present invention is used to purify mRNA containing one or more modifications that typically enhance stability. In some embodiments, one or more modifications are selected from modified nucleotide, modified sugar phosphate backbones, 5' and/or 3' untranslated region. In some embodiments, the present invention is used to purify in vitro synthesized mRNA that is unmodified.

Typically, mRNAs are modified to enhance stability. Modifications of mRNA can include, for example, modifications of the nucleotides of the RNA. A modified mRNA according to the invention can thus include, for example, backbone modifications, sugar modifications or base modifications. In some embodiments, antibody encoding mRNAs (e.g., heavy chain and light chain encoding mRNAs) may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy-acetic acid methyl ester, 5-methylaminomethyl-uracil, 5-methoxyaminomethyl-2-thio-uracil, 5'-methoxycarbonyl-methyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs that are purified using the methods described herein include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G.

While mRNA provided from in vitro transcription reactions may be desirable in some embodiments, other sources of mRNA are contemplated as within the scope of the invention including wild-type mRNA produced from bacteria, fungi, plants, and/or animals.

In some embodiments, mRNAs for purification in the methods described herein include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

The present invention can be used to purify mRNAs that encode any protein. Non-limiting examples of mRNAs purified using the methods described herein are presented in the section below.

EXAMPLES

Example 1. Synthesis of mRNA

IVT Reaction Conditions

In the following examples, unless otherwise described, mRNA was synthesized via in vitro transcription (IVT) using either T7 polymerase or SP6 polymerase. Briefly, in the SP6 polymerase IVT reaction, for each gram of mRNA transcribed, a reaction containing 20 mg of a linearized double stranded DNA plasmid with an RNA polymerase specific promoter, SP6 RNA polymerase, RNase inhibitor, pyrophosphatase, 5 mM NTPs, 10 mM DTT and a reaction buffer (10×-250 mM Tris-HCl, pH 7.5, 20 mM spirmidine, 50 mM NaCl) was prepared with RNase free water then incubated at 37 C for 60 min. The reaction was then quenched by the addition of DNase I and a DNase I buffer (10×-100 mM Tris-HCl, 5 mM $MgCl_2$ and 25 mM $CaCl_2$), pH 7.6) to facilitate digestion of the double stranded DNA template in preparation for purification. The final reaction volume was 204 mL.

5' Cap

Unless otherwise described the IVT transcribed mRNA was capped on its 5' end either by including cap structures as part of the IVT reaction or in a subsequent enzymatic step. For capping as part of the IVT reaction, a cap analog can be incorporated as the first "base" in the nascent RNA strand. The cap analog may be Cap 0, Cap1, Cap 2, $^{m6}A_m$, or unnatural caps. Alternatively, uncapped and purified in vitro transcribed (IVT) mRNA can be modified enzymatically following IVT to include a cap, e.g., by the addition of a 5' $N^7$-methylguanylate Cap 0 structure using guanylate transferase and the addition of a methyl group at the 2' O position of the penultimate nucleotide resulting in a Cap 1 structure using 2' O-methyltransferase as described by Fechter, P.; Brownlee, G. G. "Recognition of mRNA cap structures by viral and cellular proteins" J. Gen. Virology 2005, 86, 1239-1249.

3' Tail

Unless otherwise described, the IVT transcribed mRNA was tailed on its 3' end either by including a tail template in the linearized plasmid, which tails the mRNA as part of the IVT reaction, or in a subsequent enzymatic step. For tailing as part of the IVT reaction, incorporation of a poly-T or similar tailing feature into the pDNA template is performed such that the polyA tail or similar appropriate tail is formed on the mRNA as part of the IVT process. Alternatively, a poly-A tail can be added to the 3' end of the IVT-produced mRNA enzymatically following the IVT reaction, e.g., using poly-A polymerase.

Example 2. Purification of mRNA Via VOC-Free, Polymer-Induced Precipitation of mRNA This example illustrates that polymer can be used instead of a volatile organic compound (VOC) such as ethanol during the mRNA precipitation step of mRNA purification. Such polymer-induced precipitation method provides a final yield and purity level suitable for therapeutic use.

Three 5 mg batches of CFTR mRNA were synthesized via IVT synthesis as described in Example 1, with each batch precipitated in three different conditions described below.

Condition 1: Ethanol and GSCN (Experimental Control)

1 volume of mRNA was mixed with 2.3 volumes of 5M GSCN-10 mM DTT buffer with final concentration of 2M GSCN. Then 1.7 volumes of 100% of ethanol were added to the suspension, with final concentration of ethanol at 34%.

Condition 2: PEG-6000 and GSCN (Ethanol Free Polymer-Induced Precipitation)

1 volume of mRNA was mixed with 2.3 volumes of 5M GSCN-10 mM DTT buffer with final concentration of 2M GSCN. Then 1.7 volumes of 50% of PEG-6000 were added to the suspension, with final concentration of PEG-6000 at 17%.

Condition 3: PEG-6000 and NaCl (Ethanol Free Polymer-Induced Precipitation)

The precipitation step was carried out in conditions described in Schmitz et al., Notes & Tips, Anal Biochem. (2006) 311-313. 1 volume of mRNA was mixed with NaCl to final concentration of NaCl at 500 mM. Then 50% of PEG-6000 were added to the suspension, with final concentration of PEG-6000 at 19%.

Figure 2:
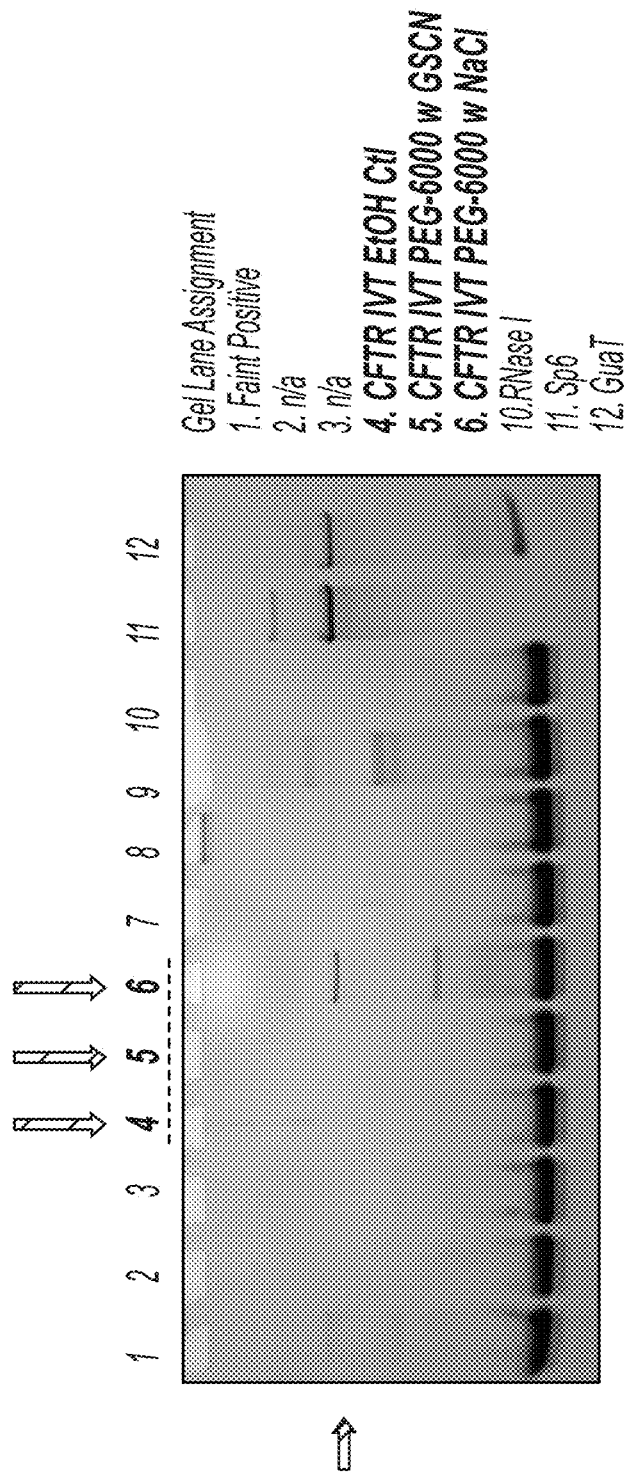
FIG. 2 shows a silver stain gel of mRNA purified with different precipitation conditions. The silver stain gel was used to show the presence of contaminating process enzymes. The gel band indicated by the arrow on the left side of the gel designates the migration of the SP6 RNA polymerase.

The mRNA samples, precipitated in each condition, were captured on a Qiagen RNeasy maxi column, washed twice with 10 ml of 80% ethanol, and dissolved in 5 ml of RNase-free water. The concentration of the dissolved mRNA samples was quantified by NanoDrop2000 spectrophotometer using absorbance at 260 nm. Yields for each precipitation condition are shown in FIG. 1. Additionally, the presence of residual process enzymes was detected via silver stain described below, and the results are shown in FIG. 2.

The data shows that the three precipitation conditions resulted in similar mRNA yield after purification. Precipitation conditions 1 and 2 resulted in highly pure mRNA samples, without observable process enzymes by the silver stain, as shown in FIG. 2. However, polymer-induced precipitation via PEG-6000 and NaCl (Condition 3), resulted in sample showing banding consistent with the presence of process enzymes, which would require additional purification steps to be acceptable for therapeutic use. The data here support that mRNA precipitation by condition 2 can be used in purifying mRNA to achieve a sufficient yield and purity level for therapeutic use.

mRNA Purity-Residual Process Enzyme Detection (Silver Stain)

mRNA purity with respect to residual IVT enzymes and optionally cap and/or tail enzymes was assessed by silver stain. In particular, each of the following residual process enzymes can be detected using this approach: RNA polymerase, RNA inhibitor, Pyrophosphatase, Guanylyltransferase (GuaT), 2'OM, and PolyA polymerase, as well as the enzyme, RNase I, which is used as part of the silver stain gel preparation. In particular, silver stain gels were run according to the Invitrogen kit with the following pre-stain sample preparations. 15.50 of 1 mg/ml RNA treated with 40 of RNaseI (100 U/mL, Invitrogen) for 30 minutes at 37 C. Samples were prepared in Invitrogen LDS loading buffer with reducing reagent and ultimately loaded on 10% Bis-Tris gels. Electrophoresis was carried out at 200V for 35 mins. Gels were stained using the Silver Quest staining kit and developed for 8 mins. Samples comprising purified mRNA were considered substantially free of a particular process enzyme if a band for the particular process enzyme was not visible.

Example 3. Testing Polymer Ratio Ranges in Polymer-Induced Precipitation of mRNA This example illustrates that, according to various embodiments, different ratios of polymer can be used in polymer-induced precipitation of mRNA to purify mRNA suitable for therapeutic use.

Seven 5 mg batches of CFTR mRNA were synthesized via IVT synthesis as described in above, with each batch being precipitated in different conditions shown in Table 1 below.

TABLE 1

Precipitation conditions for mRNA purification

| Sample | Final % of Ethanol | Ratio of 50% PEG-6000 added | Final % of PEG-6000 | Final Concentration of GSCN (M) |
|---|---|---|---|---|
| 1 | 34 | 0 | 0 | 2.3 |
| 2 | 0 | 0.5 | 7 | 3.0 |
| 3 | 0 | 1.0 | 12 | 2.7 |
| 4 | 0 | 1.5 | 16 | 2.4 |
| 5 | 0 | 2.0 | 19 | 2.2 |
| 6 | 0 | 2.5 | 22 | 2.0 |
| 7 | 0 | 3.0 | 24 | 1.8 |

Figure 3:
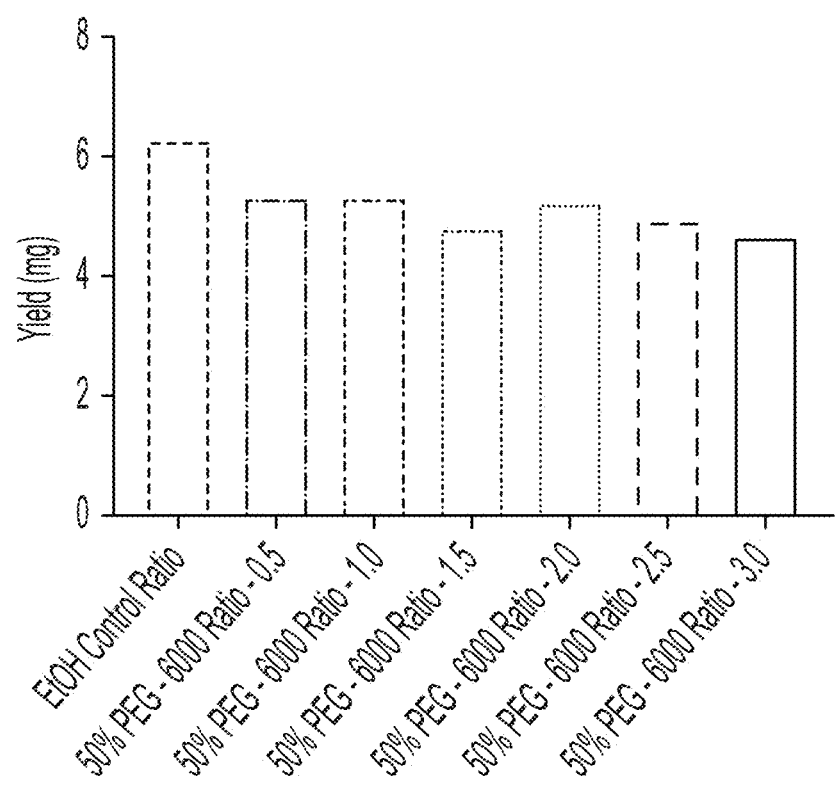
FIG. 3 shows the yield of mRNA purified by polymer-induced precipitation with various PEG-6000 ratio.
Figure 4:
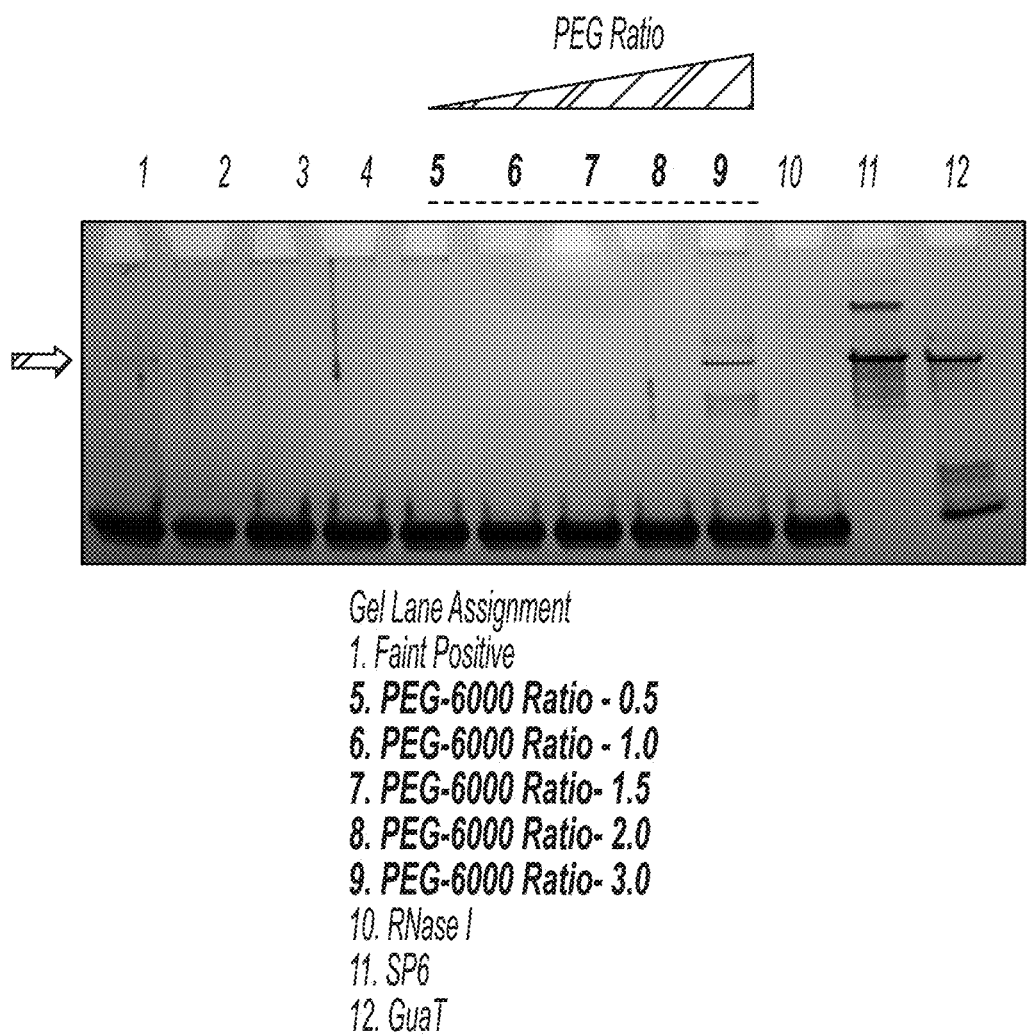
FIG. 4 shows the silver stain gel of mRNA purified via polymer-induced precipitation with various PEG-6000 ratios.

The mRNA samples, precipitated in each condition, were captured on a Qiagen RNeasy maxi column, washed twice with 10 ml of 80% ethanol, and dissolved in 5 ml of RNase-free water. The concentration of the dissolved mRNA samples was quantified by NanoDrop2000 spectrophotometer using absorbance at 260 nm. Yields for each precipitation condition are shown in FIG. 3. Additionally, the presence of residual process enzymes was detected via silver stain described in Example 2, and the results are shown in FIG. 4.

The data shows that the all six conditions of purified mRNA that used polymer-induced precipitation of mRNA resulted in high mRNA yield after purification, which was similar to the traditional ethanol precipitation method (FIG. 3). Additionally, mRNA samples purified via polymer-induced precipitation with final PEG concentrations less than 20% PEG concentration (or less than 2.0 ratio of 50% PEG-6000) resulted in highly pure mRNA samples, without observable process enzymes by the silver stain shown in FIG. 4 (lanes 5-8). However, samples with mRNA purified via polymer-induced precipitation having a final PEG-6000 concentration greater than 20% showed residual process enzymes (Lane 9). Interestingly, polymer-induced precipitation with 24% PEG-6000 resulted in more residual process enzymes in the purified sample than in the sample with 22% PEG-6000 polymer-induced precipitation. Without wishing to be bound by any particular theory, it is contemplated that higher % PEG-6000 facilitates precipitation of both nucleic acid and process enzymes.

Together, the data here further support that mRNA purification via polymer-induced precipitation is a viable method for purifying mRNA to achieve a sufficient yield and purity level for therapeutic use. The polymer-induced precipitation with final concentration of PEG-6000 between 7-24% results in efficient mRNA precipitation and recovery. For the remaining examples, final PEG-6000 concentration 12% was used in polymer-induced precipitation.

Example 4. Ethanol-Free Purification of mRNA and Effect of Different Polymers in Wash Step This example illustrates that polymer can be used during both mRNA precipitation and washing steps, without any VOCs such as ethanol, to purify mRNA with a yield and purity level suitable for therapeutic use.

Twelve 5 mg batches of CFTR mRNA were synthesized via IVT synthesis and 5' caps and 3' polyA tails were added as described in Example 1. The resulting twelve 5 mg of IVT mRNA batches were each precipitated via polymer-induced precipitation. For each 5 mg batch, 5M GSCN-10 mM DTT buffer was added to a final concentration of GSCN at 2.7M. Then 50% of PEG-6000 was added to the suspension to a final concentration of PEG-6000 at 12%. The precipitated mRNA samples were captured on Qiagen RNeasy maxi columns and washed twice with 10 ml of one of the following polymer wash buffers listed in Table 2 below, instead of 80% ethanol. No VOCs or alcohol at all was used in the purification of the IVT synthesized mRNA. In particular, no VOCs or alcohol was used in the precipitation step or in the wash step.

TABLE 2

Polymer wash buffers

| Sample | Polymer | Final % of polymer in wash |
|---|---|---|
| 1 | Triethylene Glycol (TEG) | 70 |
| 2 | Triethylene Glycol (TEG) | 80 |
| 3 | Triethylene Glycol (TEG) | 90 |
| 4 | Triethylene Glycol (TEG) | 100 |
| 5 | 100% PEG-400 | 70 |
| 6 | 100% PEG-400 | 80 |
| 7 | 100% PEG-400 | 90 |
| 8 | 100% PEG-400 | 100 |
| 9 | 50% PEG-6000 | 35 |
| 10 | 50% PEG-6000 | 40 |
| 11 | 50% PEG-6000 | 45 |
| 12 | 50% PEG-6000 | 50 |

Figure 5:
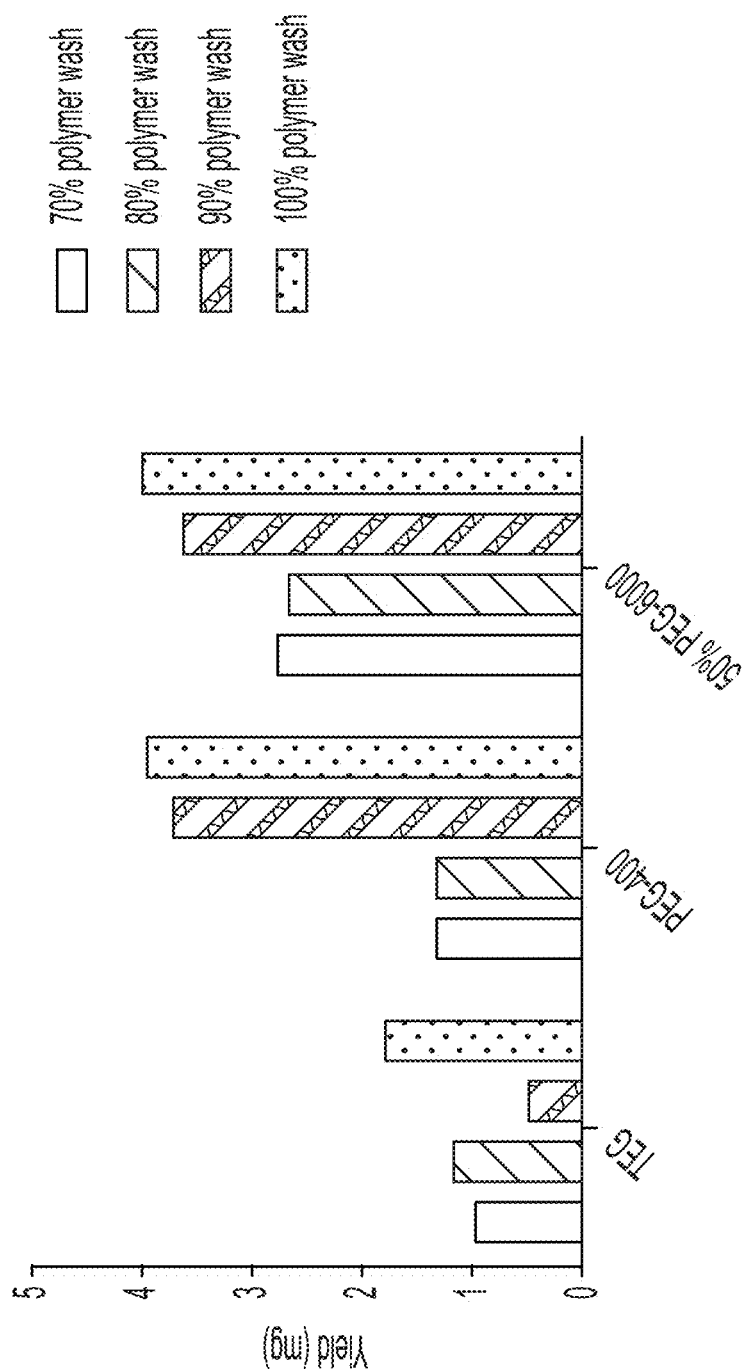
FIG. 5 shows the yield of ethanol-free mRNA purification via polymer-induced precipitation and polymer wash, for different polymer wash buffers and concentrations used.
Figure 6:
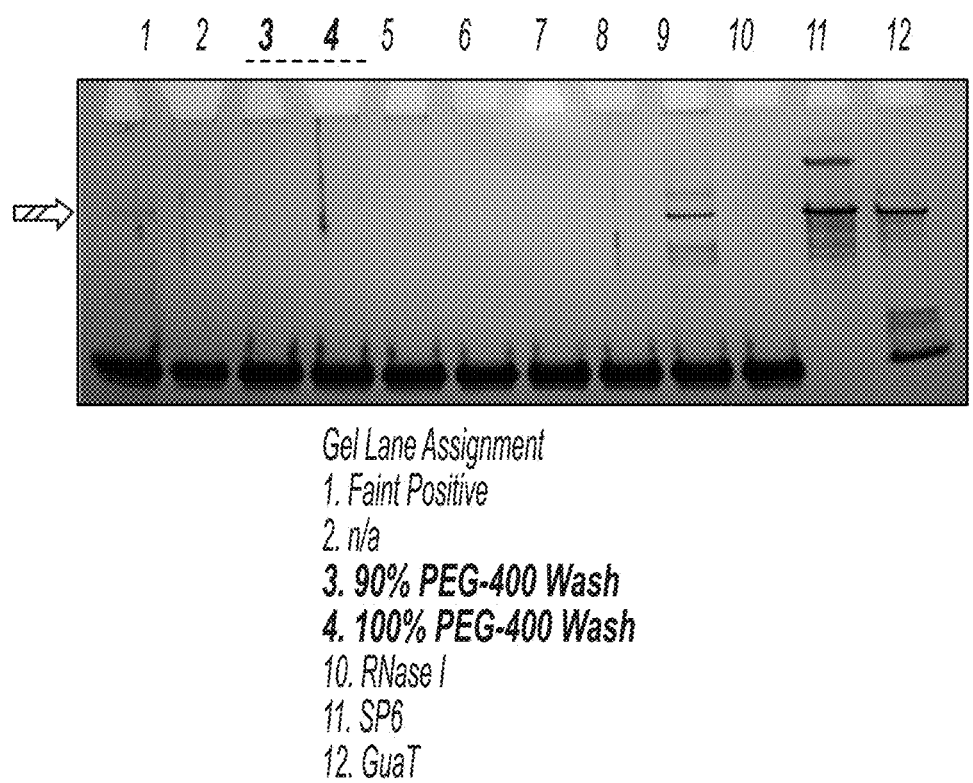
FIG. 6 shows a silver stain gel of ethanol-free mRNA purification polymer-induced precipitation and polymer wash, for 90% and 100% PEG-400 wash buffers (lane 3 and 4 respectively).

The twelve samples were dissolved in 5 ml of RNase-free water and the concentration was quantified by NanoDrop2000 spectrophotometer using absorbance at 260 nm. Yields for each precipitation condition are shown in FIG. 5. Additionally, the presence of residual process enzymes was detected via silver stain described in Example 2, and the results are shown in FIG. 6.

As shown in FIG. 5, a strong correlation was found between the percent of polymer in the wash buffer and the amount of mRNA recovered were observed. Without wishing to be bound by any particular theory, it is contemplated that the addition of water to these wash buffers results the solubilization of the mRNA during these wash steps.

Overall, the data show that, surprisingly, mRNA can be purified completely ethanol-free, via polymer-induced precipitation followed by polymer wash to achieve a surprising yield and purity level suitable for therapeutic use. The wash buffer with PEG-400 at a final concentration between 90-100% resulted in high yield as shown in FIG. 5, and highly pure mRNA samples, without observable process enzymes by the silver stain shown in FIG. 6 (lanes 3-4). PEG-400 has the lowest viscosity of the buffers tested, making it amendable to use in different systems at different scales. Together these data demonstrated that ethanol-free mRNA purification via polymer-induced precipitation and polymer wash described herein may be used to efficiently purify high quality mRNA with resulting yield recoveries, integrity profiles, purity and functionality that is equivalent or superior to the industry-standard mRNA purification methods that employ VOCs such as alcohols, including ethanol. Moreover, the present invention has a significant added benefit of scalability and safety, which is unavailable with the existing industry-standard methods that employ VOCs such as alcohols, including ethanol.

Example 5. Ethanol-Free Purification of OTC and CFTR mRNAs and Analysis

This example illustrates that ethanol-free mRNA purification method, described above, can be used to purify mRNA regardless of its construct size or nucleotide composition. Additionally, the purified mRNA according to methods described herein, results in high yield, purity, and integrity.

5 mg batches of OTC mRNA (1400 nt) and 5 mg of CFTR mRNA (4600 nt) were synthesized via IVT synthesis as described in Example 1. The resulting IVT mRNA samples were precipitated via polymer-induced precipitation. For each 5 mg batch, 5M GSCN-10 mM DTT buffer was added to a final concentration of GSCN at 2.7M. Then 50% of PEG-6000 was added to the suspension, to a final concentration of PEG-6000 at 12%. The precipitated mRNA samples were captured on Qiagen RNeasy maxi columns and washed twice with 10 ml of 90% PEG-400 wash buffer. The washed samples were dissolved in 5 ml of RNase-free water, buffer exchanged into ultra-pure water using 100 kD Amicon spin columns, and concentrated to 2 mg/ml.

The purified and concentrated IVT mRNAs were then capped and tailed via an enzymatic step as described in Example 1. The mRNAs with 5' cap and 3' tail were purified via polymer-induced precipitation and polymer wash, free of ethanol. In particular, for the precipitation step for each batch, 5M GSCN-10 mM DTT buffer was added to a final concentration of GSCN at 2.7M. Then 50% of PEG-6000 was added to the suspension, to final concentration of PEG-6000 at 12%. The precipitated mRNA samples were captured on Qiagen RNeasy maxi columns and washed twice with 10 ml of 90% PEG-400 wash buffer. The washed samples were dissolved in 5 ml of RNase-free water, buffer exchanged into ultra-pure water using 100 kD Amicon spin columns, and concentrated to 1 mg/ml.

Figure 7:
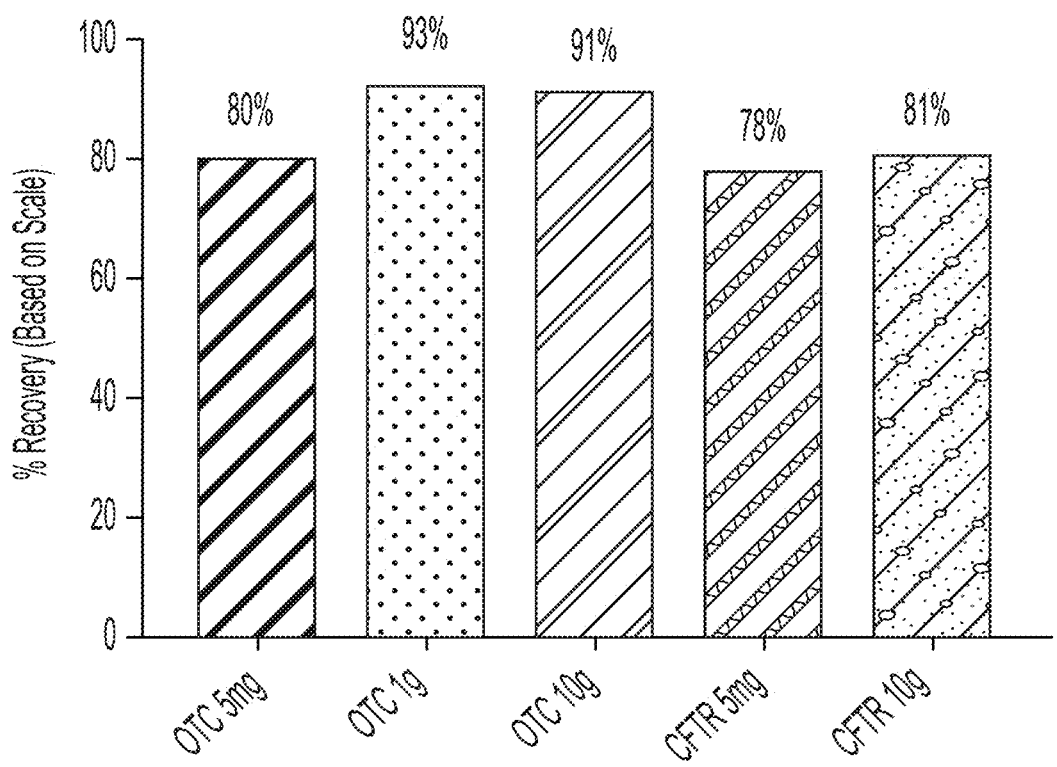
FIG. 7 shows percent recovery of ethanol-free mRNA purification via polymer-induced precipitation and polymer wash, for different mRNA constructs (OTC and CFTR), at 5 mg, 1 g and 10 g scales.

Yields for each final mRNA product were determined, as shown in FIG. 7. The data demonstrated that mRNA yields for 5 mg scale of OTC and CFTR mRNAs were 80 and 78%, respectively. These values were within or above the yield of industry-standard mRNA purification methods.

Figure 8:
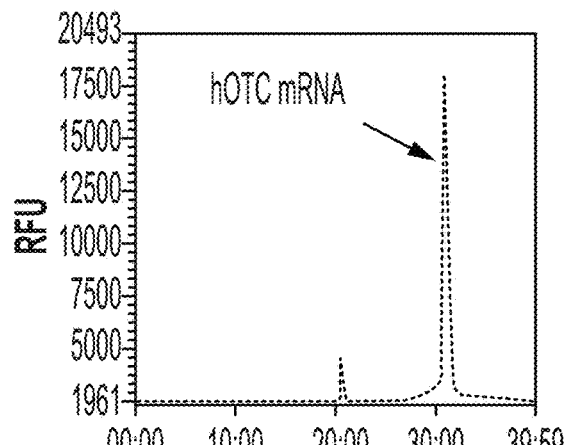
FIG. 8 shows capillary electrophoresis (CE) profiles, demonstrating the integrity of the mRNA purified via polymer-induced precipitation and polymer wash for different mRNA constructs (OTC and CFTR), at 5 mg, 1 g and 10 g scales.
Figure 8:
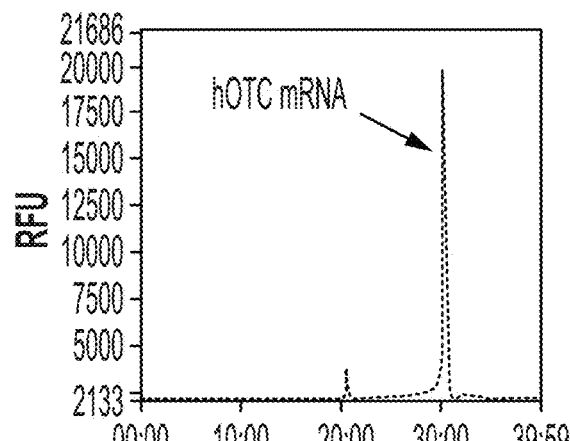
Figure 8:
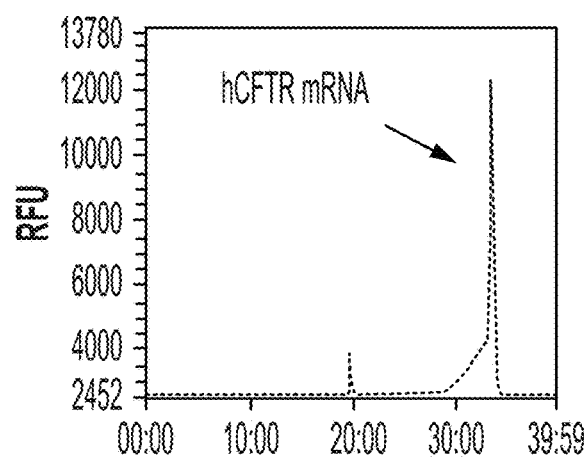
Figure 8:
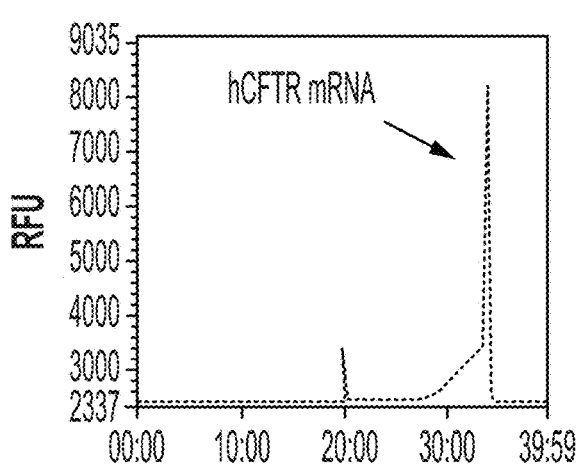
Figure 8:
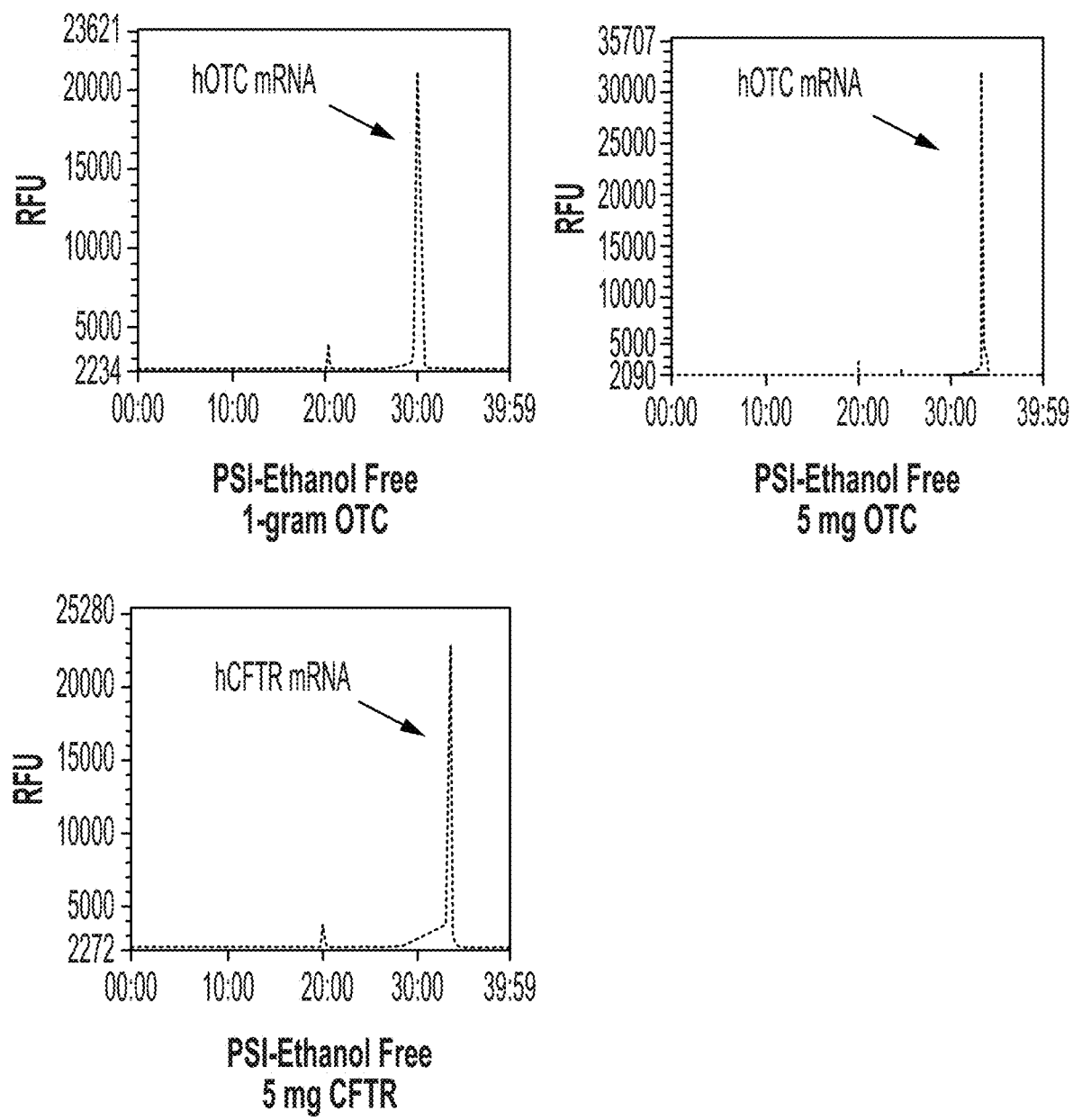
Figure 10:
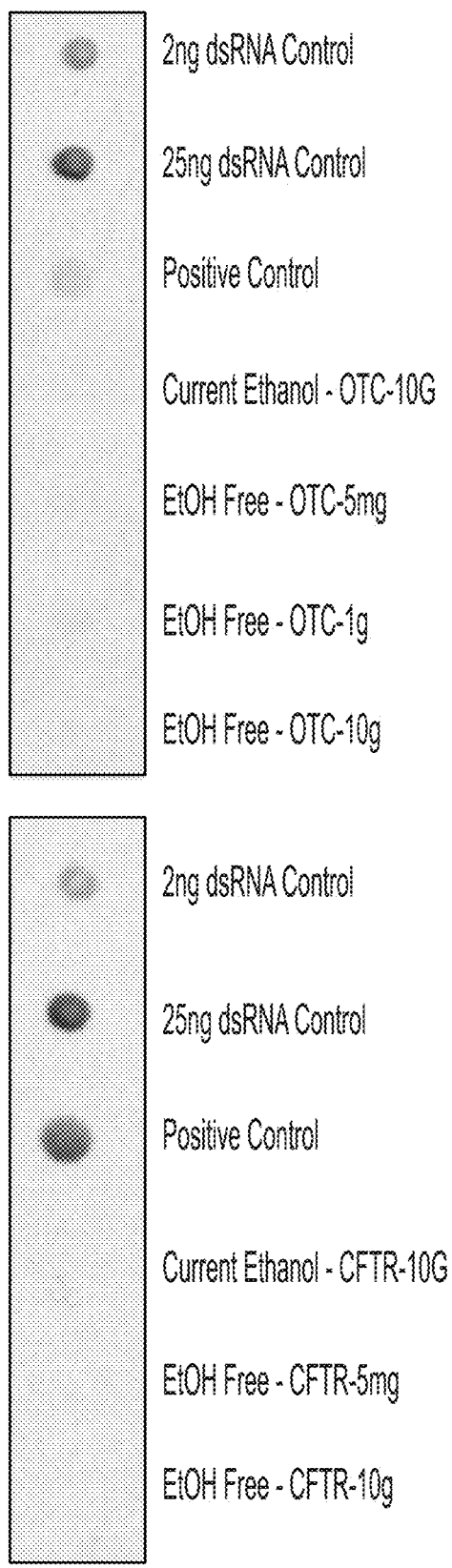
FIG. 10 is a series of dot blots that show the presence or absence of dsRNA following purification of ornithine carbamoyltransferase (OTC) mRNA at 10 gram, 5 mg, or 1 g scales. The purification conditions are indicated above the gel and include: positive control lanes (2 ng dsRNA Control, 25 ng dsRNA Control, positive control), ethanol-based purification of 10 g OTC mRNA, and ethanol-free purification of 10 g, 5 g or 1 g of OTC mRNA.

The purity and integrity of the final mRNA product were analyzed as described below. The integrity and polyA tail length were assessed using Capillary Electrophoresis, as shown in FIG. 8. The results indicated that the final products from 5 mg scale purification of both OTC and CFTR mRNAs have a well-defined peak similar to that of the control (Current Ethanol 10-gram OTC). Additionally, the tail lengths for both constructs were within the target range of 500 nt (OTC=468 nt and CFTR=649 nt). The presence of residual process enzymes, as assessed via silver stain, was not detected in the 5 mg scale purification of either mRNA construct. The purity was further confirmed via dsRNA J2 dot blot, as described below. The results, as shown in FIG. 10, demonstrated that dsRNA was not detected in the final product of either construct. Lastly, ELISA was used to confirm that PEG was completely removed during the dialysis step, as shown in Table 3.

TABLE 3

Quantification of PEG in final mRNA sample using ELISA

| | PEG (ng/mg RNA) | | |
| --- | --- | --- | --- |
| Sample | Neat | 1:10 Dilution | 1:100 Dilution |
| Current Ethanol 10-gram OTC | BQL | BQL | BQL |
| Ethanol Free 5 mg OTC | BQL | BQL | BQL |
| Ethanol Free 1-gram OTC | BQL | BQL | BQL |
| Ethanol Free 10-gram OTC | BQL | BQL | BQL |
| Current Ethanol 10-gram CFTR | BQL | BQL | BQL |
| Ethanol Free 5 mg CFTR | BQL | BQL | BQL |
| Ethanol Free 10-gram CFTR | BQL | BQL | BQL |
| Quantifiable Limit | 10 ng PEG/mg of RNA | 100 ng PEG/mg of RNA | 1000 ng PEG/mg of RNA |

BQL = Below Detectable Limit

Together, the data showed the ethanol-free purification of mRNA via polymer-induced precipitation and polymer wash, described herein, can be applied to purification of mRNAs of different length and constructs. The mRNAs purified by methods described herein meets or exceeds historical large-scale mRNA lots with regards to the critical release characteristics described above. Thus the high yield, integrity and purity level of the method described herein is suitable for therapeutic use.

Analysis of Purified mRNA Integrity

RNA Integrity Analysis (Fragment Analyzer—Capillary Electrophoresis)

RNA integrity and tail length were assessed using a CE fragment analyzer and the commercially available RNA detection kit. Analysis of peak profiles for integrity and size shift for tail length were performed on raw data as well as normalized data sets.

mRNA Cap Species Analysis (HPLC/MS)

Cap species present in the final purified mRNA product were quantified using the chromatographic method described in U.S. Pat. No. 9,970,047. This method is capable of accurately quantifying uncapped mRNA as a percent of total mRNA. This method also can quantify amounts of particular cap structures, such as CapG, Cap0 and Cap 1 amounts, which can be reported as a percentage of total mRNA.

dsRNA Detection (J2 Dot Blot)

The presence of dsRNA in individual mRNA samples was measured using the J2 anti-dsRNA dot blot previously describe by Kariko et al, *Nucleic Acids Research*, 2011. 39, No. 21. Briefly, either 200 ng of RNA or 25 ng of dsRNA control were blotted onto super charged Nytran. The blots were dried, blocked with 5% non-fat dry milk then probed with 1 μg of J2 antibody per blot. Blots were washed, probed with an HRP-conjugated donkey anti-mouse before being washed again. Blots were detected with ECL plus western blot detection reagent and images captured on film. Samples comprising purified mRNA were considered substantially free of dsRNA if the respective blot showed no visibly darker coloration as compared to a control that lacked any dsDNA.

PEG Quantitation/Detection ELISA (Abcam Kit)

The presence of various molecular weight PEG species in mRNA samples was determined using the PEG-ELISA kit from Abcam. Briefly, a competitive inhibition ELISA was used that detects PEG in samples as low as 10 ng/mL and can accurately quantify large molecular weight PEG at that level. mRNA samples purified using standard ethanol-based precipitation methods as well as the below mentioned ethanol-free method at neat, 1/10 and 1/100 dilutions. The limit of detection is 10 ng/mg of RNA, 100 ng/mg of RNA, and 1 ug/mg of RNA at neat concentration, at 1/10 dilution, and at 1/100 dilution respectively.

Example 6. Ethanol-Free Purification of mRNA at 1-Gram and 10-Gram Scale

This example illustrates that the ethanol-free mRNA purification method, described above, can be used to purify mRNA at the necessary scale and quality needed for therapeutic use. The mRNA purified at 1- and 10-gram scale according to methods described herein, results in high yield, purity, and integrity, demonstrating the scalability of the method.

OTC mRNA was synthesized at 1- and 10-gram scale, and CFTR mRNA was synthesized at 10-gram scale via IVT synthesis as described in Example 1. The resulting IVT mRNA samples were precipitated via polymer-induced precipitation. For each mRNA sample, 5M GSCN-10 mM DTT buffer was added, to a final concentration of GSCN at 2.7M. Then 50% of PEG-6000 was added to the suspension, to a final concentration of PEG-6000 at 12%. Solka-Floc cellulose-based filtering aid was added to the precipitated mRNA at a ratio of 10 to 1, filter aid to RNA ratio (wt/wt) and mixed well. The precipitated mRNA samples at 1-gram scale, with the filter aid, were captured on a 0.22 μm polyethersulfone (PES) vacuum filter flask. The precipitated mRNA samples at 10-gram scale, with the filter aid, were captured on H300P filtering centrifuge with 1 μm polypropylene filter bag. The 1- and 10-gram mRNA samples were then washed twice with 1 L or 10 L of 90% PEG-400 wash buffer. The washed and precipitated mRNA was removed from the filter either manually or by filtration through the H300P filtering centrifuge with 1 μm polypropylene filter bag. The washed and precipitated mRNA then was solubilized in 1 L or 10 L of RNase-free water, buffer exchanged into ultra-pure water using 100 kD Spectrum TFF column (mPES) and concentrated to 2 mg/ml.

The purified and concentrated IVT mRNAs were then capped and tailed by the enzymatic reaction as described in Example 1. The mRNAs with 5' cap and 3' tail were purified via polymer-induced precipitation and polymer wash, free of ethanol. For each, 5M GSCN-10 mM DTT buffer was added, to a final concentration of GSCN at 2.7M. Then 50% of PEG-6000 was added to the suspension, to a final concentration of PEG-6000 at 12%. Solka-Floc cellulose-based filtering aid was added to the precipitated mRNA at a ratio of 10 to 1, filter aid to RNA ratio (wt/wt), and mixed well. The precipitated mRNA was washed twice with 1 L or 10 L of 90% PEG-400 wash buffer. The washed mRNA samples were removed from the filter either manually or by filtration through the H300P filtering centrifuge with 1 μm polypropylene filter bag. The mRNA samples were dissolved in 1 L or 10 L of RNase-free water, buffer exchanged into ultra-pure water using 100 kD Spectrum TFF column (mPES) and concentrated to 1 mg/ml.

Yields for each final mRNA product were determined, as shown in FIG. 7. The data demonstrated that mRNA yields for 1- and 10-gram scale of OTC mRNA and 10-gram scale of CFTR mRNAs were all above 80%, and as high as 93%. These values were within or above the yield of industry-standard mRNA purification method.

Figure 9:
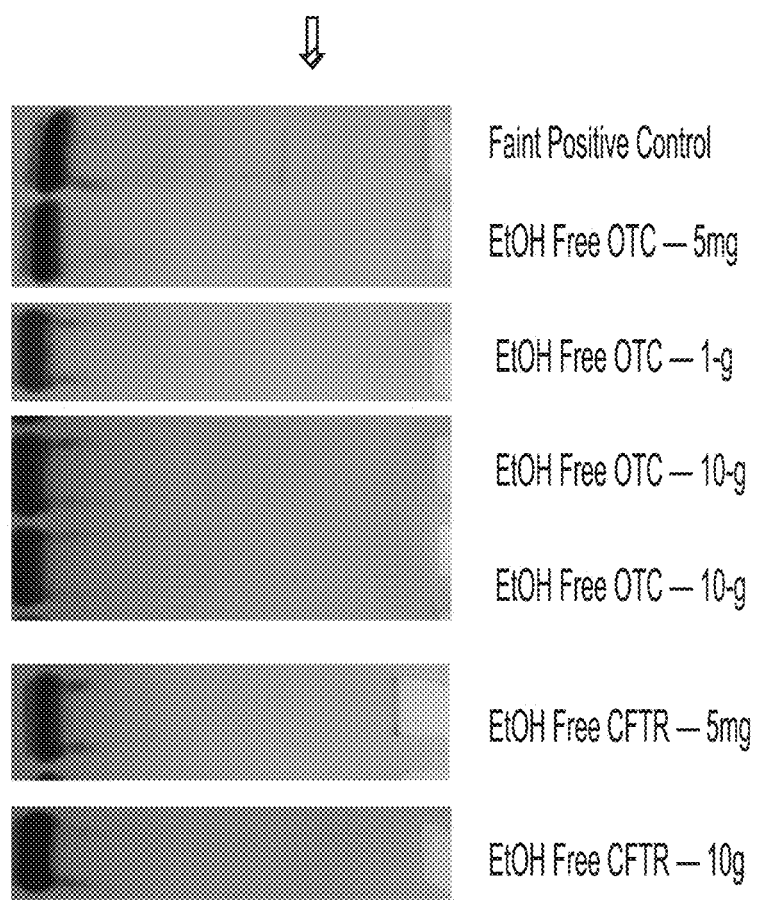
FIG. 9 shows the silver stain gel of ethanol-free mRNA purification via polymer-induced precipitation and polymer wash, for different mRNA constructs (OTC and CFTR), at 5 mg, 1 g and 10 g scales.

The purity and integrity of the final mRNA product was analyzed as described above. The integrity and poly A tail length was assessed using Capillary Electrophoresis, as shown in FIG. 8. The results showed that the final products from 1- and 10-gram scale purification of OTC and CFTR mRNAs have a well-defined peak similar to that of the control (Current Ethanol 10-gram OTC). For 10-gram scale purified mRNA, cap species were quantified using the HPLC-MS assay as described in Example 2. Additionally, the tail lengths for both constructs were within the target ranges (OTC at 1-gram=306 nt; OCT at 10-gram=158 nt; CFTR at 10-gram=712 nt). The presence of residual process enzymes, as assessed via silver stain, was not detected in both 1- and 10-gram scale purification of both mRNA constructs, as shown in FIG. 9. The purity was further confirmed via dsRNA J2 dot blot, as described in the Example 5. The results, as shown in FIG. 10, demonstrated that dsRNA was not detected in the final product at both 1- and 10-gram scale. Lastly, ELISA was used to confirm that PEG was completely removed during the dialysis step.

Together, the data demonstrate the scalability of the ethanol-free purification of mRNA via polymer-induced precipitation and polymer wash to purify mRNA at the necessary scale and quality required for clinical therapeutic use. The mRNAs purified at 1- and 10-grams scale by methods described herein meets or exceeds historical large-scale mRNA lots with regards to the critical release characteristics described above, demonstrating the suitability of the method for use in mRNA manufacturing and therapeutics.

The present invention can be used to purify mRNAs that encode any protein. Non-limiting examples of mRNAs purified using the methods are described.

Example 7. Ethanol-Free Purification of mRNA and Effect of MTEG in Wash Step

This example illustrates that the amphiphilic polymer MTEG can be used during the washing steps, without any VOCs such as ethanol, to purify mRNA with a yield and purity level suitable for therapeutic use.

Table 4 displays the characteristics of the MTEG relative to the polymers tested in the preceding examples. Despite having a molecular weight similar to TEG, MTEG has a much lower viscosity due to the presence of a methyl group. This means MTEG has a viscosity much closer to water, meaning that it is easier to pump. Moreover, it is classified as "safe" by the US Food and Drug Administration (FDA), whereas TEG, PEG-400, and PEG-6000 (50%) are classified as "generally recognized as safe" (GRAS).

TABLE 4

| Polymer characteristics | | | |
|---|---|---|---|
| MTEG | 164.2 | 7.0 | Safe |
| TEG | 150.2 | 42.4 | GRAS |
| PEG-400 | 400 | 90.0 | GRAS |
| PEG-6000 (50%) | 6000 | 88.0 | GRAS |

Five 5 mg batches of CFTR mRNA were synthesized via IVT synthesis and 5' caps and 3' polyA tails were added as described in Example 1. The resulting five 5 mg of IVT mRNA batches were each precipitated via polymer-induced precipitation. The volume ratio of mRNA, GSCN (5M GSCN-10 mM DTT buffer) and MTEG (100% weight/volume) in the precipitation reaction was 1:2.3:1. The precipitated mRNA samples were captured on Qiagen RNeasy maxi columns and washed twice with 2.5 ml of one of the following MTEG wash buffers listed in Table 5 below, instead of 80% ethanol. No VOCs or alcohol were used in the purification of the IVT synthesized mRNA. In particular, no VOCs or alcohol were used in the precipitation step or in the wash step.

TABLE 5

| Polymer wash buffers | | |
|---|---|---|
| Sample | Polymer | Final % of polymer in wash |
| 1 | MTEG | 75 |
| 2 | MTEG | 80 |
| 3 | MTEG | 85 |
| 4 | MTEG | 90 |
| 5 | MTEG | 95 |

The five samples were dissolved in 5 ml of RNase-free water and the concentration was quantified by Nano-Drop2000 spectrophotometer using absorbance at 260 nm. The concentration of RNA recovered is displayed in FIG. 11.

Figure 11:
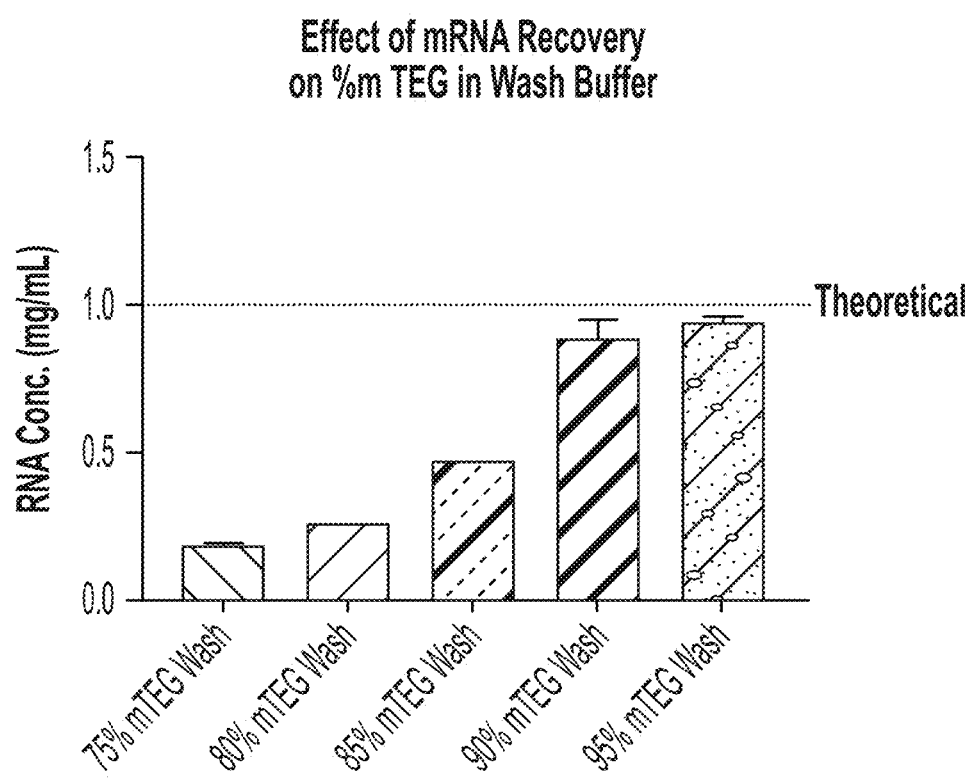
FIG. 11 shows the recovery of mRNA purified by polymer-induced precipitation and washing with various weight/volume concentrations of MTEG.

As shown in FIG. 11, a strong correlation was found between the percent of MTEG in the wash buffer and the amount of recovered mRNA. As outlined above, without wishing to be bound by any particular theory, it is contemplated that the addition of water to these wash buffers results the solubilization of the mRNA during these wash steps. As shown in FIG. 11, a wash buffer with MTEG at a final concentration between 90-95% resulted in a very high yield close to the only theoretically achievable level of 100% recovery. Purity and recovery were comparable to washing conditions that employ 80% ethanol. An MTEG concentration of 95% was selected for use as wash buffer in the remaining examples.

These data further demonstrate that mRNA can be purified using a completely ethanol-free process.

Example 8. Ethanol-Free Purification of mRNA and Effect of MTEG in Wash Step This example illustrates that the amphiphilic polymer MTEG can be used during both mRNA precipitation and washing steps, without any VOCs such as ethanol, to purify mRNA with a yield and purity level suitable for therapeutic use.

Five 5 mg batches of CFTR mRNA were synthesized via IVT synthesis and 5' caps and 3' polyA tails were added as described in Example 1. Four of the resulting five 5 mg of IVT mRNA batches were each precipitated via polymer-induced precipitation. For each 5 mg batch, the mRNA, 5M GSCN-10 mM DTT buffer and MTEG were combined at the volumes provided in Table 6 below to form a suspension of precipitated mRNA. The precipitated mRNA samples were captured on Qiagen RNeasy maxi columns and washed twice with 2.5 ml of 95% MTEG. No VOCs or alcohol at all were used in the purification of the IVT synthesized mRNA. In particular, no VOCs or alcohol were used in the precipitation step or in the wash step. As an experimental control, one batch of mRNA was precipitated with ethanol, with a volume ratio of mRNA, GSCN and ethanol (100% weight/volume) of 1:2.3:1.7 as described in Example 2 and washed twice using 2 ml of 80% ethanol.

TABLE 6

Polymer wash buffers

| | Ratio of components weight/volume | | | |
|---|---|---|---|---|
| Sample | mRNA | 5M GSCN | MTEG | Final % in wash |
| 1 | 1 | 2.3 | 1 | 95% MTEG |
| 2 | 1 | 2.3 | 1.7 | 95% MTEG |
| 3 | 1 | 2.3 | 2 | 95% MTEG |
| 4 | 1 | 2.3 | 2.5 | 95% MTEG |
| Ethanol control | | | | 80% ethanol |

Figure 12:
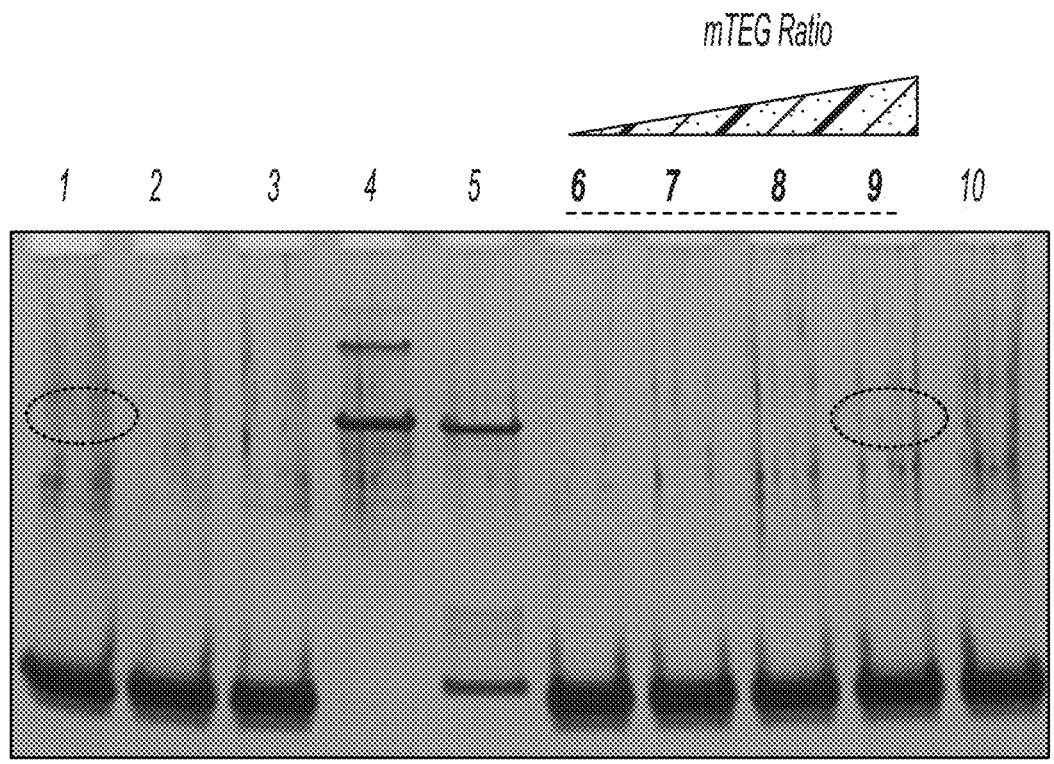
FIG. 12 shows a silver stain gel of mRNA purified via MTEG-induced precipitation using various ratios of mRNA: salt:MTEG in the suspension and washing with MTEG at a 95% weight/volume concentration.

The five samples were dissolved in 5 ml of RNase-free water and the concentration was quantified by Nano-Drop2000 spectrophotometer using absorbance at 260 nm. The purity of the mRNA samples generated from the precipitation and wash steps as observed using silver stain is shown in FIG. 12 (lanes 6-10). Precipitation and washing using MTEG achieved highly efficient mRNA recovery and purification of the mRNA. The addition of 1-2 volumes of MTEG to 1 volume mRNA and 2.3 volumes GSCN showed comparable levels of purity and yield. The addition of 2.5 volumes of MTEG to 1 volume mRNA and 2.3 volumes GSCN resulted in a faint additional band on the gel as indicated in FIG. 12. This may suggest that higher MTEG concentrations result in the precipitation of protein from the IVT reaction.

Together, these data support that mRNA purification using MTEG both during precipitation and in the wash buffer is a viable method for purifying mRNA to achieve a sufficient yield and purity level for therapeutic use.

Together these data demonstrate that MTEG mRNA purification may be used to efficiently purify high quality mRNA with resulting yield recoveries, integrity profiles and purity that is equivalent or superior to the industry-standard mRNA purification methods that employ VOCs such as alcohols, including ethanol. MTEG can replace both ethanol and high molecular weight polymers such as PEG-6000 during precipitation. In addition, MTEG can also replace ethanol or low molecular weight polymers such as PEG-400 in the washing step, making it the most versatile polymer for use in ethanol-free purification. Moreover, as outlined above, MTEG-based purification, like the other polymer-based, ethanol-free methods described herein, has a significant added benefit of scalability and safety, which is unavailable with the existing industry-standard methods that employ VOCs such as alcohols, including ethanol.

Example 9. MTEG Polymer-Induced Precipitation and MTEG Wash Buffer Applicable for Purification Using Depth Filtration and Centrifugation This example demonstrates that MTEG—due to its lower viscosity and associated superior handling properties—is surprisingly versatile and can be employed in a variety of ethanol-free mRNA purification methods at various scales, yielding recoveries exceeding 90%.

Samples were prepared in line with the examples above and purified using either depth filtration (DF) or centrifugation.

Depth Filtration Purification

For the smaller batch, 7.5 g of OTC mRNA was synthesized via IVT synthesis and 5' caps and 3' polyA tails were added as described in Example 1 and scaling reaction conditions. The mRNA was precipitated using the same MTEG polymer-induced precipitation shown in Example 7. Accordingly, the volume ratio of mRNA, GSCN (5M GSCN-10 mM DTT buffer) and MTEG (100% weight/volume) in the precipitation reaction was 1:2.3:1. The suspension was mixed at 60 Hz in a 60 L Lee vessel with bottom mounted impeller before being loaded at a flowrate of 60 L/min/m$^2$ onto the 0.11 m$^2$ depth filter having a load capacity of 68 g/m$^2$. The precipitated retained mRNA was washed using 90% MTEG at a flowrate of 60 L/min/m$^2$.

For the larger batch, 15 g of CFTR mRNA was synthesized via IVT synthesis and 5' caps and 3' polyA tails were added as described in Example 1 and scaling reaction conditions. The mRNA was precipitated using the same MTEG polymer-induced precipitation shown in Example 7. Accordingly, the volume ratio of mRNA, GSCN (5M GSCN-10 mM DTT buffer) and MTEG (100% weight/volume) in the precipitation reaction was 1:2.3:1. The suspension was mixed at 60 Hz in a 60 L Lee vessel with bottom mounted impeller before being loaded at a flowrate of 60 L/min/m$^2$ onto the 0.11 m$^2$ depth filter having a load capacity of 68 g/m$^2$. The precipitated retained mRNA was washed using 95% MTEG at a flowrate of 60 L/min/m$^2$. The flow rate was reduced to 30 L/min/m$^2$ upon increased pressure during washing. The process of filtration was repeated on the same 0.11 m$^2$ depth filter.

Centrifugation Purification 15 g of CFTR mRNA was synthesized via IVT synthesis and 5' caps and 3' polyA tails were added as described in Example 1 and scaling reaction conditions. The mRNA was precipitated using the same MTEG polymer-induced precipitation shown in Example 7. Accordingly, the volume ratio of mRNA, GSCN (5M GSCN-10 mM DTT buffer) and MTEG (100% weight/volume) in the precipitation reaction was 1:2.3:1. The suspension was mixed at 60 Hz in a 60 L Lee vessel with bottom mounted impeller and a cellulose filter aid was added at a mRNA:filter aid mass ratio of 1:10. The suspension was loaded into a filtering centrifuge and was washed with 95% MTEG.

For both purification strategies, the final mRNA yield was quantified by NanoDrop2000 spectrophotometer using absorbance at 280 nm. The % recovery of RNA is shown in Table 7 below. Furthermore, the integrity of the mRNA was assessed using CE smear analysis and the mRNA purity was assessed using silver stain analysis to detect residual process enzymes.

Results

At batch sizes of 7.5 g or more, the use of MTEG as the precipitating polymer and wash buffer component ensured very high % recovery of mRNA. As illustrated in Table 7, using the same precipitation protocol, MTEG could be employed both in centrifuge-based purification processes as well as in a filter membrane or filter cartridge-based purification processes, such as depth filtration (DF), as both the precipitation and wash buffer. The use of centrifugation yielded close to 100% recovery of the mRNA (see Table 7 below).

TABLE 7

Efficient mRNA recovery using MTEG in different purification processes

| Purification platform | Scale (g) | Filter aid (g) | % Recovery |
|---|---|---|---|
| DF | 7.5 | n/a | ~93% |
| DF | 15 | n/a | ~82% |
| H300P | 15 | 150 | ~100% |

Figure 13:
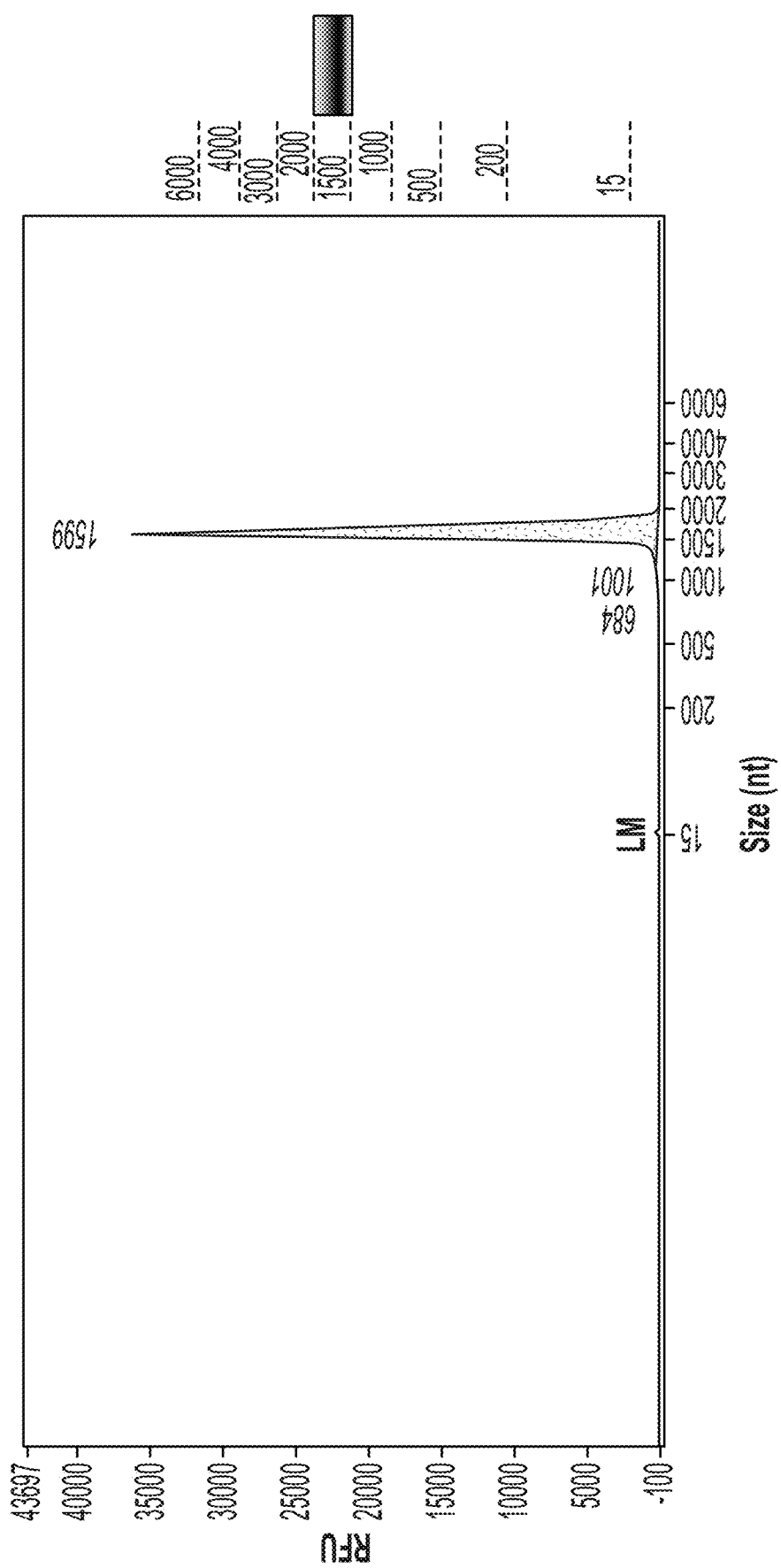
FIG. 13 shows a CE smear analysis of a 7.5 g OTC mRNA sample post-depth filtration using MTEG as the polymer for the precipitation and washing steps.
Figure 14:
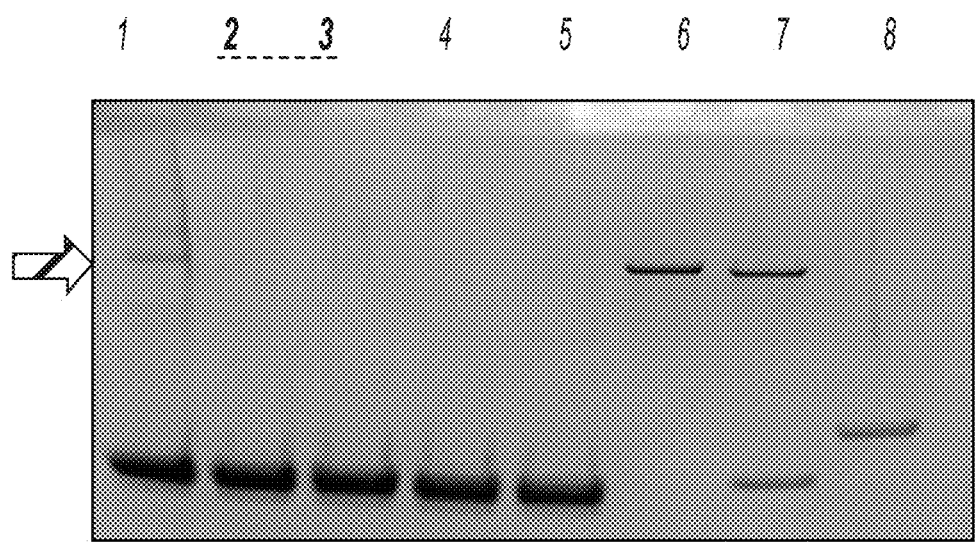
FIG. 14 shows a silver stain gel of a 7.5 g OTC mRNA sample post-depth filtration using MTEG as the polymer for the precipitation and washing steps.
Figure 15:
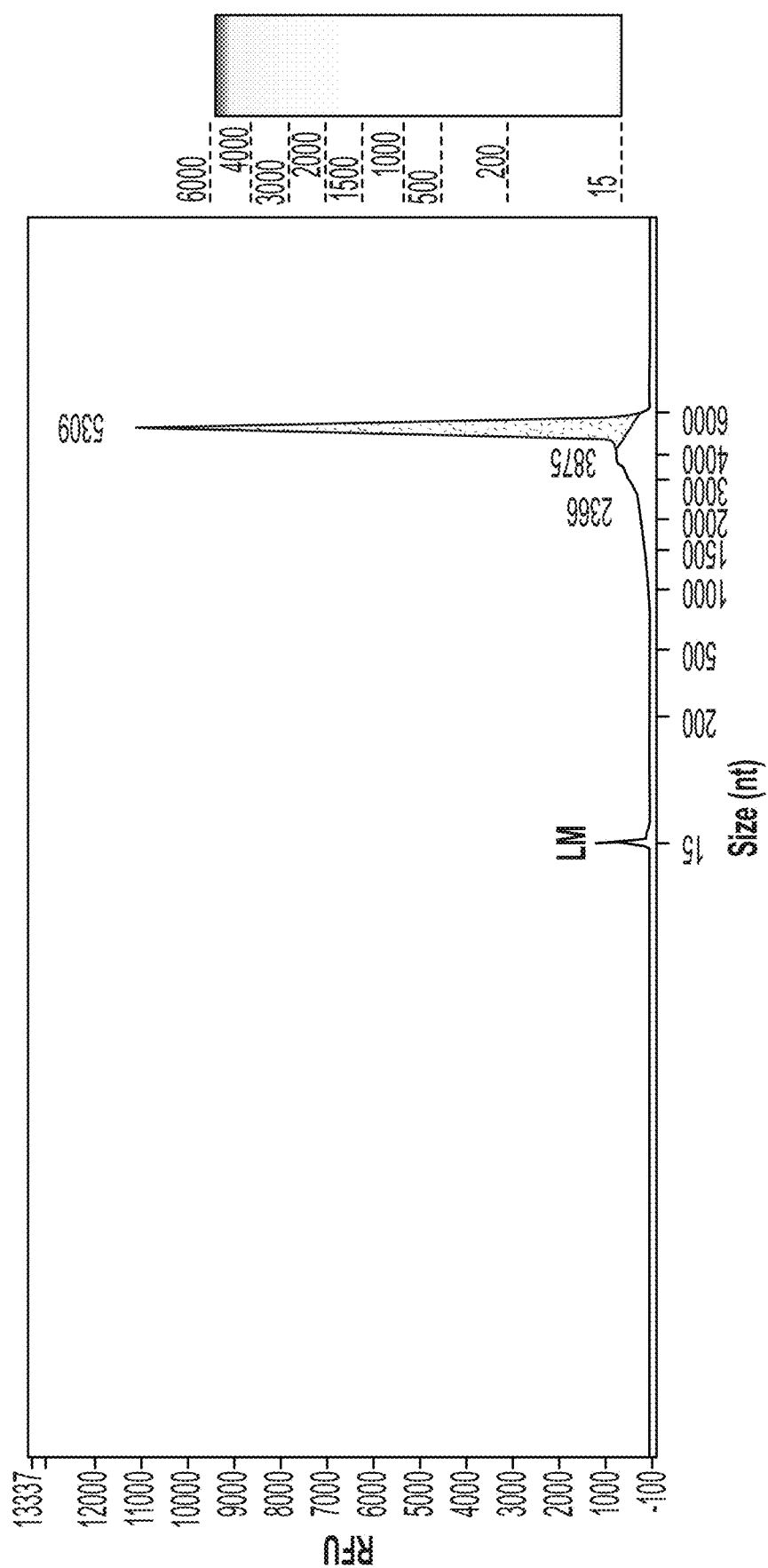
FIG. 15 shows a CE smear analysis of a 15 g CFTR mRNA sample post-depth filtration using MTEG as the polymer for the precipitation and washing steps.
Figure 16:
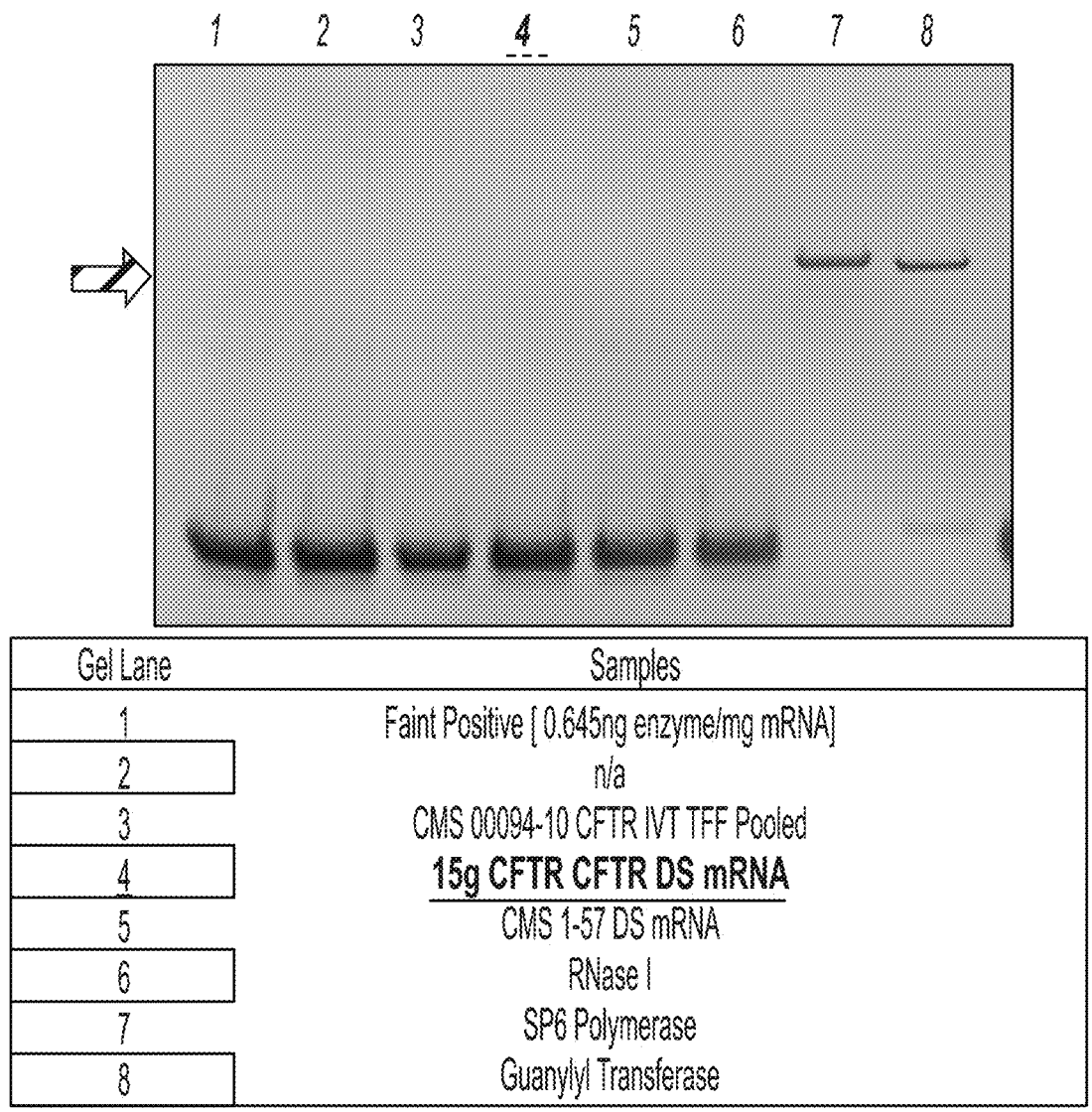
FIG. 16 shows a silver stain gel of a 15 g CFTR mRNA sample post-depth filtration using MTEG as the polymer for the precipitation and washing steps.
Figure 17:
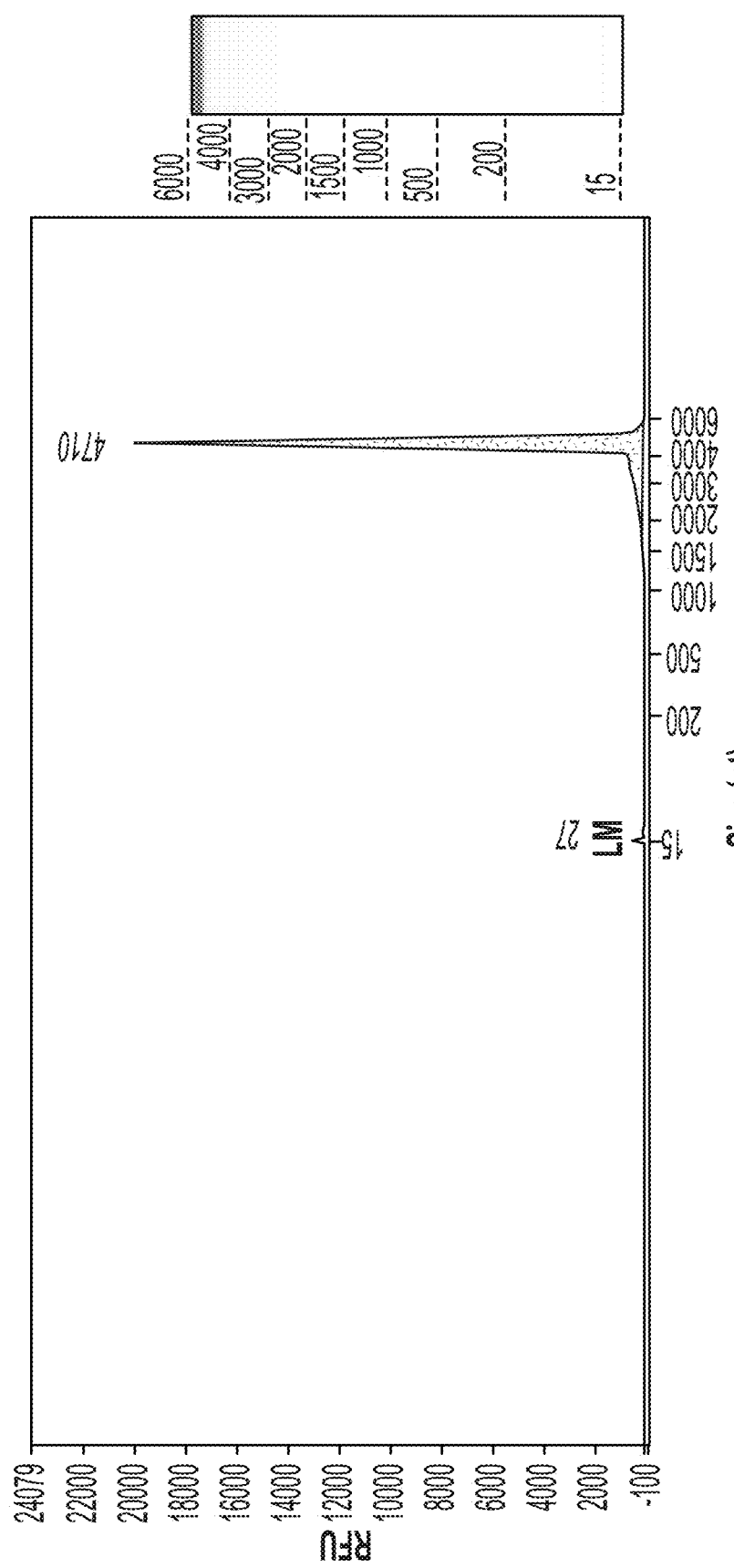
FIG. 17 shows a CE smear analysis of a 15 g CFTR mRNA sample post-centrifuge filtration using MTEG as the polymer for the precipitation and washing steps.
Figure 18:
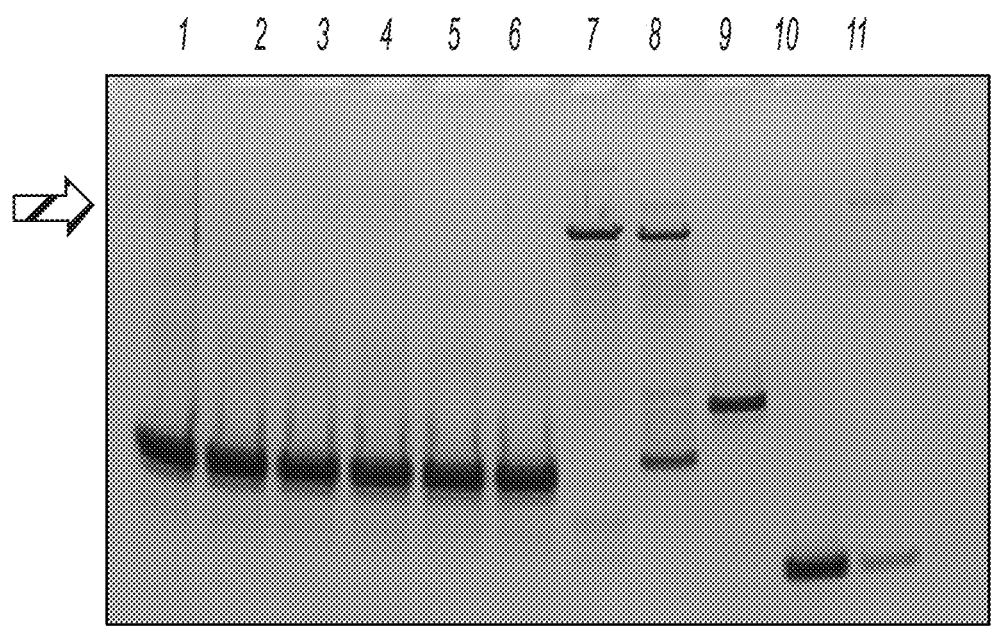
FIG. 18 shows a silver stain gel of a 15 g CFTR mRNA sample post-centrifuge filtration using MTEG as the polymer for the precipitation and washing steps.

Furthermore, the use of MTEG in both the precipitation and wash steps maintained mRNA integrity and purity. The final OTC integrity (CE) was about 92% as shown in FIG. 13. Furthermore, no residue process enzymes were detected on the silver stain (see FIG. 14). For the 15 g CFTR sample after depth filtration, the integrity was about 73% (see FIG. 15) and the purity was very high given the absence of process enzymes on the silver stain (FIG. 16). Finally, for the 15 g CFTR sample after centrifugation, not only was the yield 100%, but the integrity was about 82% (FIG. 17) and the silver stain displayed no residue process enzymes (FIG. 18). Accordingly, MTEG is a very suitable polymer for purifying mRNA using polymer-induced precipitation without the use of ethanol.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of purifying messenger RNA (mRNA) comprising:
   a) precipitating the mRNA in a suspension comprising at least a 1M salt solution and an amphiphilic polymer;
   b) capturing the mRNA on a filter; and
   c) washing the mRNA of step b) with a triethylene glycol monomethyl ether (MTEG) solution to obtain a purified mRNA composition substantially free of contaminants.

2. The method of claim 1, wherein the precipitated mRNA comprises at least 100 mg, 1 g, 10 g, 100 g, 1 kg, 10 kg, 100 kg, one metric ton, or ten metric tons, of mRNA or any amount there between.

3. The method of claim 1, wherein the high molar salt solution comprises guanidinium thiocyanate (GSCN).

4. The method of claim 1, wherein the contaminants are selected from the group consisting of one or more abortive RNA species, double-stranded RNA (dsRNA), residual plasmid DNA, residual in vitro transcription enzymes, residual solvent and residual salt.

5. A method of purifying messenger RNA (mRNA) comprising:
   a) precipitating the mRNA in a guanidinium thiocyanate (GSCN) solution comprising MTEG;
   b) centrifuging the solution of step a) to create an mRNA pellet;
   c) resuspending the mRNA pellet in a buffer;
   d) capturing the mRNA on a filter;
   e) washing the mRNA of step d) with a MTEG solution; and
   f) solubilizing the washed mRNA of step e) to obtain an mRNA composition substantially free of contaminants.

6. The method of claim 5, wherein the contaminants are selected from the group consisting of one or more abortive RNA species, double-stranded RNA (dsRNA), residual plasmid DNA, residual in vitro transcription enzymes, residual solvent and residual salt.

7. The method of claim 1, wherein the amphiphilic polymer comprises MTEG.

8. The method of claim 1, wherein the suspension comprises precipitated mRNA, a high molar salt solution and MTEG.

* * * * *